United States Patent
Mclaughlin et al.

(10) Patent No.: US 12,208,160 B2
(45) Date of Patent: *Jan. 28, 2025

(54) PHARMACEUTICAL COMPOSITIONS COMPRISING COATED API

(71) Applicant: Catalent U.K. Swindon Zydis Limited, Glasgow (GB)

(72) Inventors: Rosaleen Mclaughlin, Swindon (GB); Simon Andrew Martyn Howes, Swindon (GB); Craig Wheadon, Swindon (GB); Jonathon Whitehouse, Herne Bay (GB); Adam Parker, Swindon (GB); Michael John Hutchinson, Lisburn (GB)

(73) Assignee: Catalent U.K. Swindon Zydis Limited, Swindon (GB)

( * ) Notice: Subject to any disclaimer, the term of this patent is extended or adjusted under 35 U.S.C. 154(b) by 104 days.

This patent is subject to a terminal disclaimer.

(21) Appl. No.: 17/390,331

(22) Filed: Jul. 30, 2021

(65) Prior Publication Data

US 2022/0031610 A1    Feb. 3, 2022

Related U.S. Application Data

(60) Provisional application No. 63/059,684, filed on Jul. 31, 2020.

(51) Int. Cl.
*A61K 9/28* (2006.01)
*A61K 9/00* (2006.01)

(52) U.S. Cl.
CPC .......... *A61K 9/0056* (2013.01); *A61K 9/2813* (2013.01); *A61K 9/2826* (2013.01); *A61K 9/2873* (2013.01); *A61K 9/2893* (2013.01)

(58) Field of Classification Search
None
See application file for complete search history.

(56) References Cited

U.S. PATENT DOCUMENTS

| | | |
|---|---|---|
| 4,305,502 A | 12/1981 | Gregory et al. |
| 4,371,516 A | 2/1983 | Gregory et al. |
| 4,758,598 A | 7/1988 | Gregory |
| 5,008,117 A | 4/1991 | Calanchi et al. |
| 5,320,848 A | 6/1994 | Geyer |
| 5,558,880 A | 9/1996 | Gole et al. |
| 5,976,577 A | 11/1999 | Green et al. |
| 6,214,386 B1 | 4/2001 | Santus |
| 6,413,549 B2 | 7/2002 | Green et al. |
| 6,509,040 B1 | 1/2003 | Murray et al. |
| 6,709,669 B1 | 3/2004 | Murray et al. |
| 6,951,657 B1 | 10/2005 | Zuccarelli |
| 9,107,851 B2 | 8/2015 | Dave et al. |
| 11,077,067 B2 * | 8/2021 | McLaughlin .......... A61K 9/501 |
| 2003/0185096 A1 | 10/2003 | Hollstein et al. |
| 2003/0195179 A1 | 10/2003 | Sawa |
| 2004/0137061 A1 | 7/2004 | Ishibashi et al. |
| 2004/0170686 A1 | 9/2004 | Fredrickson et al. |
| 2004/0265373 A1 | 12/2004 | Wynn et al. |
| 2007/0148099 A1 | 6/2007 | Burke et al. |
| 2007/0292508 A1 | 12/2007 | Szamosi et al. |
| 2008/0075825 A1 | 3/2008 | Fuisz et al. |
| 2008/0096979 A1 | 4/2008 | Pilgaonkar |
| 2008/0113021 A1 | 5/2008 | Shen |
| 2008/0311201 A1 | 12/2008 | Der-Yang et al. |
| 2008/0317853 A1 | 12/2008 | Kashid et al. |
| 2009/0062241 A1 | 3/2009 | Bauer |
| 2009/0148524 A1 | 6/2009 | Higuchi et al. |
| 2011/0229573 A1 | 9/2011 | Tian |
| 2014/0105936 A1 | 4/2014 | Limonov et al. |
| 2014/0106059 A1 | 4/2014 | Dave et al. |
| 2016/0361335 A1 | 12/2016 | Jacob et al. |
| 2020/0268667 A1 | 8/2020 | McLaughlin et al. |
| 2020/0268668 A1 * | 8/2020 | McLaughlin .......... A61K 9/2081 |
| 2020/0268676 A1 | 8/2020 | McLaughlin |
| 2020/0268677 A1 | 8/2020 | McLaughlin et al. |
| 2023/0390205 A1 | 12/2023 | Mclaughlin et al. |

FOREIGN PATENT DOCUMENTS

| | | |
|---|---|---|
| CA | 2398288 A1 | 8/2001 |
| CA | 2512988 A1 | 8/2004 |
| CN | 102300558 A | 12/2011 |
| CN | 102579390 A | 7/2012 |
| CN | 103169655 A | 6/2013 |
| CN | 104853751 A | 8/2015 |
| EP | 0636365 A1 | 2/1995 |
| EP | 1405635 A1 | 4/2004 |

(Continued)

OTHER PUBLICATIONS

Examination Report dated Feb. 6, 2023, directed to GB Application No. 2002466.7; 4 pages.
Examination Report dated Feb. 8, 2023, directed to GB Application No. 2107172.5; 3 pages.
Examination Report dated Feb. 14, 2023, directed to GB Application No. 2002475.8; 3 pages.
McLaughlin et al., U.S. Office Action dated Feb. 6, 2023, directed to U.S. Appl. No. 17/307,638; 17 pages.
Office Action dated Feb. 22, 2023, directed to IN Application No. 202127042578; 5 pages.

(Continued)

*Primary Examiner* — Susan T Tran
(74) *Attorney, Agent, or Firm* — Morrison & Foerster LLP

(57) ABSTRACT

Provided are pharmaceutical compositions and methods for preparing pharmaceutical compositions comprising coated API. Excess coating material that is not bound to coated API may be removed by a sieving process. Coating and dosing ratios can also be optimized to minimize the amount of excess unbound coating material. Additionally, the compositions can be formulated to preserve the functional coating of coated API and to minimize aeration of API when mixed into suspension.

23 Claims, 26 Drawing Sheets

(56) References Cited

FOREIGN PATENT DOCUMENTS

| | | | |
|---|---|---|---|
| EP | 1621186 A1 | 2/2006 | |
| EP | 1980245 A1 | 10/2008 | |
| GB | 211423 A | 2/1924 | |
| GB | 1548022 A | 7/1979 | |
| JP | H9-511256 A | 11/1997 | |
| JP | 2002-012557 A | 1/2002 | |
| JP | 2003-055197 A | 2/2003 | |
| JP | 2003-525223 A | 8/2003 | |
| JP | 2007-525413 A | 9/2007 | |
| JP | 2008-508255 A | 3/2008 | |
| JP | 2008-517979 A | 5/2008 | |
| JP | 2008-526827 A | 7/2008 | |
| JP | 2015-533162 A | 11/2015 | |
| JP | 2017-532331 A | 11/2017 | |
| TW | 512167 B | 12/2002 | |
| WO | 92/22369 A1 | 12/1992 | |
| WO | WO-0154683 A1 * | 8/2001 | ........... A61K 31/192 |
| WO | 02/47607 A2 | 6/2002 | |
| WO | 2004/066925 A2 | 8/2004 | |
| WO | 2006/045830 A1 | 5/2006 | |
| WO | 2006/072832 A1 | 7/2006 | |
| WO | 2008/036299 A2 | 3/2008 | |
| WO | WO-2009108775 A2 * | 9/2009 | ........... A61K 31/551 |
| WO | 2011/063531 A1 | 6/2011 | |
| WO | 2013/024373 A1 | 2/2013 | |
| WO | WO-2013183062 A2 * | 12/2013 | ........... A61K 31/192 |
| WO | WO-2014062444 A1 * | 4/2014 | ........... A61K 9/5042 |
| WO | 2017/080566 A1 | 5/2017 | |
| WO | 2020/169989 A1 | 8/2020 | |

OTHER PUBLICATIONS

Office Action dated Feb. 27, 2023, directed to EP Application No. 20708584.6; 5 pages.
First Office Action dated Nov. 3, 2022, directed to CN Application No. 202080015446.5; 22 pages.
Written Opinion dated Nov. 2, 2022, directed to SG Application No. 11202108659X; 8 pages.
Written Opinion dated Nov. 2, 2022, directed to SG Application No. 11202109104X; 7 pages.
McLaughlin et al., U.S. Office Action dated Aug. 23, 2022, directed to U.S. Appl. No. 16/798,067; 15 pages.
McLaughlin et al., U.S. Office Action dated Dec. 22, 2022, directed to U.S. Appl. No. 16/798,067; 14 pages.
Written Opinion dated Nov. 2, 2022, directed to SG Application No. 11202109022U; 8 pages.
Written Opinion dated Nov. 3, 2022, directed to SG Application No. 11202108690Y; 11 pages.
Combined Search and Examination Report dated Apr. 28, 2020, directed to GB Application No. 2002466.7; 5 pages.
Combined Search and Examination Report dated Apr. 28, 2020, directed to GB Application No. 2002475.8; 7 pages.
Combined Search and Examination Report dated Apr. 28, 2020, directed to GB Application No. 2002479.0; 8 pages.
Combined Search and Examination Report dated Apr. 28, 2020, directed to GB Application No. 2002484.0; 7 pages.
International Search Report and Written Opinion mailed Apr. 17, 2020, directed to International Application No. PCT/GB2020/050419; 15 pages.
International Search Report and Written Opinion mailed Apr. 20, 2020, directed to International Application No. PCT/GB2020/050420; 13 pages.
International Search Report and Written Opinion mailed Apr. 21, 2020, directed to International Application No. PCT/GB2020/050422; 14 pages.
International Search Report and Written Opinion mailed Apr. 21, 2020, directed to International Application No. PCT/GB2020/050423; 14 pages.
McLaughlin et al., Office Action dated Apr. 12, 2021, directed to U.S. Appl. No. 16/797,927; 21 pages.
McLaughlin et al., Office Action dated Apr. 13, 2021, directed to U.S. Appl. No. 16/798,130; 29 pages.
McLaughlin et al., Office Action dated Dec. 7, 2020, directed to U.S. Appl. No. 17/008,318; 16 pages.
McLaughlin et al., Office Action dated Dec. 9, 2020, directed to U.S. Appl. No. 17/008,108; 22 pages.
McLaughlin et al., Office Action dated Feb. 10, 2021, directed to U.S. Appl. No. 16/797,934; 24 pages.
McLaughlin et al., Office Action dated May 12, 2021, directed to U.S. Appl. No. 16/797,934; 22 pages.
National Center for Biotechnology Information. (Apr. 28, 2006). "Compound Summary—Simethicone," located at https://pubchem.ncbi.nlm.nih.gov/compound/Simethicone (2 pages).
O'Connell (May 2005). "Sieve Use in the Pharmaceutical Industry," Pharmaceutical Technology Europe 17(5): 7 pages.
Zhou et al. (Aug. 2013). "Improving manufacturability of an ibuprofen powder blend by surface coating with silica nanoparticles," Powder Technology 249: 290-296.
Combined Search and Examination Report dated Nov. 22, 2021, directed to GB Application No. 2107172.5; 4 pages.
Combined Search and Examination Report dated Nov. 22, 2021, directed to GB Application No. 2107174.1; 4 pages.
Combined search and examination report dated Nov. 22, 2021, directed to GB Application No. 2107177.4; 5 pages.
International Search Report and Written Opinion dated Nov. 5, 2021, directed to International Application No. PCT/IB2021/056976; 15 pages.
Syloid FG Silica (2015) "Syloid 244 FP silica: Formulation of viscous Simethicone in to chewable tablets," located at https://www.pharmaexcipients.com/wp-content/uploads/attachments/AP010_Syloid+244+FP-Formulation+of+Simethicone+into+chewable+tablets_Final.pdf?t=1458129627. (2 pages).
Anonymous. (2014). "Safety Data Sheet Orange Tincture," located at <https://jmloveridge.com/wp-content/uploads/2018/06/Orange-Tincture-Version-06.pdf> retrieved on Mar. 24, 2022; 6 pages.
Deterre et al. (2014). "Classification of commercial bitter orange essential oils (Citrus aurantium L.), based on a combination of chemical and sensory analyses of specific odor markers," Journal of Essential Oil Research 26 (4): 254-262.
McLaughlin et al., U.S. Office Action dated Mar. 30, 2022, directed to U.S. Appl. No. 16/798,067; 20 pages.
Andrews. (2017)."How to Extract Oil from Orange Peels," downloaded from URL https://web.archive.org/web/20170603094953/https://www.wikihow.com/Extract-Oil-from-Orange-Peels retrieved on May 24, 2023; 5 pages.
Andrews. (2018) "How to Extract Oil from the Skin of Oranges," downloaded from https://www.weekand.com/healthy-living/article/extract-oil-skin-oranges-18009337.php retrieved on May 24, 2023; 4 pages.
Anonymous. (2013). "Making Orange Tincture," downloaded from https://boozyblog.wordpress.com/ 2013/08/05/making-orange-tincture/ retrieved on May 24, 2023; 7 pages.
Bourgou et al. (2012). "Changes of Peel Essential Oil Composition of Four Tunisian Citrus during Fruit Maturation," The Scientific World Journal; Article ID 528593; 10 pages.
Evonik-Glenn Corp. "Aerosil® R972," located at https://glenncorp.com/shop/aerosil-r-972/, retrieved on May 16, 2023.(1 page).
Jabri Karoui et al. (2013). "Characterization of Bioactive Compounds in Tunisian Bitter Orange (Citrus aurantium L.) Peel and Juice and Determination of Their Antioxidant Activities," BioMed Research International; Article ID: 345415; 12 pages.
McLaughlin et al., U.S. Advisory Action dated Jun. 21, 2023, directed to U.S. Appl. No. 16/798,067; 5 pages.
McLaughlin et al., U.S. Office Action dated Aug. 29, 2023, directed to U.S. Appl. No. 16/798,067; 16 pages.
McLaughlin et al., U.S. Office Action dated Jun. 16, 2023, directed to U.S. Appl. No. 17/529,827; 26 pages.
McLaughlin et al., U.S. Office Action dated May 15, 2023, directed to U.S. Appl. No. 17/387,803; 18 pages.
Office Action dated Aug. 9, 2023, directed to MX Application No. MX/a/2021/009844; 5 pages.
Office Action dated Jul. 10, 2023, directed to RU Application No. 2021127592; 37 pages.

(56) References Cited

OTHER PUBLICATIONS

Office Action dated Jul. 11, 2023, directed to MX Application No. MX/a/2021/009845; 6 pages.
Office Action dated Jul. 12, 2023, directed to RU Application No. 2021127591; 25 pages.
Office Action dated Jul. 14, 2023, directed to RU Application No. 2021127588; 22 pages.
Office Action dated Jul. 28, 2023, directed to IN Application No. 202127042579; 8 pages.
Office Action dated Jun. 1, 2023, directed to GB Application No. 2107172.5; 1 page.
Office Action dated Jun. 23, 2023, directed to MX Application No. MX/a/2021/009679; 6 pages.
Office Action dated Jun. 27, 2023, directed to MX Application No. MX/a/2021/009681; 6 pages.
Office Action dated May 2, 2023, directed to IN Application No. 202127042581; 6 pages.
Office Action dated May 22, 2023, directed to CN Application No. 202080015446.5; 8 pages.
Office Action dated May 31, 2023, directed to GB Application No. 2002466.7; 1 page.
Office Action dated May 31, 2023, directed to GB Application No. 2002475.8; 2 pages.
Office Action dated May 31, 2023, directed to IN Application No. 202127042580; 6 pages.
McLaughlin et al., U.S. Office Action dated Sep. 13, 2023, directed to U.S. Appl. No. 17/387,803; 10 pages.
McLaughlin et al., U.S. Office Action dated Sep. 13, 2023, directed to U.S. Appl. No. 17/529,827; 15 pages.
Office Action dated Jul. 18, 2023, directed to TW Application No. 109105762; 14 pages.
Office Action dated Jul. 26, 2023, directed to TW Application No. 109105759; 12 pages.
Office Action dated Sep. 26, 2023, directed to MX Application No. MX/a/2021/09679; 10 pages.
Bikiaris et al., (2007). "New Aspects in Sustained Drug Release Formulations," Recent Patents on Drug Delivery & Formulation 1(3): 201-213.
Chueshov et al. (2002). Industrial Drug Technology. vol. 2; pp. 352-355.
Extended European Search Report dated Dec. 18, 2023, directed to EP Application No. 23183926.7; 8 pages.
Extended European Search Report dated Jan. 23, 2024, directed to EP Application No. 23186234.3; 10 pages.
Extended European Search Report dated Jan. 31, 2024, directed to EP Application No. 23189317.3; 16 pages.
First Office Action dated Dec. 27, 2023, directed to CN Application No. 202080015572.0; 34 pages.
Gad, 2005. "Limonene," Encyclopedia of Toxicology (Second Edition), pp. 720-725.
McLaughlin et al., U.S. Office Action dated Mar. 4, 2024, directed to U.S. Appl. No. 17/529,827; 19 pages.
Notice of Reasons for Rejection dated Dec. 4, 2023, directed to JP Application No. 2021-549375; 11 pages.
Office Action dated Dec. 11, 2023, directed to RU Application No. 2021127590; 24 pages.
Office Action dated Dec. 12, 2023, directed to RU Application No. 2021127588; 16 pages.
Office Action dated Dec. 6, 2023, directed to RU Application No. 2021127592; 17 pages.
Office Action dated Dec. 7, 2023, directed to RU Application No. 2021127591; 14 pages.
Office Action dated Dec. 7, 2023, directed to TW Application No. 109105759; 8 pages.
Office Action dated Feb. 22, 2024, directed to MX Application No. MX/a/2021/009681; 8 pages.
Office Action dated Jan. 30, 2024, directed to MX Application No. MX/a/2021/009679; 9 pages.
Office Action dated Jan. 9, 2024, directed to JP Application No. 2021-549372; 9 pages.
Office Action dated Jan. 9, 2024, directed to JP Application No. 2021-549373; 12 pages.
Office Action dated Jul. 13, 2023, directed to RU Application No. 2021127590; 30 pages.
Office Action dated Nov. 1, 2023, directed MX Application No. MX/a/2021/009845; 11 pages.
Office Action dated Nov. 4, 2023, directed to CN Application No. 202080015635.2; 23 pages.
Office Action dated Nov. 7, 2023, directed to TW Application No. 109105773; 10 pages.
Office Action dated Nov. 8, 2023, directed to TW Application No. 109105762; 10 pages.
Office Action dated Nov. 9, 2023, directed to CN Application No. 202080015564.6; 28 pages.
Pertsev et al. (1999). Pharmaceutical and biomedical aspects of drugs, vol. 1; pp. 253-254.
Subsequent Substantive Examination Report dated Jan. 12, 2024, directed to EP Application No. 1/2021/552022; 4 pages.
Office Action dated Nov. 17, 2023, directed to MX Application No. MX/a/2021/009844; 6 pages.
Office Action dated Nov. 3, 2023, directed to TW Application No. 109105770; 8 pages.
Office Action dated Oct. 12, 2023, directed to MX Application No. MA/a/2021/009681; 9 pages.
Office Action dated Sep. 28, 2023, directed to PH Application No. 1/2021/552022; 4 pages.
Third Office Action dated Sep. 18, 2023, directed to CN Application No. 202080015446.5; 10 pages.
McLaughlin et al., U.S. Office Action dated Mar. 7, 2024, directed to U.S. Appl. No. 16/798,067; 21 pages.
Office Action dated Mar. 11, 2024, directed to JP Application No. 2021-549374; 11 pages.
Office Action dated Mar. 21, 2024, directed to IL Application No. 285640; 4 pages.
Office Action dated Mar. 27, 2024, directed to IL Application No. 285648; 4 pages.
Office Action dated Mar. 4, 2024, directed to IN Application No. 202127042580; 3 pages.
Office Action dated Mar. 5, 2024, directed to MX Application No. MX/a/2021/009844; 7 pages.
Decision of Rejection dated Jul. 8, 2024, directed to JP Application No. 2021-549375; 7 pages.
Huang et al., (2017). "Improving blend content uniformity via dry particle coating of micronized drug powders," European Journal of Pharmaceutical Sciences 104: 344-355.
McLaughlin et al., U.S. Office Action dated Jul. 17, 2024, directed to U.S. Appl. No. 16/798,067; 21 pages.
McLaughlin et al., U.S. Office Action dated Jul. 25, 2024, directed to U.S. Appl. No. 17/529,827; 23 pages.
Office Action dated Apr. 18, 2024, directed to IL Application No. 285653; 4 pages.
Office Action dated Apr. 22, 2024, directed to MX Application No. MX/a/2021/009845; 5 pages.
Office Action dated Jun. 18, 2024, directed to MX Application No. MX/a/2021/009681; 11 pages.
Office Action dated May 6, 2024, directed to TW Application No. 109105773; 9 pages.
Office Action dated May 7, 2024, directed to CN Application No. 202180051278.X; 20 pages.
Office Action dated May 9, 2024, directed to MX Application No. MX/a/2021/009679; 10 pages.

\* cited by examiner

PHARMACEUTICAL COMPOSITIONS COMPRISING COATED API

CROSS-REFERENCE TO RELATED APPLICATION

This application claims the priority of U.S. Provisional Application No. 63/059,684, filed Jul. 31, 2020, the entire contents of which are incorporated herein by reference.

FIELD OF THE DISCLOSURE

This relates to processes for coating API and incorporating the coated API into lyophilized orally disintegrating dosage forms. Specifically, this relates to processes for coating API that include water insoluble materials and silica.

BACKGROUND OF THE DISCLOSURE

Pharmaceutical compositions typically include both an active pharmaceutical ingredient as well as one or more inactive ingredients. The active pharmaceutical ingredient (API) can be biologically active and be designed to directly affect a patient's symptoms, diseases, disorders, and/or ailments. One example of an active pharmaceutical ingredient is Ibuprofen. The inactive ingredient(s) of a pharmaceutical composition, on the other hand, are pharmaceutically inert and can be used for various purposes including, but not limited to, improving long-term stabilization, filling or diluting a solid formulation, facilitating drug absorption, modifying viscosity of liquid formulations, enhancing solubility, and/or aiding the manufacture of the pharmaceutical composition.

In addition, some inactive ingredients may be used to mask the taste of the API, such as Ibuprofen. Many APIs are known to exhibit unpleasant organoleptic properties if allowed to dissolve in the oral cavity, such as bitter taste, burning sensation, and numbing. For example, some orally-administered pharmaceutical compositions are designed to disperse in the mouth to enable administration without water and are targeted to pediatric patients, geriatric patients, animal patients, and/or other types of patients that may have difficulties swallowing. For these types of orally-administered pharmaceutical compositions, an inactive ingredient may be used to form a "functional coating" to mask the taste of the API.

For example, an inactive ingredient may be used to mask the taste of the API by wet coating or dry coating the API particle to produce a functional coating surrounding the API particle such that it prevents API release in the mouth. In wet particle coating, inactive ingredients (polymer and additives) are dissolved or dispersed in solvent or water to form a suspension or solution. This suspension or solution can then be sprayed onto the surface of the API particle to form a coating of film by evaporation of the solvent or water. Examples of technologies for wet particle coating include microencapsulation, fluid bed coating, spray drying, pan coating etc. In dry particle coating (also referred to as solventless coating), API particles are physically coated with fine particles of inactive ingredients (polymer and additives) to form particle composites. Examples of dry particle coating include hot melt coating, supercritical coating, impaction coating, electrostatic coating. API particles coated with a taste-masking inactive ingredient may provide a more pleasant experience for a patient having difficulties swallowing or having a sensitivity to taste that would otherwise lead to a negative patient experience and poor compliance.

Additionally, one type of pharmaceutical composition is an orally-disintegrating tablet (ODT). ODTs are pharmaceutical compositions typically targeted to pediatric patients, geriatric patients, animal patients, and/or other types of patients that may have difficulties swallowing.

To accurately dispense a pharmaceutical composition into a small, administrable form, a hydrophobic coated API particle can be placed in a matrix solution/suspension to form a pharmaceutical suspension. Mixing to form a pharmaceutical suspension allows for improved dosing accuracy. Oftentimes, this pharmaceutical suspension comprising the hydrophobic coated API particles can be dosed into molds, dried, and the molded article can then be transferred into a bottle, for example. However, this kind of handling of the pharmaceutical composition can increase risks such as damage and contamination.

Accordingly, many API suspensions today are dosed into preformed blister packs instead. Preformed blister packs eliminate one of the handling steps described above. Instead of dosing into a mold and then transferring the molded article to a bottle for packaging, preformed blister packs allow a manufacturer to dose the pharmaceutical suspension into a preformed blister pack that can be frozen, dried, then sealed and packaged. Thus, the preformed blister pack serves as both the mold and the package in which the pharmaceutical composition can be stored.

SUMMARY OF THE DISCLOSURE

Applicants have discovered an API coating process that can eliminate water soluble and/or water swellable materials from the coating. Instead, the coated API can be coated with a water insoluble material such as a wax. In addition, the API can be coated with a second coating material (e.g., silica) which can be in the same coating as the water insoluble material, in a second coating on top of the water insoluble material coating, or a combination thereof. Furthermore, Applicants discovered that the coating process of the API does not need a coating or milling media. Instead, the API can simply be coated using a first coating material (e.g., water insoluble materials) and a second coating material (e.g., silica) and mechanical and/or thermal energy applied to the combination of the API, first coating material, and second coating material.

In addition, provided are methods for minimizing agglomeration of coating material for coated API produced using various mixing processes. Agglomeration of coating material can decrease the stability of the pharmaceutical product over time. For example, a pharmaceutical product's disintegration time may increase over time if it comprises agglomerated coating material. An increased disintegration times and/or a decreased dissolution rate implies an unstable pharmaceutical product. An unstable pharmaceutical product can lead to a shorter shelf life than desired. Accordingly, embodiments provided may help minimize agglomeration of coating material for coated API to improve the stability of the pharmaceutical product during storage and to increase its shelf life.

For example, methods described include removing excess coating material from the coated API to minimize the possibility of agglomeration of the coating material particles. Particularly, methods provided include sieving the coated API such that the final pharmaceutical product is adequately surrounded by dry matrix, minimizing any agglomeration of coating material particles upon storage.

Pharmaceutical compositions described provide for a disintegration time and a dissolution rate that remain relatively stable over time.

Also provided are compositions and methods for preparing compositions that can minimize aeration of hydrophobic coated API in suspension. For example, hydrophobic coated API may be mixed into a matrix solution/suspension to form a pharmaceutical suspension to accurately dose into molds to form solid pharmaceutical compositions (e.g., article, tablet, etc.) for administering to a patient. However, the hydrophobicity of the coated API can cause the coated API to resist dispersing into the solution/suspension. Consequently, this can cause air to become entrained with the pharmaceutical suspension, also known as aeration. Entrained air, or aeration of the pharmaceutical suspension, can cause phase separation of the coated API in the pharmaceutical suspension, causing a non-homogenous pharmaceutical suspension. Aeration and non-homogeneous pharmaceutical suspensions can lead to poor dose weight accuracy of the pharmaceutical suspension comprising the hydrophobic API dosed into preformed blister packs and poor content uniformity in the finished product (i.e., pharmaceutical composition).

Traditional mechanical means of anti-aeration and/or minimizing aeration have not been found to be successful due to the high viscosity of the pharmaceutical suspension. For example, minimizing aeration may be achieved by applying vacuum to a pharmaceutical suspension, but depending on the composition and further processing requirements, this approach may not be suitable. In particular, applying a vacuum to the pharmaceutical suspension can cause the suspension to rise because the viscous suspension "holds onto" the entrained air. Volatile formulation components may also be lost during vacuum processing. Further, traditional anti-aerating agents, such as ethanol or simethicone emulsion are similarly ineffective at anti-aerating the suspension.

Accordingly, compositions and methods provided herein minimize the aeration of a pharmaceutical suspension comprising hydrophobic coated API to improve the homogeneity of the suspension and increase the dose weight accuracy. Specifically, embodiments provided can include matrix solutions/suspensions comprising chemical compounds comprising terpene and/or terpinol. In some embodiments, a matrix solution/suspension may comprise the terpene limonene. By introducing a terpene-comprising chemical compound such as limonene, the hydrophobic coated API may more readily incorporate into the matrix solution/suspension, minimizing the overall aeration of the pharmaceutical suspension.

Also provided herein are pharmaceutical compositions and methods for preparing pharmaceutical compositions that are formulated to preserve the functional coating of functionally-coated API during the manufacture process. Functionally-coated API are often mixed to form a pharmaceutical suspension. A pharmaceutical suspension allows for accurate dosing to form an administrable pharmaceutical product. Typically, shear forces required to incorporate the functionally-coated API into a pharmaceutical suspension can cause the functional coating to erode. Erosion of this coating can destroy or damage the properties of the functional coating. Accordingly, functionally-coated API with an eroded coating can experience an increased dissolution rate and decreased taste-masking properties when orally administered to a patient.

However, pharmaceutical compositions and methods for preparing pharmaceutical compositions provided herein include preserving the coating of functionally-coated API in the pharmaceutical suspension with hydrophobic fumed silica. Specifically, the hydrophobic fumed silica can provide a protective layer surrounding and/or embedded into the functionally-coated API particle. In some embodiments, solventless processes for producing functionally-coated API may produce API comprising a first coating. According to some embodiments, hydrophobic fumed silica can be added during the solventless mixing process to produce a second, protective coating surrounding and/or partially or fully embedded into the functionally-coated API.

Additionally, the second, protective coating may limit the interaction between the functionally-coated API and the matrix solution/suspension such that impact of the functionally-coated API on the performance characteristics of the matrix is minimized.

In some embodiments, a pharmaceutical composition includes: 85-95% w/w API comprising at least one coating, wherein the at least one coating comprises a water insoluble material and silica; 3-7% w/w matrix former; and 2-6% w/w structure former. In some embodiments, the water insoluble material comprises 10-30% w/w of the API comprising the at least one coating. In some embodiments, the silica comprises 0.5-2% w/w of the API comprising the at least one coating. In some embodiments, the water insoluble material comprises a wax. In some embodiments, the wax comprises carnauba wax. In some embodiments, the silica comprises hydrophobic silica. In some embodiments, the matrix former comprises gelatin. In some embodiments, the structure former comprises mannitol. In some embodiments, the pharmaceutical composition includes a viscosity modifier. In some embodiments, the pharmaceutical composition comprises 0.1-1% w/w viscosity modifier. In some embodiments, the viscosity modifier comprises xanthan gum. In some embodiments, the pharmaceutical composition includes a sweetener. In some embodiments, the pharmaceutical composition comprises 0.1-2% w/w sweetener. In some embodiments, the sweetener is sucralose. In some embodiments, the pharmaceutical composition includes a flavoring agent. In some embodiments, the pharmaceutical composition comprises 0.5-3% w/w flavoring agent. In some embodiments, the flavoring agent comprises terpene and/or terpinol. In some embodiments, the pharmaceutical composition has a mid volume 60-minute dissolution test result less than or equal to 70% after 15 minutes. In some embodiments, the pharmaceutical composition has a mid volume 60-minute dissolution test result less than or equal to 85% after 30 minutes. In some embodiments, the pharmaceutical composition has a mid volume 60-minute dissolution test result less than or equal to 90% after 45 minutes. In some embodiments, the pharmaceutical composition has a mid volume 60-minute dissolution test result less than or equal to 95% after 60 minutes.

In some embodiments, a method of preparing coated API includes sieving raw API; mixing sieved raw API and a water insoluble material in a vessel; applying mechanical energy to the vessel and heating the vessel to a temperature greater than or equal to 50° C.; and adding silica to the vessel while continuing to apply the mechanical energy and maintaining the temperature of the vessel to form coated API comprising at least one coating comprising water insoluble material and silica. In some embodiments, sieving the raw API comprises sieving the raw API to an average particle size of 75-250 microns. In some embodiments, the method includes sieving the coated API. In some embodiments, sieving the coated API comprises sieving the coated API to an average particle size of 75-250 microns. In some embodiments, the water insoluble material comprises wax. In some embodiments, the wax comprises carnauba wax. In some embodiments, the silica comprises hydrophobic silica. In some embodiments, the ratio of the at least one coating to the API of the API comprising at least one coating is 15-40:60-85.

In some embodiments, a method of preparing a pharmaceutical composition includes forming a pharmaceutical suspension comprising: 30-50% w/w API comprising at least one coating, wherein the at least one coating comprises a water insoluble material and silica; 1-5% w/w a matrix former; 1-3% w/w a structure former; and a solvent; dosing the pharmaceutical suspension into a mold; and freeze drying the dosed pharmaceutical suspension in the mold to form the pharmaceutical composition. In some embodiments, the water insoluble material comprises 10-30% w/w of the API comprising the at least one coating. In some embodiments, the silica comprises 0.5-2% w/w of the API comprising the at least one coating. In some embodiments, the water insoluble material comprises a wax. In some embodiments, the wax comprises carnauba wax. In some embodiments, the silica comprises hydrophobic silica. In some embodiments, the matrix former comprises gelatin. In some embodiments, the structure former comprises mannitol. In some embodiments, the pharmaceutical suspension includes a viscosity modifier. In some embodiments, the pharmaceutical suspension comprises 0.01-0.1% w/w viscosity modifier. In some embodiments, the viscosity modifier comprises xanthan gum. In some embodiments, the pharmaceutical suspension includes a sweetener. In some embodiments, the pharmaceutical suspension comprises 0.1-1% w/w sweetener. In some embodiments, the sweetener is sucralose. In some embodiments, the pharmaceutical suspension includes a flavoring agent. In some embodiments, the pharmaceutical suspension comprises 0.1-1% w/w flavoring agent. In some embodiments, the flavoring agent comprises terpene and/or terpinol.

In some embodiments, a method of preparing a pharmaceutical composition includes sieving raw API; mixing sieved raw API and a water insoluble material in a vessel; applying mechanical energy to the vessel and heating the vessel to a temperature greater than or equal to 50° C.; adding silica to the vessel while continuing to apply the mechanical energy and maintaining the temperature of the vessel to form coated API comprising at least one coating comprising water insoluble material and silica; sieving the coated API; forming a pharmaceutical suspension comprising: 30-50% w/w the coated API comprising at least one coating comprising water insoluble material and silica; 1-5% w/w a matrix former; 1-3% w/w a structure former; and a solvent; dosing the pharmaceutical suspension into a mold; and freeze drying the dosed pharmaceutical suspension in the mold to form the pharmaceutical composition.

Additional advantages will be readily apparent to those skilled in the art from the following detailed description. The examples and descriptions herein are to be regarded as illustrative in nature and not restrictive.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

BRIEF DESCRIPTION OF THE DRAWINGS

The invention will now be described, by way of example only, with reference to the accompanying drawings, in which.

DETAILED DESCRIPTION OF THE DISCLOSURE

Described herein are exemplary embodiments of methods for coating an API that can eliminate water soluble and/or water swellable materials from the coating of the API. These methods can include coating the API with a water insoluble material such as a wax. In addition, the API can be coated with a second coating material (e.g., silica) which can be in the same coating as the water insoluble material, in a second coating on top of the water insoluble material coating, or a combination thereof. The coated API can then be mixed with a matrix premix to form a pharmaceutical suspension and then freeze-dried to form a pharmaceutical composition (e.g., dosage form).

Figure 1A:
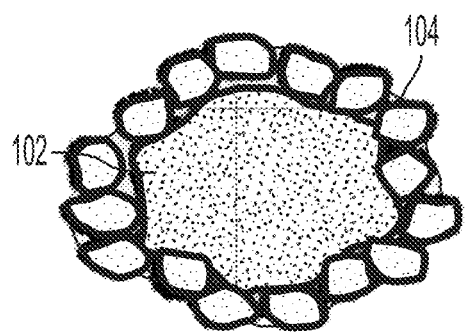
FIG. 1A shows an API particle coated with particles of a deformable coating material (i.e., a first coating layer) according to some embodiments.
Figure 1B:
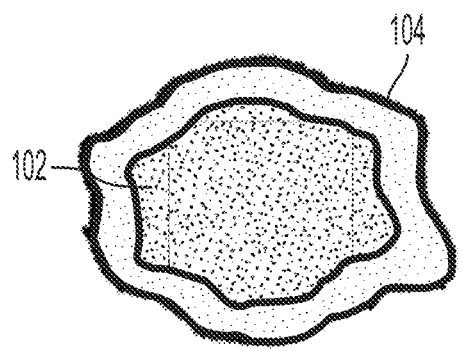
FIG. 1B shows an API particle coated with a continuous film layer of deformable coating material (i.e., a first coating layer) according to some embodiments.
Figure 1C:
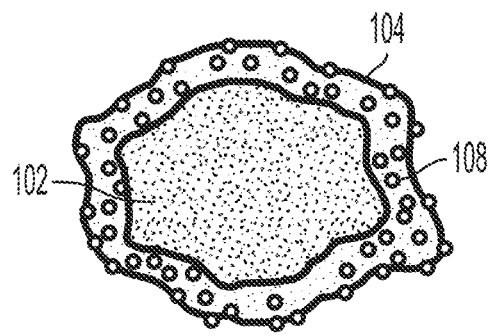
FIG. 1C shows an API particle coated with a continuous film layer of deformable coating material (i.e., a first coating layer) with particles of silica (i.e., a second coating layer) partially embedded and/or embedded on the surface of the first coating layer according to some embodiments.
Figure 17:
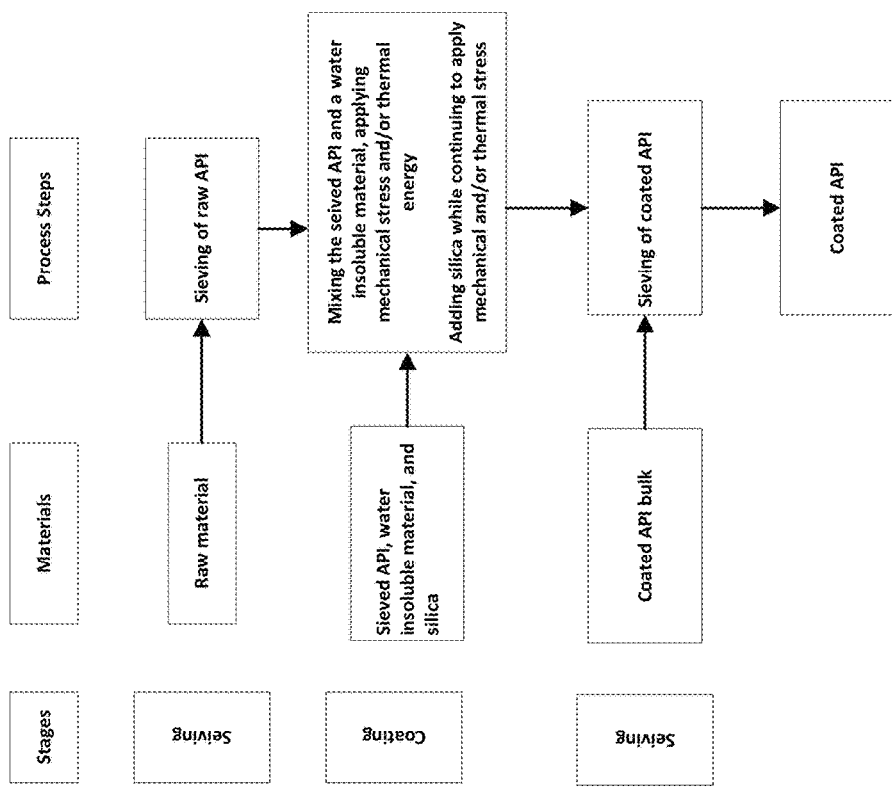
FIG. 17 illustrates an example of a flow chart of a method of producing coated API in accordance with some embodiments disclosed herein.

FIGS. 1A, 1B, and 1C illustrate different phases of a coated API particle (e.g., Ibuprofen or Acetaminophen (APAP) according to some embodiments). FIG. 17 illustrates an example of a flow diagram for coating an API particle in accordance with some embodiments described herein. In some embodiments, API particles can be combined with one or more coating materials to produce coated API. Applicants have discovered that water soluble and/or water swellable materials are not needed for the coating. As such, this coating may comprise materials including a water insoluble material.

Figure 2:
FIG. 2 shows a scanning electron microscope (SEM) image of an un-coated API particle according to some embodiments.

For example, FIG. 1A shows an API particle 102 surrounded by particles of a coating material 104. To achieve the coated API particle of FIG. 1A, the combined API (i.e., API particle 102) and one or more coating material(s) (i.e., coating material particles 104) may be exposed to mechanical and/or thermal energy to produce an ordered mixture of API particle 102 comprising a discrete layer of coating material particles 104 layering the surface of the API particle 102. API particle 102 of FIG. 1A is shown with a single layer of discrete particles of coating material(s). However, API particle 102 may have two or more discrete layers of coating particles. Additionally, FIG. 2 shows an SEM image of an un-coated API particle.

Figure 3:
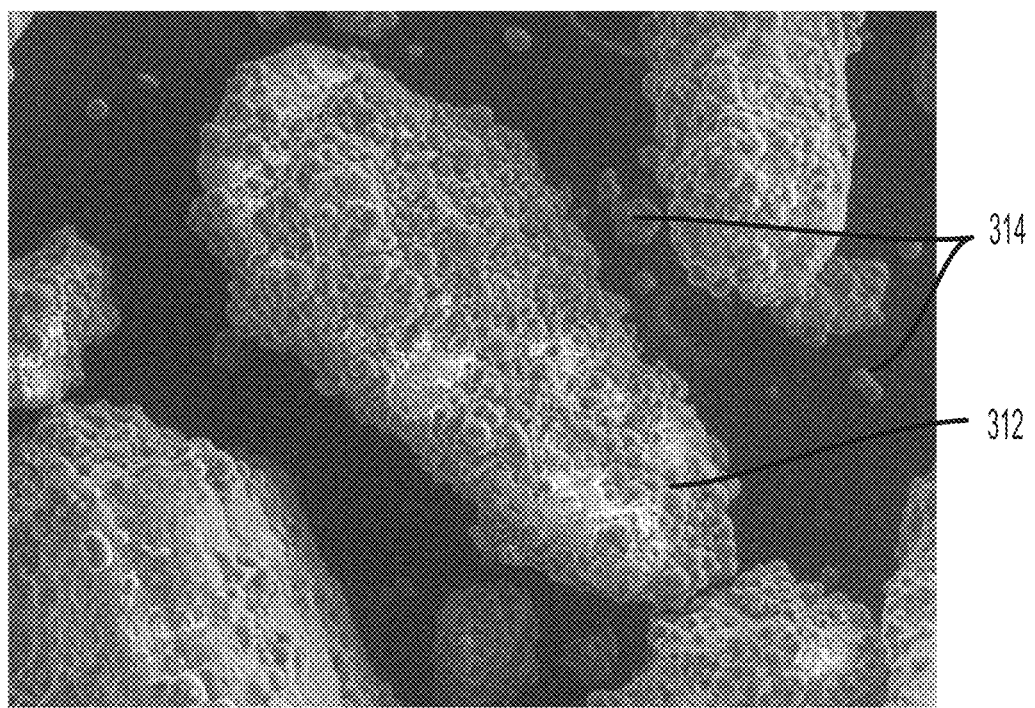
FIG. 3 shows an SEM image of a coated API particle, according to some embodiments.

FIG. 1B demonstrates API particle 102 surrounded by continuous, deformed film layer 104. Specifically, FIG. 1B shows that all of the coating material particles 104 may be deformable and may deform when subjected to mechanical stress and/or elevated temperature. Thus, because all the coating materials comprise deformable characteristics, the coating material 104 of FIG. 1B is a relatively smooth and continuous coating layer after exposure to mechanical and/or thermal energy. In some embodiments, API particle 102 may have two or more relatively smooth and continuous coating layers. "Continuous film" as used herein may be a layer surrounding an API particle formed by melting/softening or otherwise breaking down one or more deformable components of the individual coating material particles such that they comprise a single, continuous layer surrounding the API particle. FIG. 3 also provides an SEM image showing a coated API particle according to some embodiments.

In some embodiments, one or more of the coating materials may not be deformable but may be embedded in the deformable coating layer. Thus, the continuous film may comprise solid particles of the non-deformable material embedded within the deformed coating material. FIG. 1C shows that continuous film 104 may comprise solid non-deformable particles 108 of one or more non-deformable materials partially embedded and/or embedded within the deformed coating material of continuous film 104. This continuous film 104 of FIG. 1B or 1C can ensure a coating (for example, a coating that masks the taste of the API) and a delayed API release. In some embodiments, API particle 102 may have two or more continuous coating layers partially embedded and/or embedded with non-deformable coating material particles. FIG. 3 also provides an SEM image showing a functionally-coated API particle according to some embodiments.

As used herein, the terms "deformable", "deformable components", "deformable components of the coating material" and other related terms refer to one or more components of water insoluble materials that can be broken down when subjected to mechanical stress and/or elevated temperature. As explained in the Examples, the coating of the API can be accomplished without the use of water soluble or water swellable materials.

In some embodiments, the method of coating the API may include sieving of raw API, coating the API with coating materials, and sieving of the coated API as shown in FIG. 17. In some embodiments, the raw API (e.g., ibuprofen, Acetaminophen, etc.) can be sieved to an average size between 50-500 microns, 50-300 microns, or 75-250 microns. In some embodiments, the raw API can be sieved using 25, 50, 75, or 100 (bottom sieve mesh) and 150, 200, 250, 300, 400, or 500 (top sieve mesh) micron meshes and appropriate sieving equipment to obtain the desirable particle size fraction for the coating process by removal of fine and coarse material.

Any API may be used with this invention. One of ordinary skill in the art would understand that for various reasons such as stability, compatibility with other ingredients, desired drug release profile, certain active ingredients and/or APIs are more desirable for formulation into a dosage form. In some embodiments, the API may be an active pharmaceutical ingredient for the treatment of human or veterinary diseases. The API can be the component that the solid lyophilized dosage form is used to deliver. The API may be an ingredient that can be absorbed via the mucous membrane. APIs may be one or more of antibacterial agents, antifungal agents, antiprotozoal agents, antiviral agents, labor-inducing agents, spermicidal agents, prostaglandins, steroids and microbicides, proteins/peptides and vaccine antigens.

APIs may include pharmaceutical ingredients as well as other types of active ingredients that may be ingested, such as vitamins and dietary supplements. Suitable APIs include, without limitation: analgesics and anti-inflammatory agents (e.g., ibuprofen), antacids, anthelmintics, anti-arrhythmic agents, anti-bacterial agents, anti-coagulants, anti-anxiety anti-depressants, anti-diabetics, anti-diarrhoeals, anti-epileptics, anti-fungal agents, anti-gout agents, anti-hypertensive agents, anti-malarials, anti-migraine agents, anti-muscarinic agents, anti-neoplastic agents and immunosuppressants, anti-protazoal agents, anti-rheumatics, anti-thyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, lipid regulating agents, local anesthetics, neuro muscular agents, nitrates and anti-anginal agents, nutritional agents, opioid analgesics, oral vaccines, proteins, peptides and recombinant drugs, sex hormones and contraceptives, spermicides, stimulants, smoking cessation products and combinations thereof. A list of specific examples of active ingredients may be found in U.S. Pat. Nos. 5,976,577; 6,413,549; and 6,709,669 and U.S. Patent Application Publication No. 2011/0229573, all of which are incorporated herein by reference in their entirety.

The API may be a single active pharmaceutical ingredient, such as a single chemical entity, or it may be a mixture of several active pharmaceutical ingredients. The active pharmaceutical ingredient may be of any of the many categories of active pharmaceutical ingredients. The active pharmaceutical ingredient may be selected from, but is not limited to, the group consisting of acyclovir, fluconazole, progesterone and derivatives thereof, nonoxylenol-9, terbutaline, lidocaine, testosterone and derivatives, dinoprostone, lactobacillus, estrogen and derivatives, naphthalene2-sulfonate, lesmitidan, doxycycline, droxidopa, sapropterin, butoconazole, clindamycin nitrate/phosphate, neomycine sulfate, polymyxin sulfate, nystatin, clotrimazole, dextrin sulphate, glyminox, miconazole nitrate, benzalkonium chloride, sodium lauryl sulphate, tenofovir, insulin, calcitonin, danazol, ibuprofen, acetaminophen, cefpodoxime proxetil, desloratadine, dextromethorphan, diphenhydramine hydrochloride, vitamins and/or minerals, adipic acid, ascorbic acid, macrolide antibiotics, NS-AIDS, cefuroxime axetil, amobarbital, ciprofloxacin hydrochloride, sildenafil citrate, pinaverium bromide, propantheline bromide, triprolidine Hcl, dimenhydrinate, cefeanel daloxate HCl, Enoxacin, Sparfloxacin, aspirin, famotidine, amoxycilin trihydrate, morphine HCl, amiprilose HCl, terfenadine, beclamide, clarithromycin, roxithromycin, nizatidine, cetraxate HCl, ciprofloxacin, bifemelene HCl, Cefuroxime axetil, pirienzepine and/or oxyburynin, diclofenac, nicorandil, levofloxacin, acriflavine, leuprorelin acetate, metronidazole, benzydamine hydrochloride, chloramphenicol, oxybutynin, ethinyl estradiol, prostaglandins, insulin, calcitonin and combinations thereof. The active pharmaceutical ingredient may also be vaccine antigen such as those for the treatment of Hepatitis B, HIV, HPV, Chlamydia, gonococcal infections.

APIs may include salts, esters, hydrates, solvates and derivatives of any of the foregoing active ingredients. Suitable derivatives are those that are known to skilled persons to possess the same activity as the active ingredient though the activity level may be lower or higher. APIs may also include any active ingredient that is incompatible with oral delivery methods or compositions.

When present, an API is employed in the formulation in an effective amount that is necessary to provide the dosage required, typically for producing at least one physiological effect as established by clinical studies. One of ordinary skill in the art can readily determine an appropriate amount of active ingredient to include in the multi-layer dosage form made according to the present disclosure.

In some embodiments, the coated API particles or pharmaceutical composition may comprise from 30.0 to 90.0% w/w API. In some embodiments, the coated API particles or pharmaceutical composition may comprise from 40.0 to 85.0% w/w, from 50.0 to 80.0% w/w, from 65.0 to 80.0% w/w API, or from 68-78% w/w API. In some embodiments, the coated API particles or pharmaceutical composition may comprise more than 40.0% w/w, more than 50.0% w/w, more than 60.0% w/w, more than 65% w/w, more than 68% w/w, more than 70.0% w/w, more than 75.0% w/w, more than 77% w/w, more than 80.0% w/w, or more than 85.0% w/w API. In some embodiments, the coated API particles or pharmaceutical composition may comprise less than 90.0% w/w, less than 85.0% w/w, less than 80.0% w/w, less than 78% w/w, less than 75.0% w/w, less than 70.0% w/w, less than 69% w/w, less than 65% w/w, less than 60.0% w/w, less than 50.0% w/w, or less than 40.0% w/w API. In some embodiments, the coated API particles may include about 63.5-77.5% w/w API. In some embodiments, the pharmaceutical composition may include about 68.75% w/w API.

Coating 104 surrounding the API particle 102 may comprise materials including a water insoluble material. In some embodiments, this coating may coat an API particle (e.g., Ibuprofen) directly, or it may coat an API particle already comprising one or more coatings. In some embodiments, the ratio of coating material to API may be optimized to minimize excess coating material. For example, the coating material may comprise 5-85% w/w, 10-50% w/w, 15-30% w/w, 20-25% w/w, or 22.5% w/w of the API and coating material mixture. In some embodiments, the coating material may comprise less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, or less than 10% of the API and coating material mixture or pharmaceutical composition. In some embodiments, the coating material may include more than 5%, more than 10%, more than 15%, more than 20%, more than 25%, more than 30%, more than 35%, more than 40%, more than 45%, more than 50%, more than 55%, more than 60%, more than 65%, more than 70%, or more than 75% of the API and coating material mixture or pharmaceutical composition. In some embodiments, the coating material percentage may include two or more layers of coating material.

The water insoluble material of the coating materials may be a particle comprising an average particle size less than that of the API. For example, the water insoluble material(s) may comprise an average particle size from about 1-20 μm, about 1-12 μm, about 2-10 μm, about 5-12 μm, or about 5-6 μm. In some embodiments, the water insoluble material may be approximately ten times smaller than that of the API to enable ordered mixing and coating. The water insoluble material of the coating material may be deformable under mechanical stress and/or elevated temperature. The coated API or pharmaceutical composition may comprise from 5 to 70% w/w, from 10 to 60% w/w, from 10 to 50% w/w, from 10 to 40% w/w, from 10 to 35% w/w, from 15 to 30% w/w, from 15 to 25% w/w, or from 18 to 21% w/w water insoluble materials. In some embodiments, the coated API or pharmaceutical composition may comprise more than 5% w/w, more than 10% w/w, more than 15% w/w, more than 18% w/w, more than 20% w/w, more than 21% w/w, more than 25% w/w, more than 30% w/w, more than 35% w/w, or more than 40% w/w water insoluble materials. In some embodiments, the coated API or pharmaceutical composition may comprise less than 70% w/w, less than 60% w/w, less than 50% w/w, less than 45% w/w, less than 40% w/w, less than 35% w/w, less than 30% w/w water insoluble materials, less than 25% w/w, less than 22% w/w, or less than 20% w/w. In some embodiments, the coated API may include 21% w/w water insoluble materials. In some embodiments, the pharmaceutical composition may include 18.63% w/w water insoluble materials. Examples of suitable water insoluble materials include, but are not limited to ethylcellulose, polyethylene, polypropylene, polytetrafluoroethylene, carnauba wax, candelilla wax, castor wax, polyamide wax and/or synthetic wax.

Dry coating the API with silica as a second coating material to slow the dissolution rate can improve the in-vivo taste-masking performance of the coating. As discussed above, the second coating material can form a second coating on top of the water insoluble material, be a part of or embedded in the coating with the water insoluble material, or a combination thereof. The coated API (e.g., Ibuprofen) may comprise from 0.5 to 35% w/w, from 0.5 to 5 & w/w, from 0.5 to 3% w/w, or from 1 to 2% w/w silica. In some embodiments, the coated API or pharmaceutical composition can comprise from 0.5 to 20% w/w, from 0.5 to 10% w/w, from 0.5 to 5% w/w, from 0.5 to 3% w/w, or from 1 to 2% w/w silica (e.g., hydrophobic fumed silica). In some embodiments, the coated API can include about 1.5% w/w hydrophobic silica. In some embodiments, the pharmaceutical composition can include about 1.33% w/w hydrophobic silica. In some embodiments, the coated API or pharmaceutical composition can comprise more than 0.5% w/w, more than 1.0% w/w, more than 1.5% w/w, more than 2.0% w/w, more than 2.5% w/w, more than 3.0% w/w, more than 4.0% w/w, more than 5.0% w/w, more than 10% w/w, more than 15% w/w, more than 20% w/w, more than 25% w/w, or more than 30% w/w silica (e.g., hydrophobic fumed silica). In some embodiments, the coated API or pharmaceutical composition can comprise less than 35% w/w, less than 25% w/w, less than 15% w/w, less than 10% w/w, less than 5.0% w/w, less than 4.0% w/w, less than 3.5% w/w, less than 3.0% w/w, less than 2.5% w/w, less than 2.0% w/w, less than 1.5% w/w, or less than 1.0% w/w silica (e.g., hydrophobic fumed silica). Examples of silica that may be used include, but are not limited to, Aerosil R972 silica (Degussa), CAB-O-SIL EH-5 silica (Cabot), OX-50 silica (Degussa), COSM055 (Catalyst & Chemical Ind. Co. Ltd (Japan)), P-500 hydrophilic silica (Catalyst & Chemical Ind. Co. Ltd (Japan)), and TS5 silica (Cabot). Further, suitable devices that may be used to dry coat with silica include, but are not limited to, Comil (U3 Quadro Comil of Quadro Pennsylvania, U.S.), LabRAM (Resodyne Minnesota, U.S.), Magnetically Assisted Impact Coater (MAIC, Aveka Minnesota, U.S.), and Fluid Energy Mill (FEM, Qualification Micronizer of Sturtevant Massachusetts U.S.).

In some embodiments, mechanical and/or thermal energy may be used to deform the one or more water insoluble materials and/or silica onto the API during coating. For example, mechanical stress can be applied to the functionally-coated API using a PharmaRAM II acoustic mixer (i.e., acoustic energy), a RAM 5 Pharma mixer, or a RAM 55 Pharma mixer (Resodyn Mixers). The coated API may be exposed to up to 100 times the force of gravity (100 G acceleration) during this acoustic mixing process. These high forces can cause particle-particle collisions that generate energy in the form of heat, which may be used to deform the water insoluble materials or silica onto the API.

In some embodiments, the desired amounts of API and water insoluble materials can be added to a mixer and mechanical and/or thermal energy (i.e., heating) can be used to deform the water insoluble materials onto the API during coating. Next, silica (e.g., hydrophobic silica) can be added to the mixer and mechanical and/or thermal energy can continue to be applied causing the silica to be added to or on top of the API coating that includes the water insoluble materials.

In some embodiments, a mixer can be used to coat the desired particle sized fraction of pre-sieved API with water insoluble materials. The desired particle size fraction of API and water insoluble materials can be added to the mixer vessel and mechanical stress and/or thermal energy can be applied to the mixture in the vessel. The temperature of the vessel during mixing can be at least 30° C.(±2° C.), 35° C.(±2° C.), 40° C.(±2° C.), 45° C.(±2° C.), 50° C.(±2° C.), 55° C.(±2° C.), or 60° C. (±2° C.) and at most 100° C.(±2° C.), 90° C.(±2° C.), 80° C.(±2° C.), 75° C.(±2° C.), 70° C.(±2° C.), 65° C.(±2° C.), 60° C.(±2° C.), 55° C.(±2° C.), or 50° C.(±2° C.), and maintained at this set point. Silica can then be added and mixed while continuing to apply the mechanical and/or thermal stress to aid flowability and improve the handling of the coated API. In some embodiments, the coated API can be sieved to an average size between 50-500 microns, 50-300 microns, or 75-250 microns. In some embodiments, the coated API can be sieved using 25, 50, 75, or 100 (bottom sieve mesh) and 150, 200, 250, 300, 400, or 500 (top sieve mesh) micron meshes and appropriate sieving equipment to obtain the desirable particle size fraction and collected and stored for downstream dosage form manufacturing.

The coating process described above can generate "loose", or "free" coating material particles. FIG. 2 is an SEM image of an uncoated API particle. FIG. 3 is an SEM image of coated API particle 312. "Loose" or "free" coating material particles 314 are not bound to coated API particle 312.

Once sieved, the coated API can be mixed into a matrix solution/suspension to form a pharmaceutical suspension (e.g., coated API plus matrix solution/suspension) and dosed by weight into pockets of preformed blister packs to form aliquots of pharmaceutical suspension. In some embodiments, the ratio of coated API to matrix solution/suspension in the pharmaceutical suspension can be about 20-60:40-80, about 30-50:50-70, about 35-45:55-65, or about 40:60. In some embodiments, the pharmaceutical suspension (i.e., pre-freeze drying) can include about 20-60% w/w, about 30-50% w/w, about 35-45% w/w, about 38-42% w/w, or about 40% w/w coated API. In some embodiments, the pharmaceutical suspension can include at least about 20% w/w, about 25% w/w, about 30% w/w, about 35% w/w, or about 40% w/w coated API. In some embodiments, the pharmaceutical suspension can include at most about 60% w/w, about 55% w/w, about 50% w/w, about 45% w/w, or about 40% w/w. In some embodiments, the pharmaceutical suspension can include about 10-50% w/w, about 20-40% w/w, about 25-35% w/w, about 28-33% w/w, or about 31% w/w API (e.g., ibuprofen). In some embodiments, the pharmaceutical suspension can include about 1-20% w/w, about 5-15% w/w, about 5-10% w/w, or about 8.4% w/w water insoluble materials (as part of the coated API). In some embodiments, the pharmaceutical suspension can include about 0.1-5% w/w, about 0.1-3% w/w, about 0.1-1% w/w, or about 0.6% w/w silica (e.g., hydrophobic silica) (as part of the coated API).

The matrix solution/suspension may include a matrix former, a structure former, and a solvent. For example, the matrix former may include any water soluble or water dispersable material that is pharmacologically acceptable or inert to the functionally-coated API. In some embodiments, the matrix former may be a polypeptide such as gelatin. The gelatin may be at least partially hydrolyzed (by heating in water). Other suitable matrix former materials include, but are not limited to, polysaccharides such as hydrolyzed dextran, dextrin, and alginates, polyvinyl alcohol, polyvinylpyrrolidone, and/or acacia. In some embodiments, the pharmaceutical suspension include about 1-10% w/w, about 1-5% w/w, about 1-3% w/w, about 2-3% w/w, or about 2.4% w/w matrix former. In some embodiments, the amount of matrix former in a matrix solution/suspension or pharmaceutical suspension can be from about 0.1 to 10% w/w. In some embodiments, the amount of matrix former in the matrix solution/suspension or pharmaceutical suspension may include from 1.0 to 8.0% w/w or from 2.0 to 5.0% w/w. In some embodiments, the amount of matrix former in the matrix solution/suspension or pharmaceutical suspension may include more than 0.1% w/w, more than 0.5% w/w, more than 1.0% w/w, more than 2.0% w/w, more than 3.0% w/w, more than 4.0% w/w, more than 4.5% w/w, more than 5.0% w/w, or more than 8.0% w/w. In some embodiments, the amount of matrix former in the matrix solution/suspension or pharmaceutical suspension may include less than 10% w/w, less than 8.0% w/w, less than 6.0% w/w, less than 5.0% w/w, less than 4.0% w/w, less than 3.0% w/w, less than 2.5% w/w, less than 2.0% w/w, less than 1.5% w/w, or less than 1.0% w/w.

A structure former, or bulking agent, of the matrix solution/suspension may include a sugar. For example, suitable structure formers include, but are not limited to, mannitol, dextrose, lactose, galactose, glycine, cyclodextrin, or combinations thereof. The structure former can be used in freeze drying as a bulking agent as it crystallizes to provide structural robustness to the freeze-dried dosage form. In some embodiments, the amount of structure former in the matrix solution/suspension can be from about 0.1 to 10% w/w. In some embodiments, the amount of structure former in the matrix solution/suspension or pharmaceutical suspension may include from 1.0 to 8.0% w/w, from 1.0 to 5% w/w, from 1 to 3% w/w, from 1.5 to 2.0% w/w, or 1.8% w/w. In some embodiments, the amount of structure former in the matrix solution/suspension or pharmaceutical suspension may include more than 0.1% w/w, more than 0.5% w/w, more than 1.0% w/w, more than 1.5% w/w, more than 2.0% w/w, more than 3.0% w/w, more than 4.0% w/w, more than 4.0% w/w, more than 5.0% w/w, or more than 8.0% w/w. In some embodiments, the amount of structure former in the matrix solution/suspension or pharmaceutical suspension may include less than 10% w/w, less than 8.0% w/w, less than 6.0% w/w, less than 5.0% w/w, less than 4.0% w/w, less than 3.0% w/w, less than 2.5% w/w, less than 2.0% w/w, less than 1.5% w/w, or less than 1.0% w/w.

In some embodiments, a matrix solution/suspension and pharmaceutical suspension may include a viscosity modifier. For example, a viscosity modifier according to embodiments provided herein may include vegetable gums such as xanthan gum, alginin, guar gum, or locust bean gum, proteins such as collagen or gelatin, sugars such as agar, carboxymethyl cellulose, pectin, or carrageenan, starches such as arrowroot, cornstarch, katakuri starch, potato starch, sago, or tapioca, and/or other suitable viscosity modifiers. In some embodiments, the amount of viscosity modifier in the matrix solution/suspension or pharmaceutical suspension may be from 0 to 0.2% w/w, from 0.01 to 0.1% w/w, from 0.02-0.08% w/w, or about 0.05% w/w. In some embodiments, the amount of viscosity modifier in the matrix solution/suspension or pharmaceutical suspension may be greater than 0.01% w/w, greater than 0.03% w/w, greater than 0.05% w/w, greater than 0.07% w/w, greater than 0.1% w/w, greater than 0.12% w/w, greater than 0.15% w/w, or greater than 0.17% w/w. In some embodiment, the amount of viscosity modifier in the matrix solution/suspension or pharmaceutical suspension may be less than 0.2% w/w, less than 0.18% w/w, less than 0.15% w/w, less than 0.12% w/w, less than 0.1% w/w, less than 0.08% w/w, less than 0.06% w/w, or less than 0.03% w/w.

The solvent of the matrix solution/suspension and pharmaceutical suspension may be water, but the suspension solution may include a co-solvent as well. In some embodiments, the solvent can be ethanol, alcohol, isopropanol, other lower alkanols, water (e.g., purified water), or combinations thereof. For example, a suitable solvent and/or cosolvent may be an alcohol, such as tert-butyl alcohol. In some embodiments, the amount of solvent in the pharmaceutical suspension can be about 35-75% w/w, about 45-65% w/w, about 50-60% w/w, about 52-58% w/w, or about 54.9% w/w. In some embodiments, the balance remaining of the pharmaceutical suspension is the solvent (i.e., Q.S. 100%).

The matrix solution/suspension and pharmaceutical suspension may also contain additional pharmaceutically acceptable agents or excipients. Such additional pharmaceutically acceptable agents or excipients include, without limitation, sugars, inorganic salts, such as sodium chloride and aluminum silicates, modified starches, preservatives, antioxidants, viscosity enhancers, coloring agents, flavoring agents, pH modifiers, sweeteners, taste-masking agents, and combinations thereof. Suitable coloring agents can include red, black and yellow iron oxides and FD & C dyes such as FD & C Blue No. 2 and FD & C Red No. 40, and combinations thereof. Suitable flavoring agents can include mint, raspberry, licorice, orange, lemon, grapefruit, caramel, vanilla, cherry and grape flavors and combinations of these. In some embodiments, the pharmaceutical suspension includes about 0.1-5% w/w, about 0.1-3% w/w, about 0.1-1% w/w, about 0.5-0.9% w/w, or about 0.6% w/w flavoring agent. Suitable pH modifiers can include citric acid, tartaric acid, phosphoric acid, hydrochloric acid, maleic acid, sodium hydroxide (e.g., 3% w/w sodium hydroxide solution), and combinations thereof. Suitable sweeteners can include sucralose, aspartame, acesulfame K and thaumatin, and combinations thereof. In some embodiments, the pharmaceutical suspension includes about 0.1-5% w/w, about 0.1-3% w/w, about 0.1-1% w/w, about 0.1-0.5% w/w, or about 0.24% w/w sweetener. Suitable taste-masking agents can include sodium bicarbonate, ion-exchange resins, cyclodextrin inclusion compounds, adsorbates or microencapsulated actives, and combinations thereof. One of ordinary skill in the art can readily determine suitable amounts of these various additional excipients if desired.

Figure 18:
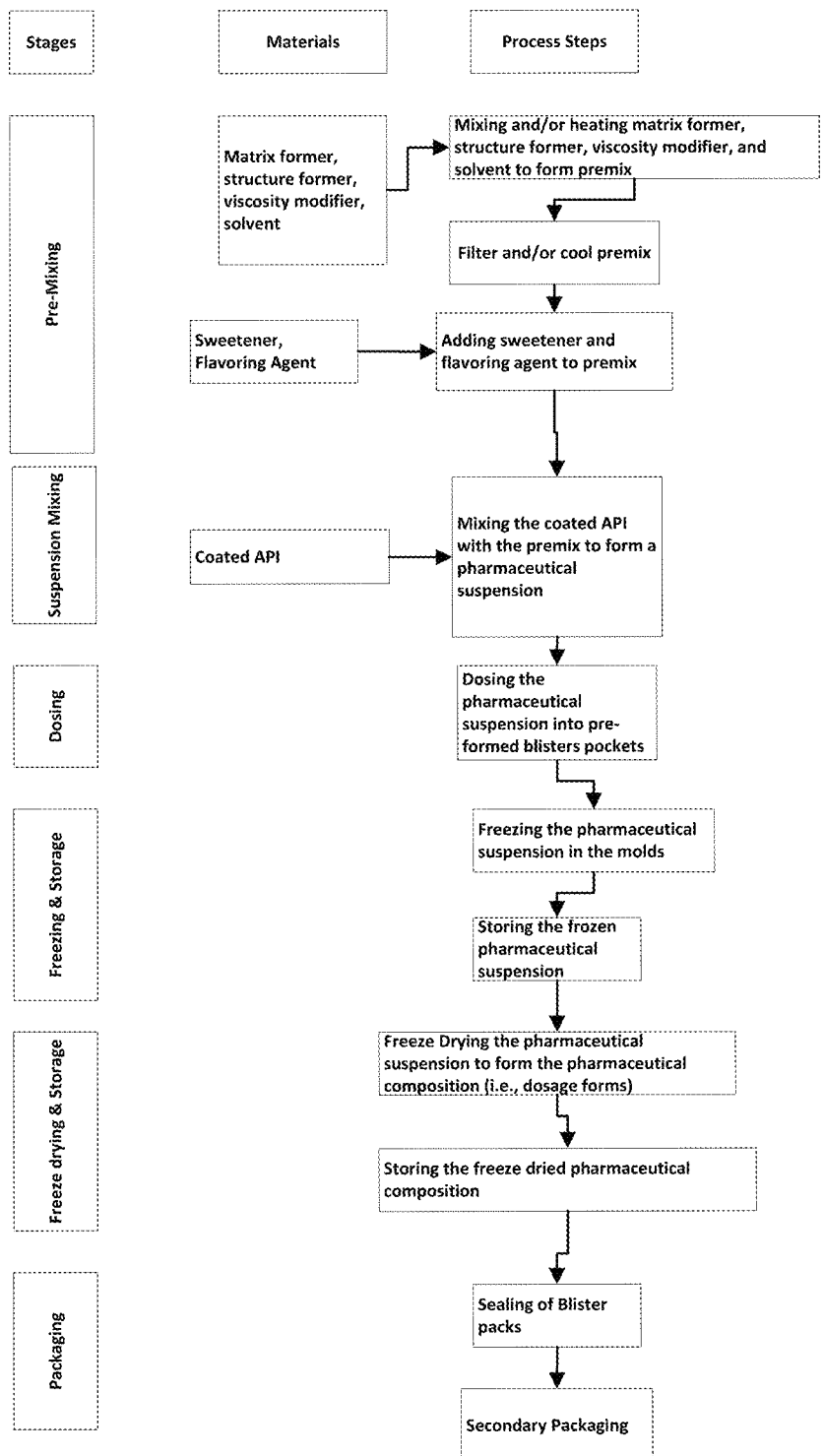
FIG. 18 illustrates an example of a flow chart of a method of producing a dosage form in accordance with some embodiments disclosed herein.
Figure 19A:
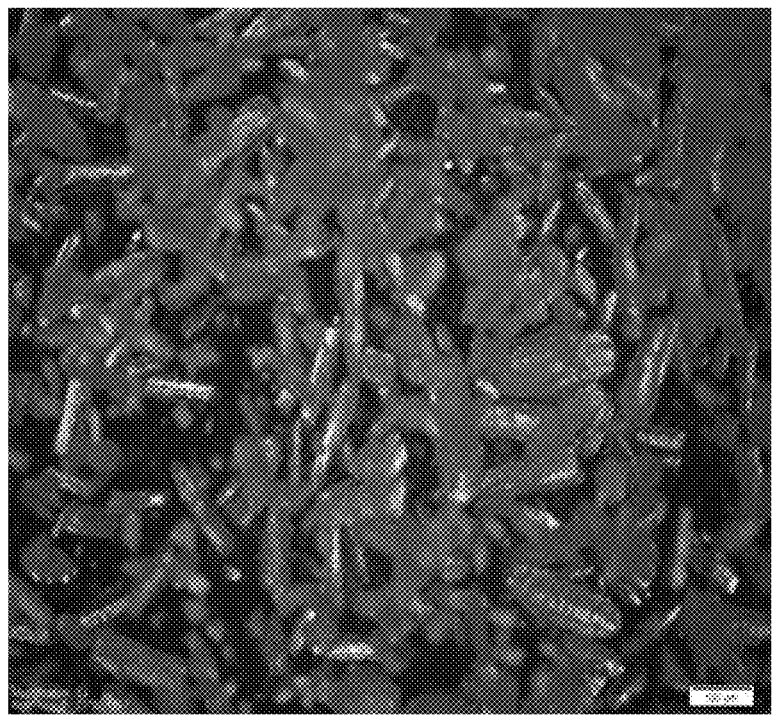
FIGS. 19A-B illustrate SEM images of sample Z3703/136/07.
Figure 19B:
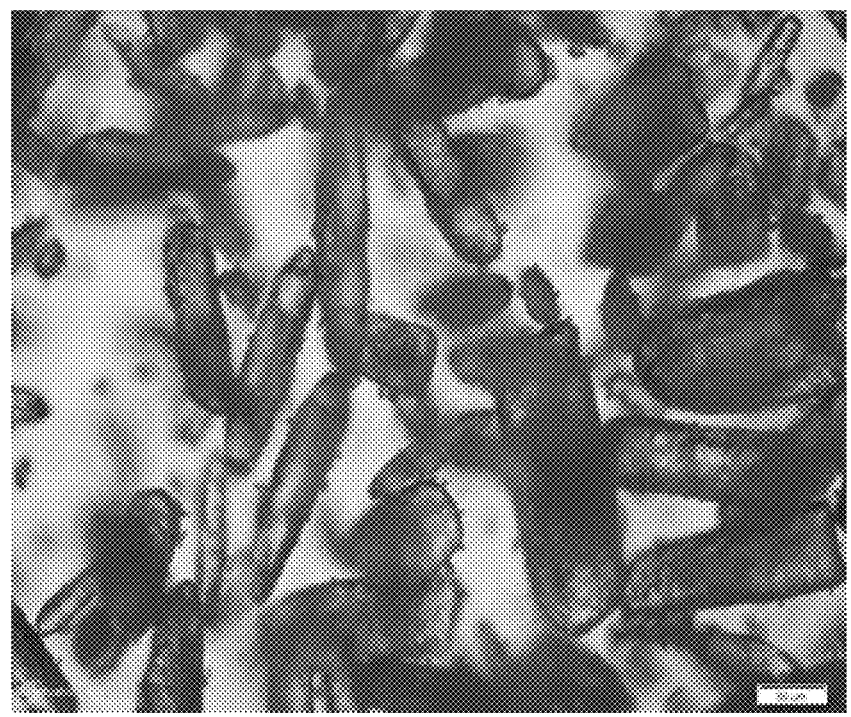
Figure 20A:
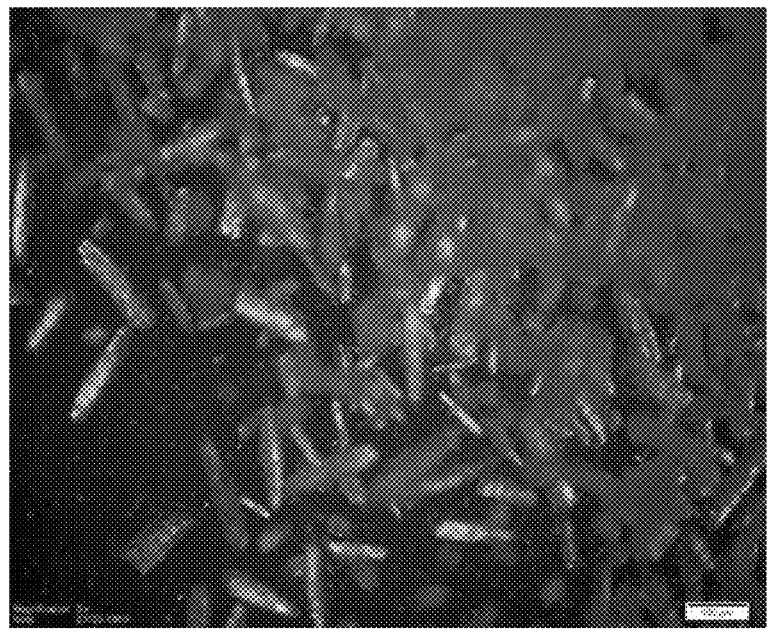
FIGS. 20A-B illustrate SEM images of sample Z3703/136/09.
Figure 20B:
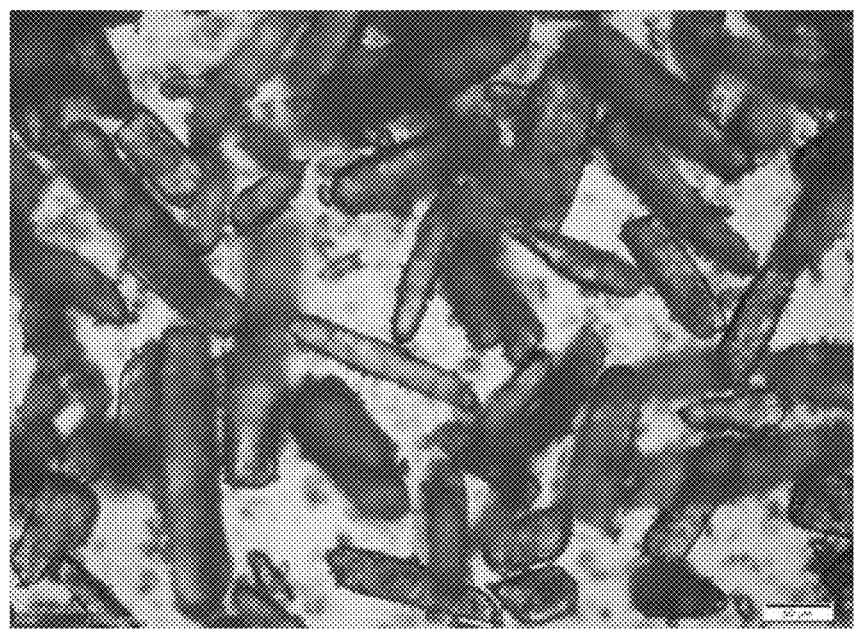
Figure 21A:
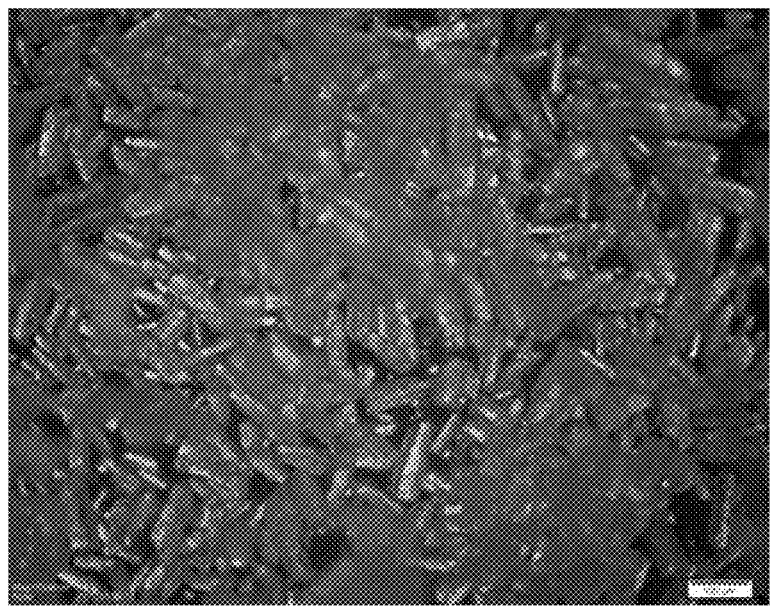
FIGS. 21A-B illustrate SEM images of sample Z3703/136/10.
Figure 21B:
Figure 22A:
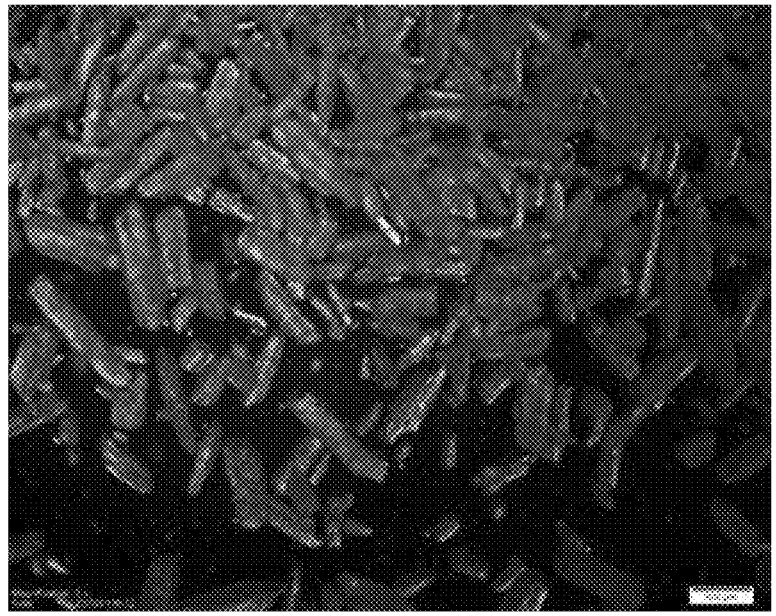
FIGS. 22A-B illustrate SEM images of sample Z3703/136/12.
Figure 22B:

FIG. 18 illustrates an example of a flow chart of a method of producing a dosage form in accordance with some embodiments disclosed herein. In some embodiments, the matrix former, structure former, viscosity modifier, and the solvent can be mixed together to form a matrix premix. The premix can be heated to about 30-90° C., 40-80° C., 50-70° C., 55-65° C., or 60° C. to reduce the microbial load. The premix can then be cooled and filtered into a suitable vessel. On completion of filtration, the premix can be cooled to at most 15° C., 20° C., 23° C., 24° C., 25° C., 26° C., 27° C., or 30° C. Next, the sweetener and flavoring agent can be added to the premix to form the matrix solution/suspension. The matrix solution/suspension can be mixed (e.g., continuously stirred) and kept at the at most 15° C., 20° C., 23° C., 24° C., 25° C., 26° C., 27° C., or 30° C.

In some embodiments, the premix and the coated API can be mixed to form a pharmaceutical suspension. Blister pockets can be filed (i.e., dosed with the pharmaceutical suspension) with a target wet dose of a specific mg amount of the pharmaceutical suspension for API dosage forms of a certain amount of API (e.g, 200 mg. 100 mg, or 50 mg). Once dosed, the blister packs with aliquots pharmaceutical suspension are frozen under sub-zero conditions. The frozen aliquots of dosed pharmaceutical suspension is held frozen until it is ready for freeze drying during which the solvent of the pharmaceutical suspension is removed to form the pharmaceutical composition. In some embodiments, after the pharmaceutical suspension has been dosed into the blister pockets, the suspension can be frozen in a freezing tunnel. The temperature of the tunnel and time the suspension remains in the tunnel can be controlled to ensure that all units manufactured are adequately frozen. After freezing, the frozen product can be stored in freezers that are temperature controlled and monitored to ensure that the units remain frozen throughout the frozen storage period.

After the pharmaceutical suspension has been frozen, the frozen suspension can be freeze-dried. The freeze-drying process can remove the frozen water rapidly by sublimation under vacuum at low pressure to form solid dosage forms (i.e., pharmaceutical composition). Once dried, the dosage forms can be transferred to dry storage cabinets and held in a temperature and humidity controlled environment while in-process testing is conducted for inspection for product defects and tablet weights. On completion of the in-process tests, the dried dosage forms can be transferred to the sealing line for application of a lidding foil over the blister packs.

In some embodiments, a pharmaceutical composition (also known as a dosage form) may be prepared by dosing the pharmaceutical suspension into preformed blister packs. In some embodiments, a freeze-dried orally disintegrating tablet may be prepared by dosing the suspension into blister packs. In some embodiments, dosing pumps pump by volume, but the process is controlled by weight. Thus, to ensure content uniformity from one dosage form to the next, the dosing process may be controlled such that the volume-to-weight percentage of dosed suspension is consistent. For example, a volume-to-weight percentage may be consistent within 10 percent, within 8 percent, within 6 percent, within 5 percent, within 4 percent, within 3 percent, within 2 percent, within 1.5 percent, within 1 percent, within 0.5 percent, or within 0.25 percent. In some embodiments, the weight of the dosed pharmaceutical suspension is within 10 percent, within 8 percent, within 6 percent, within 5 percent, within 4 percent, within 2.5 percent, within 2 percent, within 1.5 percent, within 1 percent, within 0.5 percent, or within 0.25 percent of a target weight. Additionally, the viscosity of the pharmaceutical suspension should be kept low enough for ease of dosing. As described above, a high viscosity of the pharmaceutical suspension can cause pump seizures during dosing.

In some embodiments, the amount of coated API in a pharmaceutical composition (e.g., an orally disintegrating tablet or dosage form) may be about 50-99% w/w, about 70-99% w/w, about 80-95% w/w, about 85-95% w/w, about 85-90% w/w, or about 88.71% w/w. In some embodiments, the amount of coated API in the pharmaceutical composition may be less than 99% w/w, less than 95% w/w, less than 93% w/w, less than 90% w/w, less than 89% w/w, less than 85% w/w, or less than 80% w/w. In some embodiments, the amount of coated API in the pharmaceutical composition may be more than 50% w/w, more than 60% w/w, more than 70% w/w, more than 80% w/w, more than 85% w/w, more than 86% w/w, more than 87% w/w, more than 88% w/w, or more than 90% w/w.

In some embodiments, the amount of API in a pharmaceutical composition may be about 50-90% w/w, about 60-80% w/w, about 65-75% w/w, about 65-70% w/w, or about 68.75% w/w. In some embodiments, the amount of API in the pharmaceutical composition may be less than 90% w/w, less than 85% w/w, less than 80% w/w, less than 75% w/w, less than 70% w/w, less than 69% w/w, or less than 65% w/w. In some embodiments, the amount of API in the pharmaceutical composition may be more than 50% w/w, more than 55% w/w, more than 60% w/w, more than 62% w/w, more than 63% w/w, more than 65% w/w, more than 66% w/w, more than 68% w/w, or more than 70% w/w.

In some embodiments, the amount of water insoluble materials in the pharmaceutical composition may be about 1-40% w/w, about 10-30% w/w, about 15-25% w/w, about 15-20% w/w, or about 18.63% w/w. In some embodiments, the amount of water insoluble materials in the pharmaceutical composition may be less than 40% w/w, less than 35% w/w, less than 30% w/w, less than 25% w/w, less than 22% w/w, less than 20% w/w, or less than 19% w/w. In some embodiments, the amount of water insoluble materials in the pharmaceutical composition may be more than 1% w/w, more than 5% w/w, more than 8% w/w, more than 10% w/w, more than 12% w/w, more than 15% w/w, more than 16% w/w, more than 17% w/w, or more than 18% w/w.

In some embodiments, the amount of silica in the pharmaceutical composition may be about 0.1-5% w/w, about 0.5-3% w/w, about 1-3% w/w, about 1-2% w/w, about 1-1.5% w/w, or about 1.33% w/w. In some embodiments, the amount of silica in the pharmaceutical composition may be less than 5% w/w, less than 4% w/w, less than 3% w/w, less than 2% w/w, less than 1.8% w/w, less than 1.6% w/w, or less than 1.5% w/w. In some embodiments, the amount of silica in the pharmaceutical composition may be more than 0.01% w/w, more than 0.05% w/w, more than 0.1% w/w, more than 0.5% w/w, more than 0.75% w/w, more than 0.8% w/w, more than 1% w/w, more than 1.2% w/w, or more than 1.3% w/w.

In some embodiments, the amount of matrix former in the pharmaceutical composition may be about 1-15% w/w, about 1-10% w/w, about 2-8% w/w, about 3-7% w/w, about 4-6% w/w, about 5-6% w/w, or about 5.32% w/w. In some embodiments, the amount of matrix former in the pharmaceutical composition may be less than 20% w/w, less than 15% w/w, less than 12% w/w, less than 10% w/w, less than 8% w/w, less than 7% w/w, or less than 6% w/w. In some embodiments, the amount of matrix former in the pharmaceutical composition may be more than 1% w/w, more than 2% w/w, more than 3% w/w, more than 4% w/w, more than 5% w/w, or more than 5.1% w/w.

In some embodiments, the amount of structure former in the pharmaceutical composition may be about 1-15% w/w, about 1-10% w/w, about 2-8% w/w, about 2-6% w/w, about 3-7% w/w, about 3-6% w/w, about 3-5% w/w, or about 4% w/w. In some embodiments, the amount of structure former in the pharmaceutical composition may be less than 20% w/w, less than 15% w/w, less than 12% w/w, less than 10% w/w, less than 8% w/w, less than 7% w/w, or less than 5% w/w. In some embodiments, the amount of structure former in the pharmaceutical composition may be more than 1% w/w, more than 2% w/w, more than 2.5% w/w, more than 3% w/w, more than 3.5% w/w, or more than 4% w/w.

In some embodiments, the amount of viscosity modifier in the pharmaceutical composition may be about 0.01-1% w/w, about 0.01-0.5% w/w, about 0.05-0.5% w/w, about 0.08-0.3% w/w, or about 0.11% w/w. In some embodiments, the amount of viscosity modifier in the pharmaceutical composition may be less than 1% w/w, less than 0.8% w/w, less than 0.5% w/w, less than 0.3% w/w, less than 0.2% w/w, less than 0.15% w/w, or less than 0.12% w/w. In some embodiments, the amount of viscosity modifier in the pharmaceutical composition may be more than 0.01% w/w, more than 0.03% w/w, more than 0.05% w/w, more than 0.08% w/w, more than 0.09% w/w, or more than 0.1% w/w.

In some embodiments, the amount of flavoring agent in the pharmaceutical composition may be about 0.01-2% w/w, about 0.01-1% w/w, about 0.1-1% w/w, about 0.3-0.8% w/w, or about 0.53% w/w. In some embodiments, the amount of flavoring agent in the pharmaceutical composition may be less than 2% w/w, less than 1% w/w, less than 0.9% w/w, less than 0.8% w/w, less than 0.7% w/w, less than 0.6% w/w, or less than 0.5% w/w. In some embodiments, the amount of flavoring agent in the pharmaceutical composition may be more than 0.01% w/w, more than 0.5% w/w, more than 0.1% w/w, more than 0.2% w/w, more than 0.3% w/w, or more than 0.4% w/w.

In some embodiments, the amount of sweetener in the pharmaceutical composition may be about 0.1-5% w/w, about 0.5-3% w/w, about 1-3% w/w, about 1-2% w/w, about 1-1.5% w/w, or about 1.33% w/w. In some embodiments, the amount of sweetener in the pharmaceutical composition may be less than 5% w/w, less than 4% w/w, less than 3% w/w, less than 2% w/w, less than 1.8% w/w, less than 1.6% w/w, or less than 1.5% w/w. In some embodiments, the amount of sweetener in the pharmaceutical composition may be more than 0.01% w/w, more than 0.05% w/w, more than 0.1% w/w, more than 0.5% w/w, more than 0.75% w/w, more than 0.8% w/w, more than 1% w/w, more than 1.2% w/w, or more than 1.3% w/w.

Minimizing and/or Preventing the Agglomeration of the Coating Material of Coated API Described below are methods for preparing pharmaceutical compositions comprising API that minimize the amount of excess coating material and/or the amount of agglomeration of excess coating material on storage.

Methods according to some embodiments include removing excess coating material particles to minimize and/or to prevent agglomeration of coating material in a pharmaceutical product. In some embodiments, methods may include sieving the raw API and/or the coated API. Specifically, methods provided may include sieving the API and/or the coated API to remove any undesired particles, such as excess coating material particles. Sieving processes according to embodiments disclosed may help prevent and/or minimize the potential of coating material agglomeration that can adversely affect a disintegration time and/or a dissolution rate of the final product. Methods may also include optimizing the coating and/or dosing ratios of the process.

Methods for minimizing and or preventing agglomeration of coating material particles according to embodiments described herein may be applied to dry, solventless mixing processes for coating API. Accordingly, methods provided are described below in context of one or more dry, solventless mixing processes for coating API. However, other variations of coating/encapsulating processes may be used as well. For example, sugar coating, film coating, other variations of microencapsulation, compression coating, other variations of dry coating, melting coating, dip coating, rotary die coating, electrostatic coating, and/or other suitable types of coating may be used.

Generally, a solventless mixing process for coating API includes mixing coating materials with API to produce coated API. The coated API are then stressed mechanically and/or thermally to deform the deformable coating material, creating a continuous film surrounding the API. The coated API are then mixed with a matrix solution/suspension to form the pharmaceutical suspension. The pharmaceutical suspension comprising the coated API can be dosed into preformed molds, such as blister packs, and further treated to produce a dispensable pharmaceutical composition (e.g., a lyophilizate, a wafer, a tablet, etc.).

However, when the final product (i.e., pharmaceutical composition) is stored, any excess coating material particles not bound to coated API can agglomerate. The amount and/or severity of agglomeration may increase over time. Agglomeration of excess coating material can increase the disintegration times and/or decrease the dissolution rate of the pharmaceutical product and adversely affect any functional properties of the coating material. An increased disintegration time may also cause unacceptable dispersion and mouthfeel characteristics in vivo.

Accordingly, it has been discovered that by sieving the coated API, excess coating material can be removed, thus minimizing the amount of agglomeration of excess coating material upon storage. Further, some embodiments include optimizing the coating ratio (amount of coating materials to the amount of uncoated API) and optimizing the dosing ratio (amount of coated API to the aqueous solution matrix comprising all the other inactive ingredients) can also minimize the agglomeration of excess coating material particles.

Embodiments provided herein can be applied to coated API produced using dry, solventless processes. Some mixing processes according to embodiments described herein include coating API with a taste-masking coating. Such coatings can control the disintegration time and/or the dissolution rate of an orodispersible pharmaceutical composition such that the release of the API upon oral administration is delayed or significantly reduced during the first few minutes when it is in the mouth, yet a satisfactory amount of the API is released within 30 minutes from oral administration post swallowing. (For example, a satisfactory amount of API may be 90% of the API amount which would be released without the coating). U.S. Pat. No. 9,107,851 (the '851 patent) is directed to an example dry, solventless process for coating pharmaceutical ingredients, the entirety of which is incorporated herein.

However, other variations of coating/encapsulating processes may be used as well. For example, sugar coating, film coating, other variations of microencapsulation, compression coating, other variations of dry coating, melting coating, dip coating, rotary die coating, electrostatic coating, and/or other suitable types of coating may be used.

Additionally, specific data as provided herein is related to disintegration times. Disintegration time may be measured according to methods set forth by the United States Pharmacopeia (Disintegration 701). In some embodiments, the disintegration time may be from 2-30 seconds or 5-20 seconds. In some embodiments, the disintegration time may be less than 30 seconds, less than 25 seconds, less than 20 seconds, less than 15 seconds, less than 10 seconds, or less than 5 seconds. In some embodiments, the disintegration time may be greater than 2 seconds, greater than 5 seconds, greater than 10 seconds, greater than 15 seconds, greater than 20 seconds, or greater than 25 seconds. Similarly, dissolution rate may also be tested according to methods set forth by the United States Pharmacopeia (Dissolution 711).

In some embodiments, raw API may be sieved prior to the coating process to achieve a narrower particle size range. For example, the raw API may be sieved to remove oversized particles and/or to remove undersized particles. In some embodiments, more than one mesh can be used to remove certain particles. For example, a sieving device may comprise a series of two or more meshes to remove particles of a certain size according to the size of the mesh(s). The sieve can incorporate a vacuum transfer system to transport the particles through the series of meshes of the device. Additionally, ultrasonic probes may be incorporated into the sieving device to improve material flow and minimize blinding of the mesh during processing.

In some embodiments, the raw API can be sieved using a mesh size from 30 µm to 500 µm, from 50 µm to 450 µm, from 100 µm to 400 µm, from 150 µm to 350 µm, or from 200 µm to 300 µm. In some embodiments, the raw API can be sieved using a mesh size less than 500 µm, less than 450 µm, less than 400 µm, less than 350 µm, less than 300 µm, less than 250 µm, less than 200 µm, less than 150, or less than 100 µm. In some embodiments, the raw API can be sieved using a mesh size greater than 30 µm, greater than 50 µm, greater than 100 µm, greater than 150 µm, greater than 200 µm, greater than 250 µm, greater than 300 µm, greater than 350 µm, or greater than 400 µm.

Once the API have been coated by the coating material to produce coated API, the coated API may be sieved to remove excess coating material and residual fine API, either uncoated, partially coated or coated. Excess coating material may include any coating material particles not bound to a coated API. Upon storage of the final pharmaceutical product, any excess coating material can agglomerate. For example, fusion may occur between excess coating particles and coating particles that are already bound to an API, preventing ingress of media that would otherwise aid in disintegration of the unit or tablet or dissolution of the coated API. Accordingly, agglomeration of excess coating material can cause increased disintegration times and/or decreased dissolution rates upon administration.

However, it has been determined that methods of sieving excess coating material from the coated API can minimize agglomeration of the coating material and maintain the initial disintegration time and/or dissolution rate of the final product. The sieving process can be either batch or continuous. Additionally, this sieving process may be performed in addition to or in lieu of the sieving process performed on raw API, described above. In some embodiments, the sieving process parameters may be different between the uncoated, raw API and the coated API.

In some embodiments, coated API may be sieved to remove coating material particles having an average particle size less than a desired average coated API particle size. In some embodiments, more than one mesh can be used to remove certain particles. For example, a sieving device may comprise a series of two or more meshes to remove particles of a certain size according to the size of the mesh(s). The sieve can incorporate a vacuum transfer system to deliver the particles to the series of meshes of the device. Additionally, ultrasonic probes may be incorporated into the sieving device to improve material flow and minimize blinding of the mesh during processing. A flow aid (e.g., silica) may be included to promote movement through the sieve. For example, the coating material used to coat the API may comprise a flow aid. Conversely, raw API may not be cohesive and not require the assistance of a flow aid during sieving. The sieving process may be a batch process or a continuous process.

In some embodiments, the raw API can be sieved using a mesh size from 30 µm to 500 µm, from 50 µm to 450 µm, from 100 µm to 400 µm, from 150 µm to 350 µm, or from 200 µm to 300 µm. In some embodiments, the raw API can be sieved using a mesh size less than 500 µm, less than 450 µm, less than 400 µm, less than 350 µm, less than 300 µm, less than 250 µm, less than 200 µm, less than 150, or less than 100 µm. In some embodiments, the raw API can be sieved using a mesh size greater than 30 µm, greater than 50 µm, greater than 100 µm, greater than 150 µm, greater than 200 µm, greater than 250 µm, greater than 300 µm, greater than 350 µm, or greater than 400 µm.

The coating ratio (i.e., the amount of coating materials to the amount of uncoated API) may be optimized to minimize and/or prevent the agglomeration of the excess coating materials. For example, in some embodiments, the coating ratio can ranges from 5-85% w/w, 10-50% w/w, 10-40% w/w, 15-40% w/w, 20-40% w/w, 22.5-36.5% w/w, 15-25% w/w, 20-25% w/w, or 22.5% w/w coating materials to 15-95% w/w, 50-90% w/w, 60-90% w/w, 60-85% w/w, 60-80% w/w, 63.5-77.5% w/w, 70-85% w/w, 75-85% w/w, 75-80% w/w, or 77.5% w/w uncoated API. In some embodiments, the amount of coating materials in the coated API may be less than 80% w/w, less than 70% w/w, less than 60% w/w, less than 50% w/w, less than 40% w/w, less than 35% w/w, less than 30% w/w, less than 25% w/w, less than 20% w/w, or less than 10% w/w. In some embodiments, the amount of coating materials in the coated API may be more than 5% w/w, more than 10% w/w, more than 15% w/w, more than 20% w/w, more than 30% w/w, more than 35% w/w, more than 40% w/w, more than 50% w/w, more than 60% w/w, or more than 70% w/w. In some embodiments, the amount of uncoated API in the coated API may be less than 95% w/w, less than 85% w/w, less than 80% w/w, less than 75% w/w, less than 70% w/w, less than 65% w/w, less than 55% w/w, less than 45% w/w, less than 35% w/w, or less than 25% w/w. In some embodiments, the amount of uncoated API in the coated API may be more than 20% w/w, more than 30% w/w, more than 40% w/w, more than 50% w/w, more than 60% w/w, more than 65% w/w, more than 70% w/w, more than 75% w/w, more than 80% w/w, or more than 90% w/w.

The dosing ratio (i.e., the amount of coated API to the amount of matrix solution/suspension comprising all the inactive ingredients) may be optimized to minimize and/or prevent the agglomeration of the excess coating materials. For example, in some embodiments, the dosing ratio can range from 5-60% w/w, 20-60% w/w, 30-50% w/w, 35-45% w/w, or 40% coated API to 40-95% w/w, 40-80% w/w, 50-70% w/w, 55-65% w/w, or 60% w/w matrix solution/suspension. In some embodiments, the dosing ratio may include less than 60% w/w, less than 50% w/w, less than 45% w/w, less than 40% w/w, less than 30% w/w, less than 20% w/w, or less than 10% w/w coated API. In some embodiments, the dosing ratio may include more than 5% w/w, more than 10% w/w, more than 20% w/w, more than 30% w/w, more than 35% w/w, more than 40% w/w, or more than 50% w/w coated API. In some embodiments, the dosing ratio may include less than 95% w/w, less than 90% w/w, less than 80% w/w, less than 70% w/w, less than 65% w/w, less than 60% w/w, or less than 50% w/w matrix solution/suspension. In some embodiments, the dosing ration may

Preserving Functionally-Coated API Produced by a Dry, Solventless Mixing Process and Mixed in a Suspension Pharmaceutical compositions and methods for preparing pharmaceutical compositions provided herein may include adding hydrophobic fumed silica during the coating process to provide a protective layer surrounding and/or partially or fully embedded into a functional (or "first coating") of the functionally-coated API. The addition of this hydrophobic fumed silica layer (or "second layer") can provide a protective layer to a first coating layer of functionally-coated API and can minimize erosion of the first coating layer from shear forces necessary to mix the functionally-coated API into pharmaceutical suspension.

Generally, a solventless mixing process for coating API includes mixing coating materials with API to produce functionally-coated API. The functionally-coated API are then stressed mechanically and/or thermally to deform the deformable coating material, creating a continuous film surrounding the API. The functionally-coated API are then mixed with a matrix solution or suspension to form the pharmaceutical suspension. The pharmaceutical suspension comprising the functionally-coated API can be dosed into preformed molds, such as blister packs, and further treated to produce a dispensable pharmaceutical composition (e.g., a lyophilizate, a wafer, a tablet, etc.). In some embodiments, the dispensable pharmaceutical composition may be an orodispersible product. Ideally, a minimal amount, if any, of the API of the final dispensable pharmaceutical composition dissolves within the first few minutes of oral administration. This delay, or substantial reduction of API release, allows for the taste of the API to be masked when the orodispersible product is in a patient's mouth. Instead, the API can release once the pharmaceutical composition has passed to the gastrointestinal tract.

However, when the functionally-coated API are mixed into a matrix solution/suspension, the shear forces required to mix the particles into the matrix solution/suspension can erode the functional coating of the API. Erosion of the coating can destroy or damage the properties of the functional coating. For example, erosion of the functional coating can destroy or damage any taste-masking properties of the functional coating and allow the API to undergo dissolution in the oral cavity.

Accordingly, it has been discovered that hydrophobic fumed silica, as well as being used as a flow aid for the functionally-coated API to aid downstream processing, may also be used to provide a hydrophobic barrier layer surrounding and/or partially or fully embedded into the initial coating of the functionally-coated API. Specifically, the hydrophobic barrier layer formed by the hydrophobic fumed silica can protect one or more underlying coatings of the functionally-coated API during preparation of the pharmaceutical suspension and other downstream processing of the functionally-coated API. Thus, API according to some embodiments described herein may have a first, functional coating and a second, protective coating. In some embodiments, the first coating material and the second coating material can be mixed with the API (e.g., Ibuprofen) at the same time or one after another and then a mechanical stress and/or thermal energy can be applied to form the coating layers. In some embodiments, the first coating material is mixed with the API and mechanical stress and/or thermal energy is applied, and then the second coating material is added while continuing to apply the mechanical stress and/or thermal energy. In some embodiments, the coating layers can be one on top of the other or they can be one layer with both coating materials or a combination thereof.

Some pharmaceutical compositions and methods of preparing pharmaceutical compositions provided herein may include more than a first coating and a second coating. For example, some pharmaceutical compositions and methods of preparing the same may include three, four, five, six, or more coatings. Thus, the terms "first coating" and "second coating" as used herein should not be construed narrowly. In some embodiments, the term "first coating" can refer to a functional coating of API, and "second coating" can refer to a protective coating comprising silica. In some embodiments, functionally-coated API may have one or more coating layers between a "first coating" and a "second coating". In some embodiments, functionally-coated API may have one or more coating layers between the API and the "first coating". In some embodiments, a functionally-coated API may have one or more coating layers on top of a "second coating".

Once the functionally-coated API are prepared, they can be mixed into the matrix/suspension solution to form a pharmaceutical suspension for dosing. Mixing functionally-coated API into a matrix solution/suspension can erode the functional coating of the functionally-coated API. In some embodiments, to minimize this erosion, hydrophobic fumed silica can be used to form a second coating layer surrounding and/or partially embedded and/or embedded into the functionally-coated layer of the coated API.

However, coating functionally-coated API (i.e., API comprising at least a first coating, as described above) that will later be mixed into a matrix solution/suspension with hydrophobic fumed silica is not naturally intuitive. As described above, to create an orodispersible pharmaceutical composition according to embodiments described herein, the functionally-coated API are mixed into a matrix solution/suspension comprising a matrix former, a structure former, and a solvent (often water) to form a pharmaceutical suspension. However, a hydrophobic material is naturally resistant to mixing into a matrix solution/suspension. Accordingly, one might assume that hydrophobic fumed silica would increase the interfacial tension between the functionally-coated API and the matrix solution/suspension, increasing the difficulty of incorporating the functionally-coated API into the matrix solution/suspension and potentially causing phase separation of the pharmaceutical suspension.

Interestingly, it has been determined that hydrophobic fumed silica can be used to coat functionally-coated API comprising to preserve the first, functional coating without substantially interfering with the incorporation of the functionally-coated API into the matrix solution/suspension. As described above, a hydrophobic material in a matrix solution/suspension, such as the functionally-coated API covered with the hydrophobic fumed silica in the matrix solution/suspension described above, characteristically exhibits a relatively high surface tension between the hydrophobic material and the matrix solution/suspension. Accordingly, the surface tension between the hydrophobic functionally-coated API and the matrix solution/suspension is likely relatively high as well.

However, as discussed below, the matrix solution/suspension may comprise a matrix former such as gelatin. Some matrix formers, including gelatin, are mild surfactants, meaning that they can lower the surface tension between two materials. Accordingly, it is believed that matrix formers exhibiting surfactant-like behaviors can reduce the surface tension between the functionally-coated API and the matrix solution/suspension, which in turn allows for incorporation of the functionally-coated API into the matrix solution/suspension, while at the same time maintaining the protective properties of the hydrophobic fumed silica coating layer with respect to the first, functional coating of the functionally-coated API. This second coating layer comprising hydrophobic fumed silica can provide a hydrophobic barrier to the underlying first coating of the functionally-coated API, to protect the underlying first coating from the shear forces required to mix the functionally-coated API into a pharmaceutical suspension. By coating the functionally-coated API with a hydrophobic barrier comprising hydrophobic fumed silica, the underlying (first) coating may be protected from erosion. Further, using hydrophobic fumed silica according to described methods can prevent the matrix solution/suspension from penetrating through the coating to the API.

Under normal processing conditions, without a hydrophobic fumed silica coating layer, the coating of the functionally-coated API can erode over time under the shear forces required to mix the functionally-coated API into the matrix solution/suspension. However, there can be a "processing window" of two or more hours from the time the functionally-coated API are first mixed into the matrix solution/suspension wherein the coating can remain intact and its functionality can remain uncompromised. The exact time of this "processing window" varies and can depend upon the composition of the various components of the functionally-coated API, the composition of the matrix solution/suspension, the amount of material used to prepare the coating of the functionally-coated API, and/or the physicochemical properties of the API. However, with functionally-coated API having a second coating comprising fumed silica, this "processing window" can be extended.

In some embodiments, the pharmaceutical composition or the coated API can comprise from 0.5 to 35% w/w hydrophobic fumed silica. In some embodiments, the pharmaceutical composition or the coated API can comprise from 0.5 to 20% w/w, from 0.5 to 10% w/w, or from 0.5 to 5% w/w hydrophobic fumed silica. In some embodiments, the pharmaceutical composition or the coated API can comprise more than 0.5% w/w, more than 1.0% w/w, more than 1.5% w/w, more than 2.0% w/w, more than 2.5% w/w, more than 3.0% w/w, more than 4.0% w/w, more than 5.0% w/w, more than 10% w/w, more than 15% w/w, more than 20% w/w, more than 25% w/w, or more than 30% w/w hydrophobic fumed silica. In some embodiments, the pharmaceutical composition or the coated API can comprise less than 35% w/w, less than 25% w/w, less than 15% w/w, less than 10% w/w, less than 5.0% w/w, less than 4.0% w/w, less than 3.5% w/w, less than 3.0% w/w, less than 2.5% w/w, less than 2.0% w/w, less than 1.5% w/w, or less than 1.0% w/w hydrophobic fumed silica. The hydrophobic fumed silica may be any of Aerosil R972 silica (Degussa), CAB-O-SIL EH-5 silica (Cabot), OX-50 silica (Degussa), COSM055 (Catalyst & Chemical Ind. Co. Ltd (Japan)), TS5 silica (Cabot), and/or other suitable types of silica.

The effectiveness of the hydrophobic fumed silica-comprising protective layer can be determined by measuring the particle size of the functionally-coated API in the pharmaceutical suspension over time. The particle size of the coated API can be measured using a particle size and shape analyzer. If the hydrophobic fumed silica is effective at preserving the coating, the particle size of the functionally-coated API can remain constant or decrease very little over time. If ineffective, the particle size of the functionally-coated API can decrease more substantially over time. The particle size of the functionally-coated particles can be measured using laser diffraction, a particle analyzer such as a Malvern Mastersizer, or any other suitable means for analyzing fine particles.

The effectiveness of the hydrophobic fumed silica-comprising protective layer can also be determined by conducting dissolution testing on the functionally-coated API. If the hydrophobic fumed silica is effective at preserving the coating, the release amount (e.g., percent of release) of the functionally-coated API over time will be slower in dissolution testing. If ineffective, the release amount of the functionally-coated API over time will be greater. The release amount of the functionally-coated particles can be measured using dissolution testing, a spectrophotometric analyzer such as a Pion MicroDISS Profiler, or any other suitable means for conducting dissolution testing. In such cases, the dissolution of the functionally coated API can be equal or less than 70% after 15 minutes.

Minimizing the Aeration of Suspensions Comprising API

Embodiments provided herein may include adding a chemical compound comprising terpene and/or terpinol to the matrix solution/suspension. Specifically, embodiments of the pharmaceutical suspensions provided herein may include liquid flavors comprising terpene and/or terpinols. In some embodiments, the liquid flavor(s) may include the terpene limonene. Particular chemical compounds, and specifically the addition of liquid flavors comprising limonene, can minimize the aeration of the suspension, increase the homogeneity of the suspension, and improve the dose weight accuracy when the suspension is injected into molds. As used herein, "dose weight accuracy" and related terms refer to the ability to accurately dispense a pharmaceutical suspension into a pre-formed mold. The dose weight accuracy of the dosed pharmaceutical suspension may depend on a number of variables, including, but not limited to, homogeneity, viscosity, chemical components, dosing instrument, etc.

As described above, traditional mechanical means of anti-aeration and/or minimizing aeration have not been found to be successful due to the high viscosity of the pharmaceutical suspension. For example, applying a vacuum to the pharmaceutical suspension can cause a height of the suspension to rise because the viscous suspension "holds onto" the entrained air. Volatile formulation components may also be lost during vacuum processing. Further, traditional anti-aerating agents, such as ethanol or simethicone emulsion are similarly ineffective at anti-aerating the suspension.

Accordingly, it has been discovered that some chemical compounds, and in particular, liquid flavors comprising terpenes and/or terpinols such as limonene, can minimize the aeration of the pharmaceutical suspension when hydrophobic coated API are mixed in to the matrix solution/suspension. By minimizing aeration, the hydrophobic coated API are more efficiently and effectively dispersed throughout the pharmaceutical suspension. This increased dispersion can increase the homogeneity of the pharmaceutical suspension, the dose weight accuracy, as well as the content uniformity of the finished product.

As described above, mixing hydrophobic coated API into a matrix solution/suspension can generate entrained air, or air bubbles in the liquid. Because the coated API are hydrophobic, they have a generally low affinity for the matrix solution/suspension. Thus, instead of readily associating with and dispersing into the matrix solution/suspension, the hydrophobic coated API preferably associate with the entrained air. In many fluids, air bubbles typically travel to the surface of the fluid and disappear into the air above. However, because the hydrophobic coated API have an affinity for the entrained air, the hydrophobic coated API "hold onto" the air bubbles, preventing them from traveling to the surface and releasing into the air above the fluid. This causes the pharmaceutical suspension to become aerated. Aeration of the pharmaceutical suspension can cause phase separation, and thus, a non-homogeneous suspension. The phase separation can also become exaggerated upon exposure to shear forces introduced by dosing pumps. Non-homogenous pharmaceutical suspensions can cause pump seizures when passed through dosing pumps, leading to inaccurate dose weights and a lack of uniformity throughout the finished product as well as poor production efficiency through stoppages.

Additionally, pharmaceutical suspensions comprising hydrophobic coated API can have high viscosities due to a high loading of hydrophobic coated API (i.e., as much as 50 wt. % hydrophobic coated API). Entraining air into the pharmaceutical suspension during in-line mixing of the hydrophobic coated API into suspension, as described above, can increase the viscosity of the pharmaceutical suspension even further. Accordingly, not only does the phase separation and non-homogeneity of the suspension adversely impact the dose weight accuracy and uniformity of the final product, but so too does the increased viscosity.

Interestingly, it has been found that certain chemical compounds, when added to the matrix solution/suspension, can minimize the aeration of pharmaceutical suspensions comprising hydrophobic coated API. Particularly, chemical compounds comprising terpene and/or terpinol, according to some embodiments provided herein, may minimize the amount of the entrained air in pharmaceutical suspensions caused by in-line mixing of hydrophobic coated API into matrix solutions/suspensions. For example, suspensions comprising liquid flavors comprising terpenes and/or terpinols, even in relatively low concentrations, can minimize aeration of pharmaceutical suspensions. Specifically, it has been discovered that matrix solutions/suspensions comprising one or more liquid flavor comprising limonene can minimize aeration in pharmaceutical suspensions during in-line mixing of hydrophobic coated API. Other chemical compounds including terpenes and terpinols have been shown to be successful at minimizing aeration of pharmaceutical suspensions as well. For example, chemical compounds including terpenes such as limonene, carvone, humulene, taxadiene, and squalene may be suitable for minimizing the aeration of the pharmaceutical suspension. Terpinol may also be a suitable anti-aerating agent. In some embodiments, pure terpenes and/or pure terpinols may be used as an anti-aerating agent. In some embodiments, a liquid flavor comprising terpene and/or terpinol may be used as an anti-aerating agent. In some embodiments, other suitable chemical compounds comprising terpene and/or terpinol may be used as an anti-aerating agent.

One challenge posed with some chemical compounds comprising terpene and/or terpinol, such as some liquid flavors, is that they tend to be relatively oily. As with conventional oil and water, these oily chemical compounds may not readily disperse into a matrix solution/suspension. However, as discussed below, matrix solutions/suspensions according to embodiments here may include gelatin as a matrix former. Gelatin is inherently a mild surfactant. Surfactants can lower the surface tension between two materials. Accordingly, in some embodiments, the gelatin of the matrix solution/suspension can reduce the surface tension between the oily chemical compounds and the matrix solution/suspension. This can allow adequate incorporation of the oily chemical compounds, such as liquid flavors, into the matrix solution/suspension.

Under normal processing conditions, without use of chemical compounds comprising terpene and/or terpinol, the coating of the hydrophobic coated API erodes with time due to shear forces required to mix the hydrophobic coated API into the matrix solution/suspension to form the pharmaceutical suspension. However, there is a "processing window" of two or more hours wherein the coating retains significant functionality. The exact time of this "processing window" varies for each product, and can depend upon the composition of the components of the hydrophobic coated API, the composition of the matrix solution/suspension, the amount of material used to prepare the hydrophobic coated API, the physicochemical properties of API, and/or the conditions of mixing. Unfortunately, in the presence of chemical compounds comprising terpenes and/or terpinols this "processing window" can be significantly reduced due to interactions between these chemical compounds and the coating of the hydrophobic coated API. These interactions may damage the functional properties of the coating. For example, interactions between liquid flavors and the coating of the hydrophobic coated API may damage any taste-masking functionality of the coating. That said, it has been discovered that there is a threshold chemical compounds (i.e., liquid flavor) concentration below which the chemical compound does not significantly compromise the coating, yet the "processing window" is not reduced so much that the coating of the hydrophobic coated API significantly erodes. Accordingly, this optimal amount of chemical compound comprising terpene and/or terpinol adequately minimizes the aeration of the pharmaceutical suspension, resulting in a homogenous pharmaceutical suspension that can be accurately dosed into molds to yield a uniform final product.

Additionally, chemical compounds comprising terpene and/or terpinol, and specifically liquid flavoring agents comprising limonene, have the potential to lower the freezing point of the pharmaceutical suspension, which could lead to melting defects for products further processed by freeze-drying. In particular, limonene has a freezing point of −74° C. However, no melting defects have been observed during the preparation of the disclosed product, and thus at least some chemical compounds comprising terpene and/or terpinol do not impact the pharmaceutical suspension such that the freezing and freeze-drying process steps downstream are adversely affected. The absence of melting defects under the present circumstances is believed to be due to the high solids content of the suspension, which helps to maintain the structure of the product, even in the presence of a freezing point depressing agent (i.e., limonene).

Matrix solution/suspension compositions according to embodiments described herein may include a matrix former, a structure former, an anti-aerating agent, a viscosity modifier, and/or a solvent.

In some embodiments, an amount of a chemical compounds comprising terpene and/or terpinol (i.e., an anti-aerating agent) in the matrix solution/suspension, the pharmaceutical suspension, or the pharmaceutical composition may be from 0.001 to 5.0% w/w. In some embodiments, an amount of chemical compounds comprising terpene and/or terpinol (i.e., an anti-aerating agent) in the matrix solution/suspension, the pharmaceutical suspension, or the pharmaceutical composition can be 1-5% w/w, 1-4% w/w, 1-3% w/w, 1-2% w/w, 0.05 to 3.0% w/w, 0.1 to 2.0% w/w, or 0.5 to 1.0% w/w. In some embodiments, more than 0.001% w/w, more than 0.01% w/w, more than 0.05% w/w, more than 0.1% w/w, more than 0.3% w/w, more than 0.5% w/w, more than 0.8% w/w, more than 1.0% w/w, more than 1.5% w/w, more than 2.0% w/w, more than 2.5% w/w, more than 3.0% w/w, more than 3.5% w/w, more than 4.0% w/w, or more than 4.5% w/w of chemical compounds comprising terpene and/or terpinol (i.e., an anti-aerating agent) are in the matrix solution/suspension, the pharmaceutical suspension, or the pharmaceutical composition. In some embodiments, less than 5.0% w/w, less than 4.5% w/w, less than 4.0% w/w, less than 3.5% w/w, less than 3.0% w/w, less than 2.5% w/w, less than 2.0% w/w, less than 1.5% w/w, less than 1.0% w/w, less than 0.8% w/w, less than 0.6% w/w, less than 0.3% w/w, or less than 0.1% w/w of chemical compounds comprising terpene and/or terpinol (i.e., an anti-aerating agent) are in the matrix solution/suspension, the pharmaceutical suspension, or the pharmaceutical composition. In some embodiments, a suitable anti-aerating agent may include orange flavor, strawberry flavor, mint flavor, raspberry flavor, licorice flavor, orange flavor, lemon flavor, lime flavor, grapefruit flavor, caramel flavor, vanilla flavor, cherry flavor, grape flavor, mixed fruit flavor, tutti-frutti flavor or any combination thereof.

Minimizing Agglomeration Examples

Several trials were performed to evaluate the effectiveness of removing excess coating material from coated API by sieving and to optimize the coating ratios and dosing ratios. Disintegration times of pharmaceutical compositions containing various coated API were measured under various conditions to study the effect of sieving excess coating material. It may be reasonably assumed that removing excess coating material can minimize agglomeration of the coating material. Optimizing the coating and dosing ratios can also aid in minimizing coating material agglomeration. In turn, minimizing the amount of agglomeration can help maintain desired disintegration times and/or dissolution rates of the pharmaceutical composition and coated API. Accordingly, disintegration time is used as a metric to evaluate the amount of agglomeration in the following Examples. In some embodiments, the 50° C. accelerated disintegration data can be indicative of the presence of unsieved, excess coating material.

Additionally, coating ratio and dosing ratio information is provided for the Examples below. Coating ratio refers to the amount of coating materials to the amount of uncoated API. Dosing ratio refers to the amount of coated API to the matrix solution/suspension comprising of all the inactive ingredients.

Example 1: Ibuprofen was coated with carnauba wax with a coating ratio of 26:74. A dosing ratio of 40:60 was used to produce freeze dried tablets. Four separate batches of tablets were tested—Batch 1-3 over a period of 2 months, and Batch 4 over a period of 6 months. These batches of tablets were each tested at ICH (International Council for Harmonisation of Technical Requirements for Pharmaceuticals for Human Use) stability conditions of 25° C./60% RH, 30° C./65% RH, and 40° C./75% RH and sampled at one month and two months for Batches 1, 2, and 3. Additionally, each batch was exposed to a 50° C. stress condition to provide accelerated data at both two weeks and at four weeks for each study. Table 1 below provides the disintegration time data for Batches 1-3 of the two-month study of coated ibuprofen.

TABLE 1

| | | | | | | 1 Month 25° C./ 60% RH | 1 Month 30° C./ 65% RH | 1 Month 40° C./ 75% RH | 2 Month 25° C./ 60% RH | 2 Month 30° C./ 65% RH | 2 Month 40° C./ 75% RH |
|---|---|---|---|---|---|---|---|---|---|---|---|
| Batch | Batch Nos | Strength | Initial DT | 2 Week 50° C. | 4 Week 50° C. | | | | | | |

Carnauba Wax (Dosing Ratio 40:60) (2-Month Study)

| Batch | Batch Nos | Strength | Initial DT | 2 Week 50° C. | 4 Week 50° C. | 1 Month 25° C./ 60% RH | 1 Month 30° C./ 65% RH | 1 Month 40° C./ 75% RH | 2 Month 25° C./ 60% RH | 2 Month 30° C./ 65% RH | 2 Month 40° C./ 75% RH |
|---|---|---|---|---|---|---|---|---|---|---|---|
| 1 | Z3876/128 | 400 MG | <2 s | <4 s | <10 s | <4 s | <4 s | <4 s | <3 s | <4 s | <7 s |
| 2 | Z4630/97 | 50 MG | <2 s | <4 s | <7 s | <2 s | <2 s | <2 s | <2 s | <2 s | <15 s |
| 3 | Z4630/101 | 50 MG | <3 s | <3 s | <4 s | <1 s | <2 s | <3 s | <2 s | <2 s | <2 s |

Figure 4A:
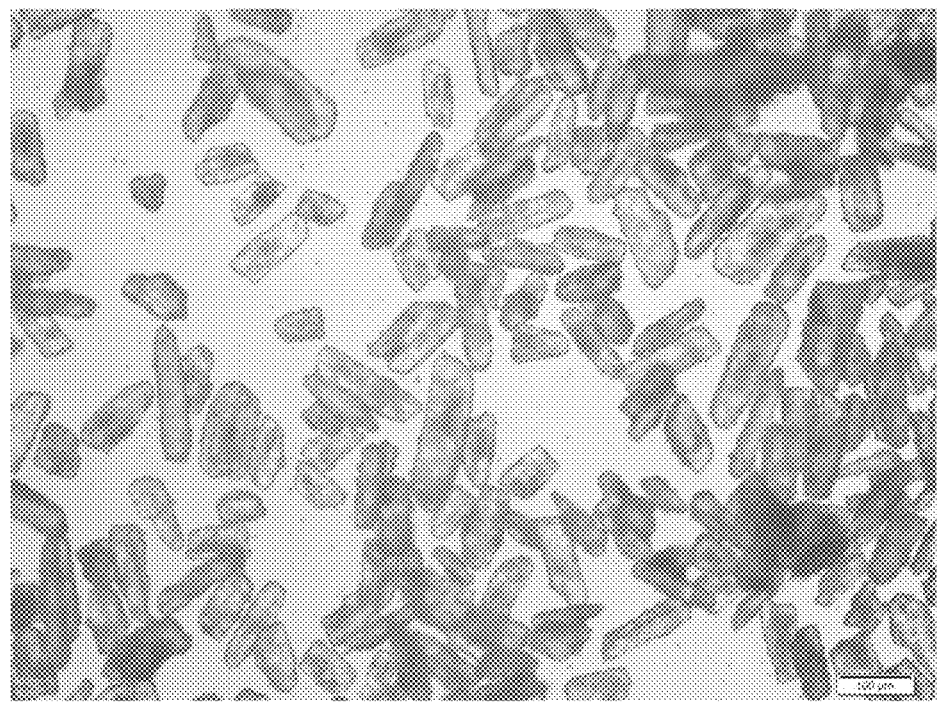
FIGS. 4A-4J are a series of photomicrographs taken of sieved coated API for Examples 1-4.
Figure 4B:
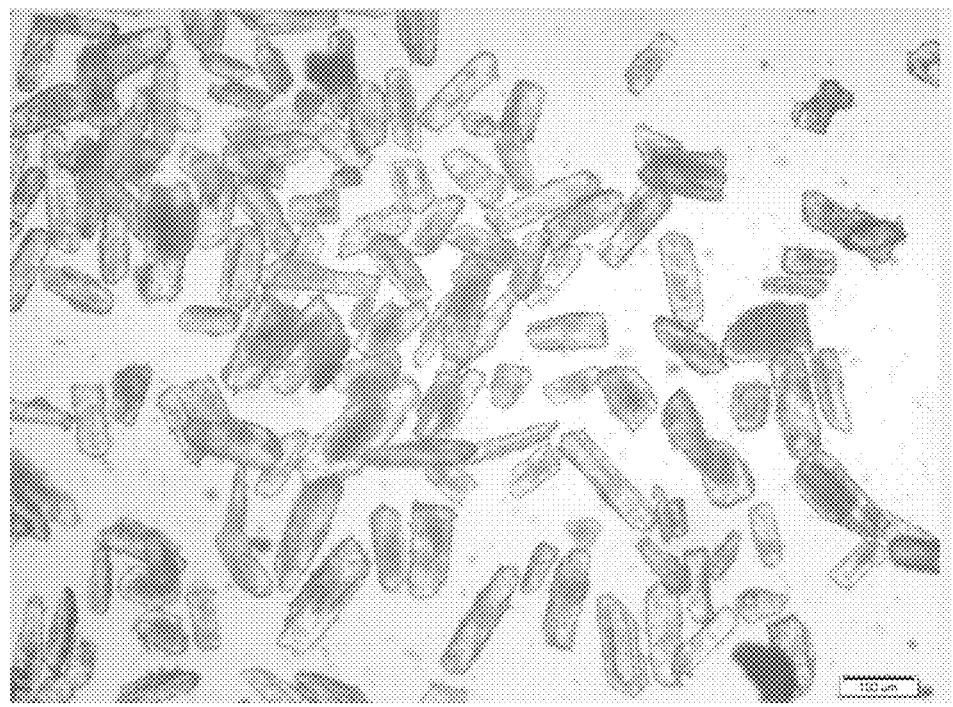

Coated Ibuprofen for Batch 2 was poorly sieved post Ibuprofen coating. Microscopic examination (FIG. 4B) of the sieved coated Ibuprofen showed the presence of an excess amount of unbound coating material. Microscopic examination of the sieved coated Ibuprofen also showed that the Ibuprofen was poorly coated. As shown in the last column of Table 1, this batch exhibited a significantly longer disintegration time at the 40° C./75% RH stability testing conditions after two-months. (The initial disintegration time was less than two seconds, and the disintegration time at two months was almost 15 seconds). Accordingly, this result supports the hypothesis that presence of an excess amount of unbound coating material in the pharmaceutical product is responsible for extended disintegration time over time (as the pharmaceutical product ages) because of the agglomeration of the unbound coating material during storage.

Figure 4C:
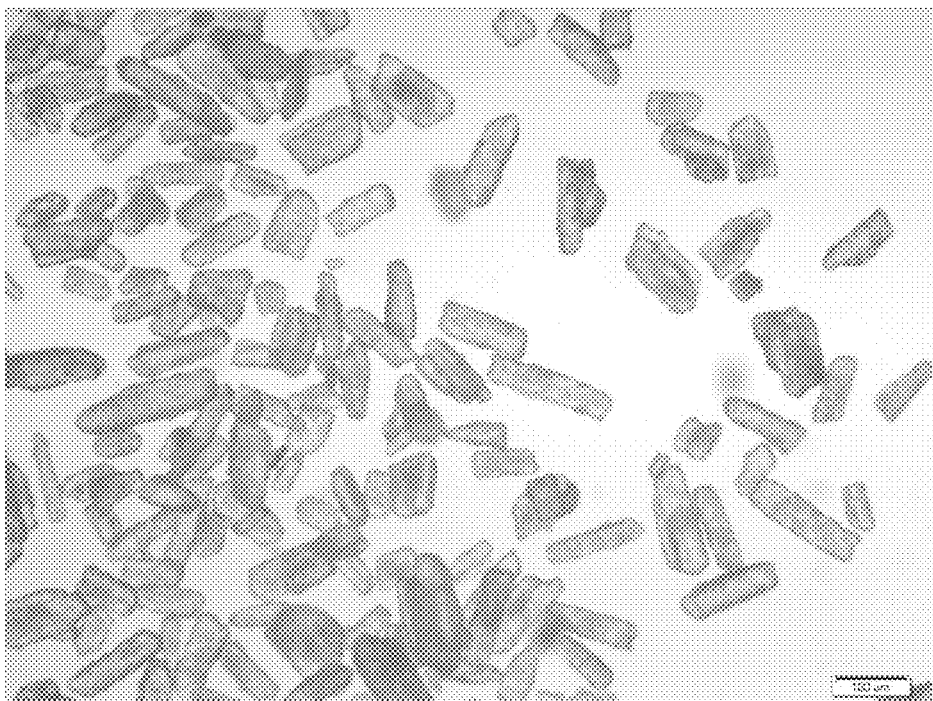

Conversely, coated Ibuprofen for Batch 3 was sieved well post Ibuprofen coating. Microscopic examination (FIG. 4C) of the sieved coated Ibuprofen showed that the Ibuprofen was well coated since there is an absence of unbound coating material. The disintegration time for the samples of this batch changed very little over the two-month period for any of the ICH stability conditions. (The disintegration time throughout the two-month study fluctuated between approximately one second and approximately three seconds). This supports the hypothesis that minimizing the presence of excess unbound coating material by sieving, for example, will help to prevent the agglomeration of coating material in pharmaceutical product when place on storage, particularly at higher temperatures over time.

The coated Ibuprofen for Batch 1 was sieved post Ibuprofen coating. Batch 1 exhibited similar disintegration time of less than 2 seconds compared to Batch 2 and 3 for the initial time data points. However, at the 40 C/75% RH stability testing conditions after two-months, the disintegration time increased to approximately 7 seconds or less. When stored for 4 weeks at 50° C., the disintegration time increased to approximately 10 seconds or less. This suggests that the sieving process for this batch did not sufficiently remove the excess coating material, hence the presence of residual unbound coating material. Batch 2 experienced even more unbound coating material and agglomeration on storage to a greater extent than that of Batch 1. Microscopic examination (FIG. 4A) of the sieved coated Ibuprofen showed that the Ibuprofen particles were moderately well coated with residue amount of unbound coating material present.

Table 2 below shows the disintegration time data for the six-month study of coated Ibuprofen (i.e., Batch 4).

TABLE 2

Carnauba Wax (Dosing Ratio 40:60) (6-Month Study)

| Batch | Batch Nos | Strength | Initial | 2 Week 50° C. | 4 Week 50° C. | 1 Month 25° C./ 60% RH | 1 Month 30° C./ 65% RH | 1 Month 40° C./ 75% RH |
|---|---|---|---|---|---|---|---|---|
| 4 | Z3876/131 | 200 MG | <5 s | <20 s | <13 s | <5 s | <4 s | <5 s |

| Batch | 3 Month 25° C./ 60% RH | 3 Month 30° C./ 65% RH | 3 Month 40° C./ 75% RH | 6 Month 25° C./ 60% RH | 6 Month 30° C./ 65% RH | 6 Month 40° C./ 75% RH |
|---|---|---|---|---|---|---|
| 4 | <4 s | <3 s | <4 s | <2 s | <2 s | <2 s |

Figure 4D:
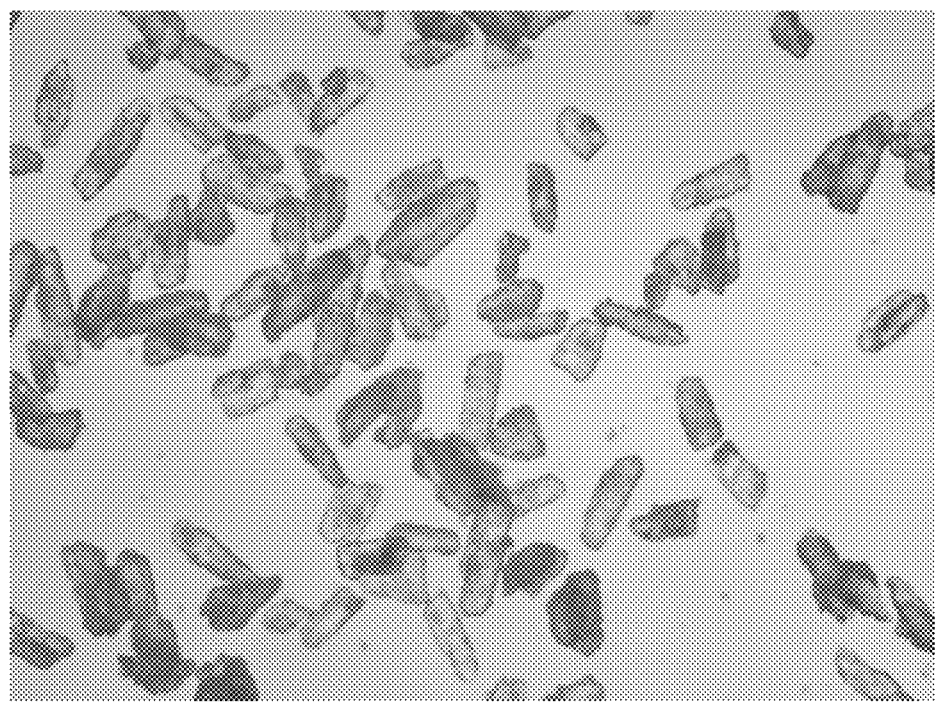

The coated Ibuprofen for Batch 4 was sieved post Ibuprofen coating. Batch 4 of Table 2 did not show much change in disintegration time throughout the duration of the six-month study. The initial disintegration time of Batch 4 was approximately five seconds, and the final disintegration time of the 25° C./60% RH samples was approximately two seconds; the 30° C./65% RH samples approximately two seconds, and the 40° C./75% RH samples approximately two seconds. However, an increase was seen when stored at 50° C. Since no increase was seen in the tablets stored at temperatures of 40° C. and below, this suggests that sieving has removed most of the unbound excess coating material but with sufficient residue amount that agglomerate when the tablets were placed at 50° C. Microscopic examination (FIG. 4D) showed that the sieved coated Ibuprofen showed that the Ibuprofen were moderately well coated with residue amount of unbound coating material present.

Figure 4E:
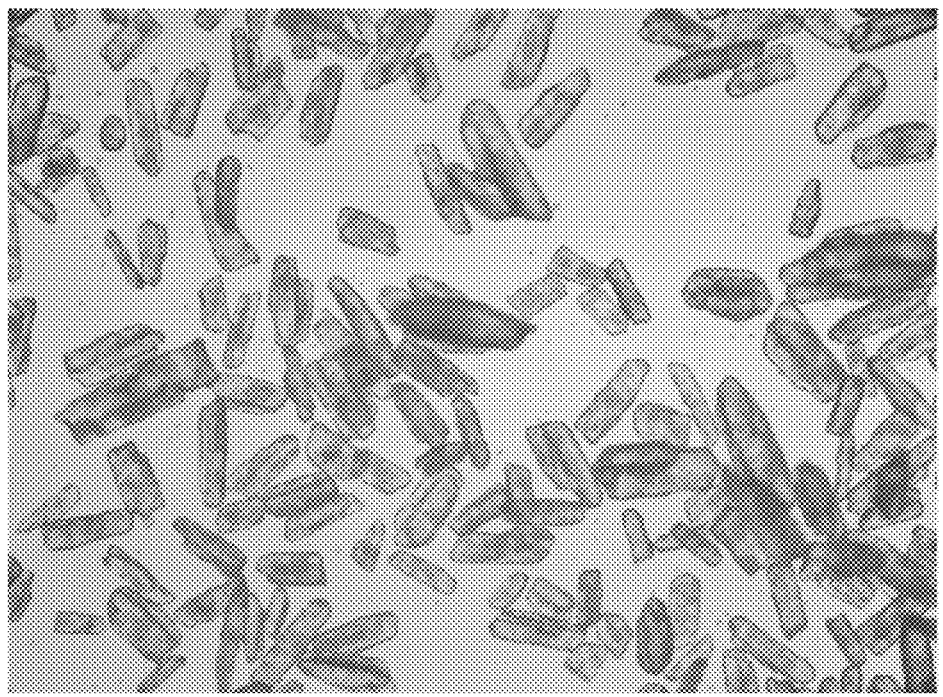

Example 2: Ibuprofen was coated with Sasol (synthetic) wax with a theoretical coating ratio of 26:74. The coated Ibuprofen was sieved after coating. A dosing ratio of 40:60 was used to produce freeze dried tablets and tested over two months. The Ibuprofen strength was 200 mg. Each batch was tested at ICH stability conditions of 25° C./60% RH, 30° C./65% RH, and 40° C./75% RH. Additionally, the samples were exposed to a 50° C. stress condition to provide accelerated data at two weeks and at four weeks during the study. Table 3 below provides the disintegration time data for the 40:60 dosing ratio two month study of coated Ibuprofen. Microscopic examination (FIG. 4E) of the sieved coated Ibuprofen showed that the Ibuprofen were moderately well coated with a small amount of unbound coating material.

Batch 5 of Table 3 shows no substantial change in the disintegration time during the two months of the study, nor at the 50° C. accelerated conditions. Specifically, the initial disintegration time of Batch 5 was approximately three seconds, and the disintegration time at two months for all three ICH stability conditions (25° C./60% RH, 30° C./65% RH, and 40° C./75% RH) was approximately four seconds.

The disintegration time for the 50° C. accelerated condition at two weeks was approximately three seconds and at 4 weeks was approximately four seconds. Based on the 50° C. data, a small residue amount of unbound excess coating material may be present. If so, this small amount of unbound excess coating material does not cause a significant amount of agglomeration on storage, since the disintegration time does not increase much, if at all. This compares well with Batch 3 in Example 1 where a different wax was used. These 2 examples demonstrate that if the unbound excess coating material is efficiency removed by sieving, agglomeration of the coating material in the pharmaceutical product on storage can be minimized or prevented, in particular at higher temperatures and upon prolonged storage period.

Figure 4F:
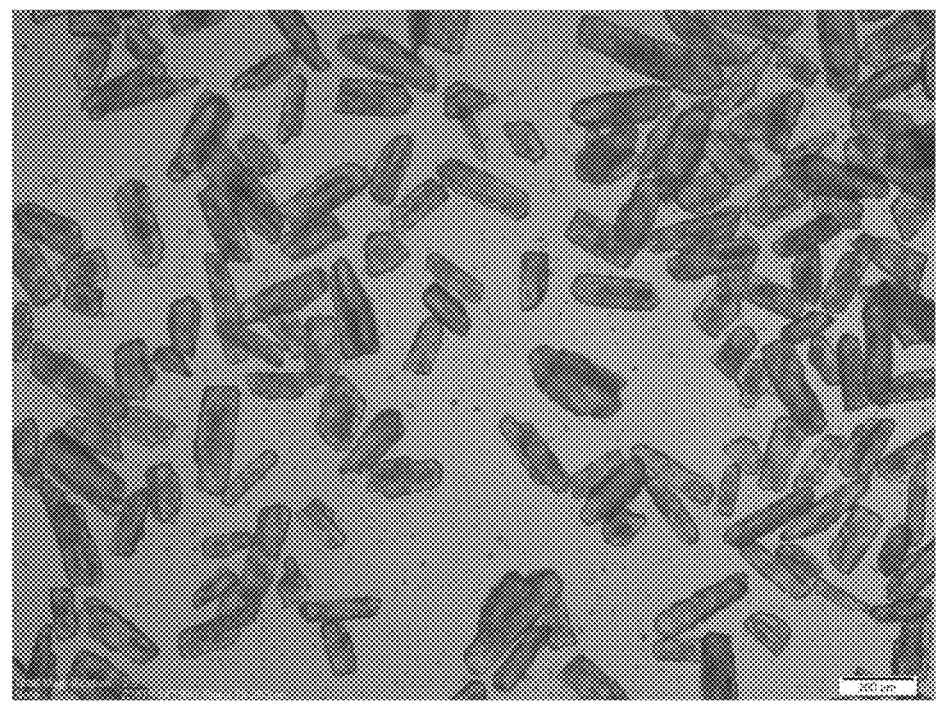

Example 3: Ibuprofen was coated with Sasol (synthetic) wax with a theoretical coating ratio of 26:74. The coated ibuprofen was then sieved after coating. A dosing ratio of 50:50 was used to produce freeze dried tablets and tested over three months. The Ibuprofen strength was 200 mg. As above in Examples 1 and 2, each batch was tested at ICH stability conditions of 25° C./60% RH, 30° C./65% RH, and 40° C./75% RH. The samples were also exposed to a 50° C. stress condition to provide accelerated data at two weeks and at four weeks during each study. Table 4, below, provides data for the three-month study of 50:50 Sasol wax-coated Ibuprofen. Microscopic examination (FIG. 4F) of the sieved coated API for Batch 6 showed the Ibuprofen were coated well and with some unbound coating material.

TABLE 3

Sasol Wax (Dosing Ratio 40:60) Ibuprofen Strength: 200 mg

| Batch | Batch Nps | Initial DT | 2 Week 50° C. | 4 Week 50° C. | 1 Month 25° C./ 60% RH | 1 Month 30° C./ 65% RH | 1 Month 40° C./ 75% RH | 2 Month 25° C./ 60% RH | 2 Month 30° C./ 65% RH | 2 Month 40° C./ 75% RH |
|---|---|---|---|---|---|---|---|---|---|---|
| 5 | Z3876/138 | <3 s | <3 s | <4 s | <2 s | <2 s | <5 s | <4 s | <4 s | <4 s |

TABLE 4

Sasol Wax (Dosing Ratio 50:50) Ibuprofen Strength: 200 mg

| Batch | Batch Nos | Initial DT | 2 Week 50° C. | 4 Week 50° C. | 1 Month 25° C./60% | 1 Month 30° C./ 65% RH | 1 Month 40° C./ 75% RH |
|---|---|---|---|---|---|---|---|
| 6 | Z3876/142 | <1 s | <2 s | <2 s | <2 s | <2 s | <2 s |
| 7 | Z3876/141/1 | <2 s | <5 s | <5 s | <2 s | <3 s | <3 s |

| Batch | 2 Month 25° C./ 60% RH | 2 Month 30° C./ 65% RH | 2 Month 40° C./ 75% RH | 3 Month 25° C./ 60% RH | 3 Month 30° C./ 65% RH | 3 Month 40° C./ 75% RH |
|---|---|---|---|---|---|---|
| 6 | <2 s | <1 s | <2 s | <2 s | <2 s | <2 s |
| 7 | <2 s | <2 s | <3 s | <2 s | <2 s | <3 s |

Neither Batch 6 nor Batch 7 showed significant change in disintegration time over the course of the three month study. Specifically, the initial disintegration time of the samples of Batch 6 was approximately one second, and the final three-month disintegration time for each of the three ICH stability conditions (25° C./60% RH, 30° C./65% RH, and 40° C./75% RH) was approximately two seconds. The disintegration time for both the two-week and the four-week accelerated 50° C. condition for Batch 6 was approximately two seconds.

The initial disintegration time for the samples of Batch 7 was approximately two seconds, and the final three-month disintegration time for the 25° C./60% RH and 30° C./65% RH ICH stability conditions was approximately two seconds. The final three-month disintegration time for the 40° C./75% RH ICH stability condition was approximately three seconds. The disintegration time for both the two-week and the four-week accelerated 50° C. condition was approximately five seconds. A high coating ratio of 50:50 can increase the amount of excess unbound coating material when left unsieved. Although both batches used a higher dosing ratio of 50:50, which means a high loading of the coated Ibuprofen and any unbound excess coating material, these data inferred that the sieving process of the coated Ibuprofen has been effective in removing the unbound excess coating materials to minimize agglomeration.

Figure 4G:
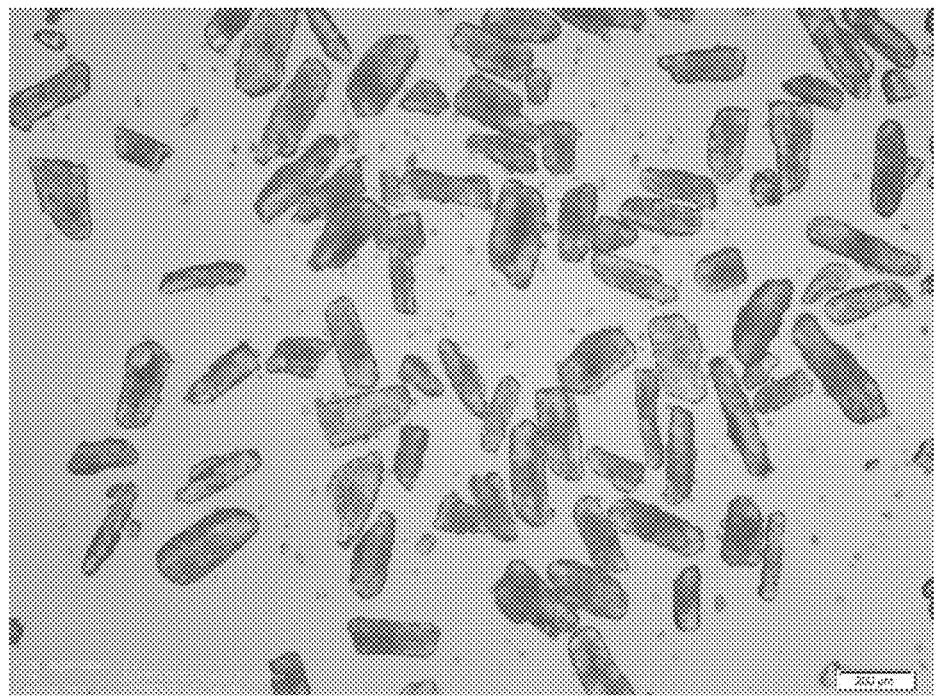
Figure 4H:
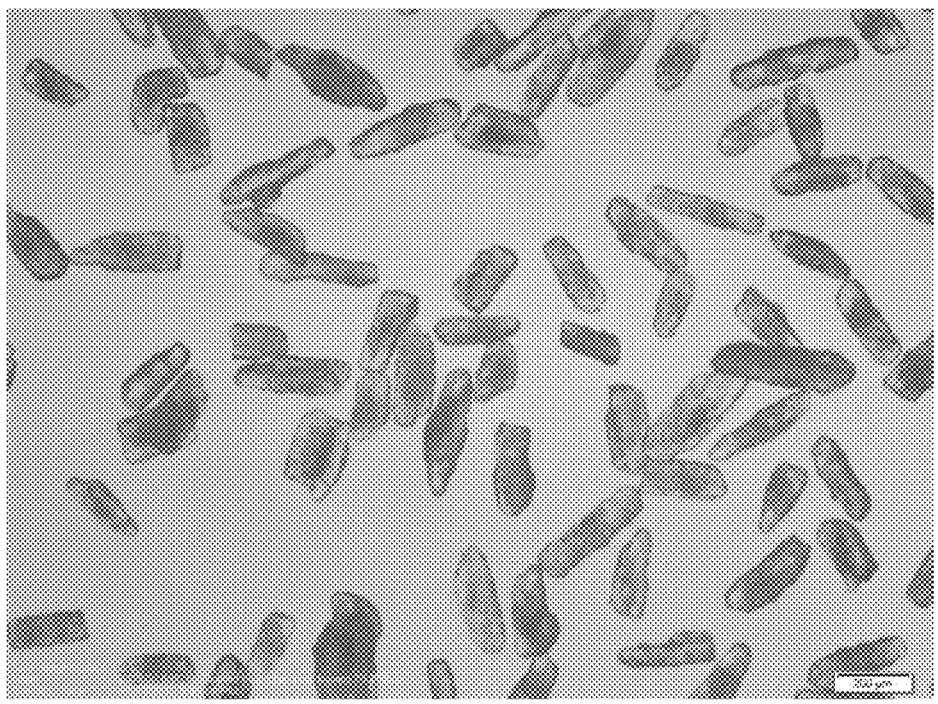
Figure 4I:
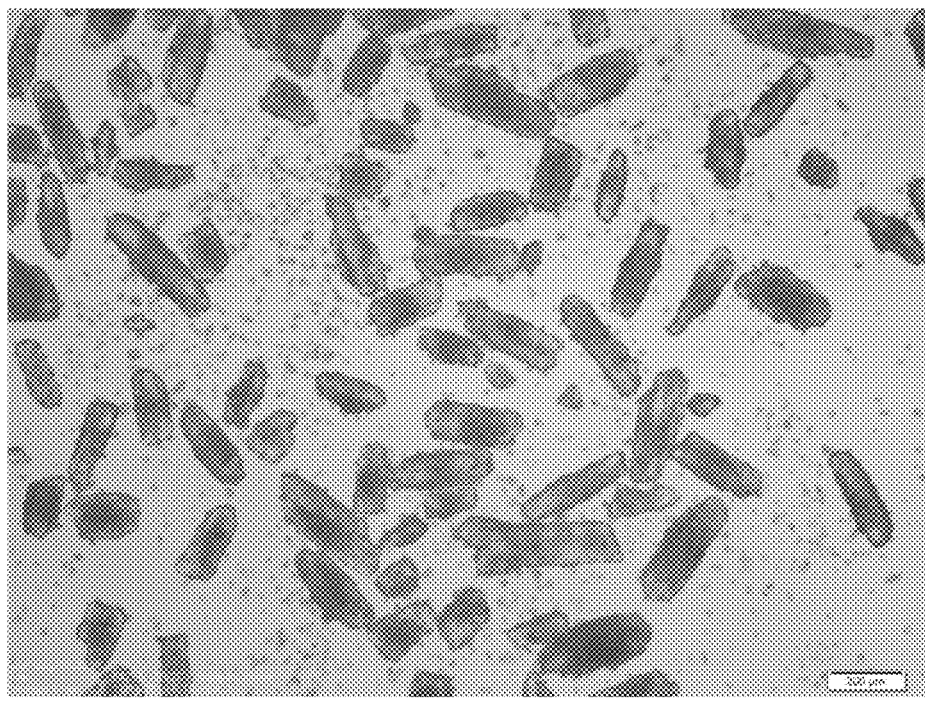
Figure 4J:
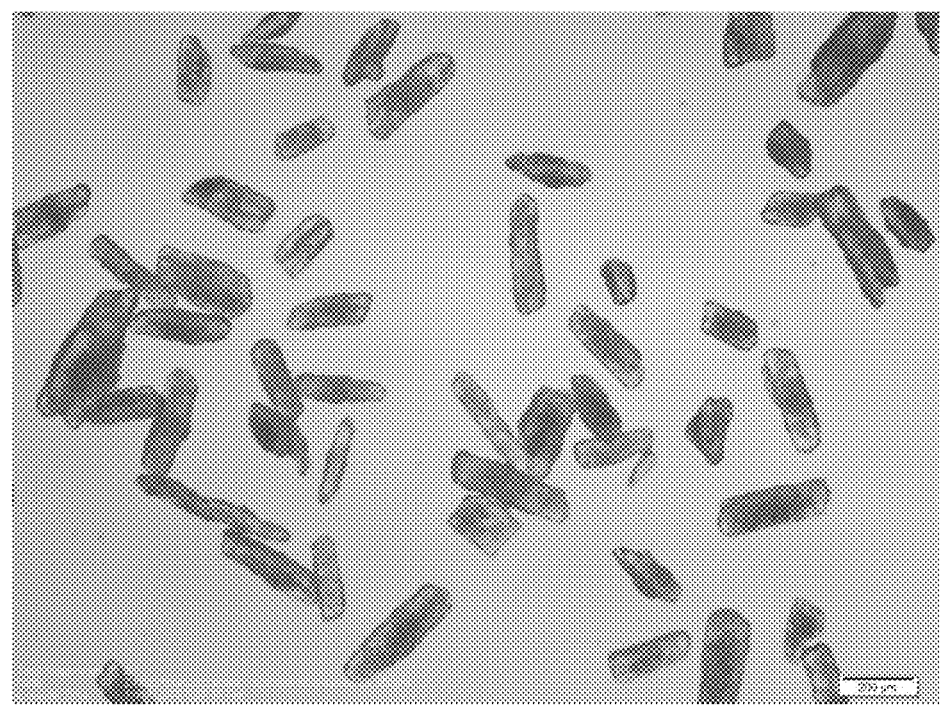

Example 4: Ibuprofen was coated with Carnauba Wax at a theoretical coating ratio of 22.5:77.5 and 30:70. A dosing ratio of 30:70 was used to produce freeze dried tablets and study over a period of 2 months. The Ibuprofen strength was 200 mg. The batches were stored in an oven at 40° C. Tablets were tested for disintegration time at the initial, Day 25, and 2 month time points. Table 5 below provides the disintegration times for the study. Microscopic examination of the unsieved coated Ibuprofen (FIGS. 4G and 4H) and sieved coated Ibuprofen (FIGS. 4I and 4J). The Ibuprofen were well coated. Sieved samples have no unbound coating material present.

TABLE 5

Carnauba Wax (Dosing Ratio 30:70) Ibuprofen Strength: 200 mg

| Batch | Bach Nps | Coated API | Coating Ratio | Initial | Day 24 At 40° C. | 2 Month At 40° C. |
|---|---|---|---|---|---|---|
| 8 | Z4750/186/2a | Unsieved | 22.5:77.5 | 5 s | 2 s | 2 s |
| 9 | Z4750/186/4a | Sieved | 22.5:77.5 | 4 s | 3 s | 3 s |
| 10 | Z4750/186/6a | Unsieved | 30:70 | 1 s | 2 s | 2 s |
| 11 | Z4750/186/8a | Sieved | 30:70 | 2 s | 3 s | 3 s |

Batch 8-11 show that using a dosing ratio of 30:70 for coated Ibuprofen, either unsieved (Batches 8 and 10) or sieved (Batches 9 and 11), the disintegration times of the tablets stored at 40° C. has not increased over time. This supports the hypothesis that by reducing the dosing ratio; such as to 30:70, the amount of excess unbound wax is sufficiently reduced to a level that can minimize agglomeration of the excess unbound material when stored at higher temperatures over time.

The overall summary of results from the above examples are tabulated the Table 6.

TABLE 6

Overall Summary of Results for Batches 1-11.

| Batch | Batch Nos | Drug | Strength (mg) | Coating Ratio | Dosing Ratio | Sieving of Coated API | Coating Assessment (Microscopy) | Unbounded Excess Wax (Microscopy) | Disintegration Time at 40' C./75% RH at 1/2/3/6 mths | Disintegration time at 50' C. at 2/4 wk |
|---|---|---|---|---|---|---|---|---|---|---|
| 1 | Z3876/128 | Ibuprofen | 400 | 26:74 | 40:60 | Sieved | Moderate | Present | <4-7 s | <4-10 s |
| 2 | Z4630/97 | Ibuprofen | 50 | 26:74 | 40:60 | Sieved (poor) | Poor | Present | <2-15 s | <4-7 s |
| 3 | Z4630/101 | Ibuprofen | 50 | 26:74 | 40:60 | Sieved (well) | Good | Absent | <2-3 s | <3-4 s |
| 4 | Z3876/131 | Ibuprofen | 200 | 26:74 | 40:60 | Sieved | Moderate | Present | <2-5 s | <13-20 s |
| 5 | Z3876/138 | Ibuprofen | 200 | 26:74 | 40:60 | Sieved | Good | Present | <4-5 s | <3-4 s |
| 6 | Z3876/142 | Ibuprofen | 200 | 26:74 | 50:50 | Sieved | Good | Present | <2 s | <2 s |
| 7 | Z3876/141/1 | Ibuprofen | 200 | 25:75 | 50:50 | Sieved | No Photo | No Photo | <3 s | <5 s |
| 8 | Z4750/186/2a | Ibuprofen | 200 | 22.5:77.5 | 30:70 | Unsieved | Good | Present | <2 s | No data |
| 9 | Z4750/186/4a | Ibuprofen | 200 | 22.5:77.5 | 30:70 | Sieved (well) | Good | Absent | <3 s | No data |
| 10 | Z4750/186/6a | Ibuprofen | 200 | 30:70 | 30:70 | Unsieved | Good | Present | <2 s | No data |
| 11 | Z4750/186/8a | Ibuprofen | 200 | 30:70 | 30:70 | Sieved | Good | Absent | <3 s | No data |

Preserving Functionally-Coated Ibuprofen Examples

Example 5: Hydrophobic fumed silica was used to coat functionally-coated Ibuprofen according to embodiments described herein. Specifically, the hydrophobic fumed silica that was used was Aerosil R972 ("Aerosil"). Two different concentrations of Aerosil R972 were tested—1.5% w/w and 1.0% % w/w. The size of the functionally-coated Ibuprofen were evaluated over a 6-hour holding period, during which they were subjected to low shear mixing.

Figure 5:
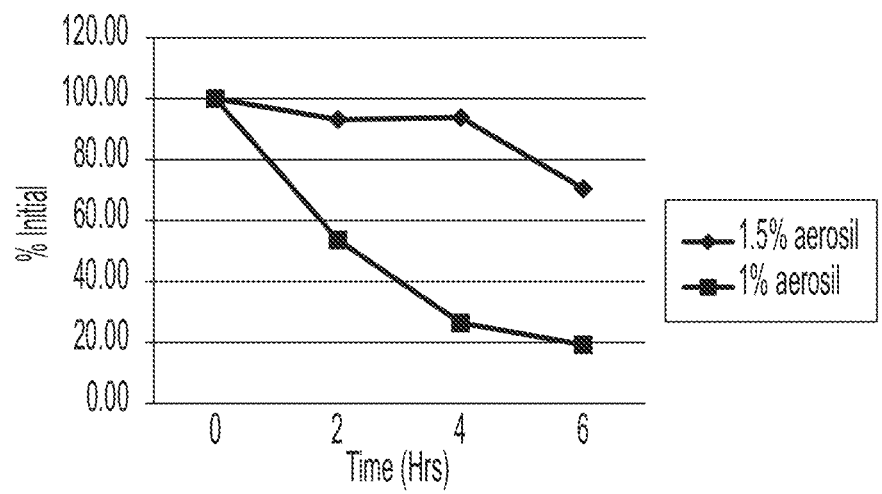
FIG. 5 is a graph providing an evaluation of d10 particle size of functionally-coated API comprising a second protective coating of different concentrations of silica, according to some embodiments.
Figure 6:
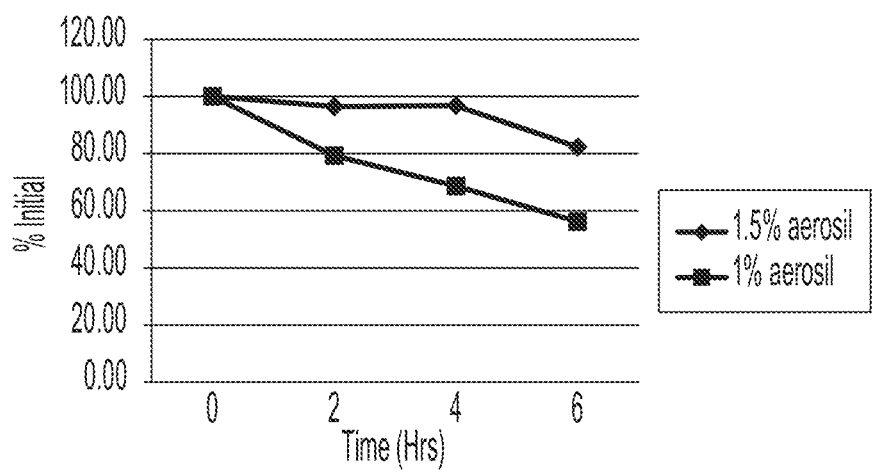
FIG. 6 shows a graph providing an evaluation of d50 particle size of functionally-coated API comprising a second protective coating of different concentrations of silica, according to some embodiments.
Figure 7:
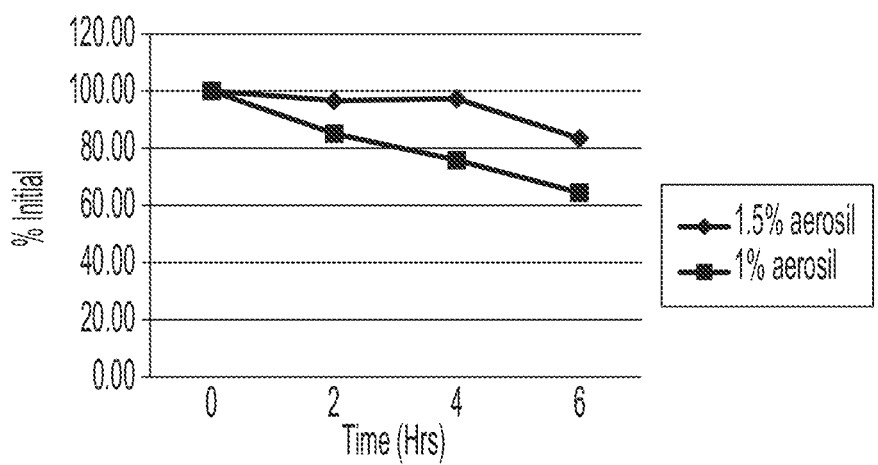
FIG. 7 shows a graph providing an evaluation of d90 particle size of functionally-coated API comprising a second protective coating of different concentrations of silica, according to some embodiments.

FIGS. 5, 6, and 7 provide evaluations of d10 particle size, d50 particle size, and d90 particle size, respectively, over a period of 6 hours. Generally speaking, a particle size expressed in terms of its d10 means that 10 percent of the particles in a given amount of sample lie below a given particle size. Accordingly, a particle size expressed in terms of its d50 means that 50 percent of the particles in a given amount of sample lie below a given particle size, and a particle size expressed in terms of its d90 means that 90 percent of the particles in a given amount of sample lie below a given particle size.

As shown in FIG. 5, the greater concentration of silica (1.5% w/w) was more effective at maintaining the original particle size, and thus maintaining the coating, than the lesser concentration of silica (1.0% w/w). Specifically, during the 6-hour period, the functionally-coated Ibuprofen comprising 1.5% w/w Aerosil lost approximately 30% of their original size, whereas the functionally-coated Ibuprofen comprising 1.0% w/w Aerosil lost approximately 80% of their original particle size.

FIG. 6 demonstrates that again the greater concentration of silica (1.5% w/w Aerosil) was more effective at maintaining the original functionally-coated Ibuprofen particle size, and thus preserving the functional coating, than the lesser concentration of silica (1.0% w/w Aerosil). Specifically, during a period of 6 hours, the functionally-coated Ibuprofen comprising 1.5% w/w Aerosil lost almost 20% of their original size, whereas the functionally-coated Ibuprofen comprising 1.0% w/w Aerosil lost approximately 45% of their original functionally-coated API particle size.

FIG. 7 also shows that the greater concentration of silica (1.5% w/w Aerosil) was more effective at maintaining the original functionally-coated Ibuprofen particle size, and thus preserving the functional coating of the functionally-coated Ibuprofen, than the lesser concentration of silica (1.0% w/w Aerosil). Specifically, during the 6-hour period, the functionally-coated Ibuprofen comprising 1.5% w/w Aerosil lost almost 15% of their original size, whereas the functionally-coated Ibuprofen comprising 1.0% w/w Aerosil lost approximately 35% of their original particle size.

Additionally, as the particle size of the functionally-coated Ibuprofen decreased, a separate population of particles comprising a particle size of 5 µm to 20 µm appeared and increased with time. These particles are believed to be non-deformable coating material particles embedded within the deformed, continuous coating material prior to erosion of the coating due to shear forces. Accordingly, as the coating erodes, and the particle size of the functionally-coated Ibuprofen decreases, the population size of these smaller particles increases as the deformed coating material surrounding them erodes, causing these non-deformable particles to release from the functionally-coated Ibuprofen.

Overall, these trials suggest that 1.5% w/w Aerosil coating the functionally-coated Ibuprofen may increase the "processing window" to approximately 4 hours, instead of the 2 hour "processing window" that exists without the silica. Within the first four hours of processing in suspension and comprising a second, outer coating comprising 1.5% w/w Aerosil, the functionally-coated Ibuprofen exhibit little, if any, erosion of the coating.

Example 6: Hydrophobic fumed silica was used to coat functionally-coated Ibuprofen according to embodiments described herein. Specifically, the hydrophobic fumed silica that was used was Aerosil R972 ("Aerosil"). Five different concentrations of Aerosil R972 were tested—0.0% w/w, 1.5% w/w, 2.5% w/w, 5.0% w/w and 10.0% w/w. The release amount of the functionally coated Ibuprofen was evaluated using dissolution testing (i.e., dissolution media of 0.01% SDS in pH 7.2 phosphate buffer, media temperature of 37° C., and media volume of 10 ml (Ibuprofen)).

Figure 8:
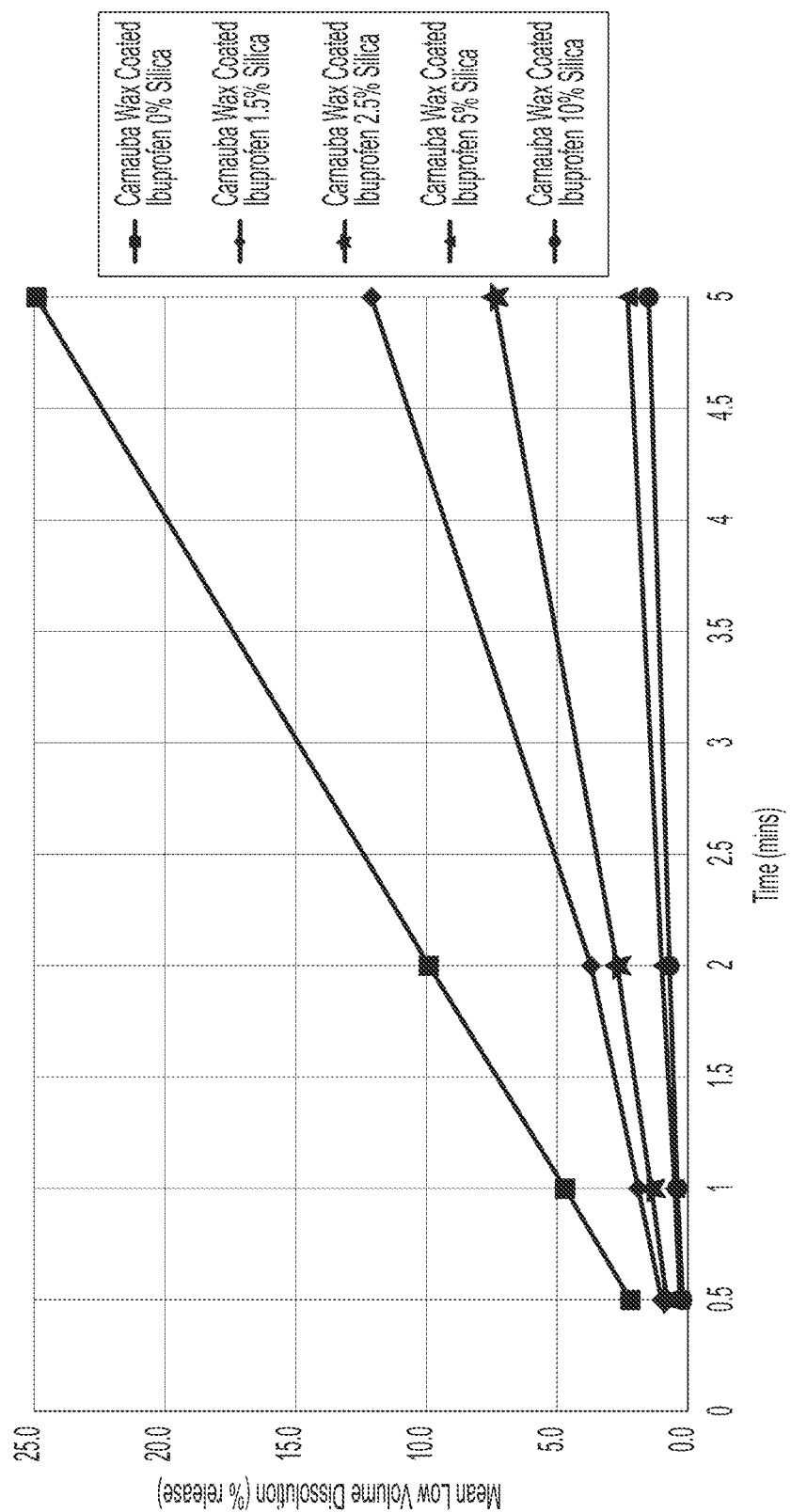
FIG. 8 shows a graph of low volume dissolution of API coated with carnauba wax with varying levels of hydrophobic fumed silica, according to some embodiments.
Figure 9:
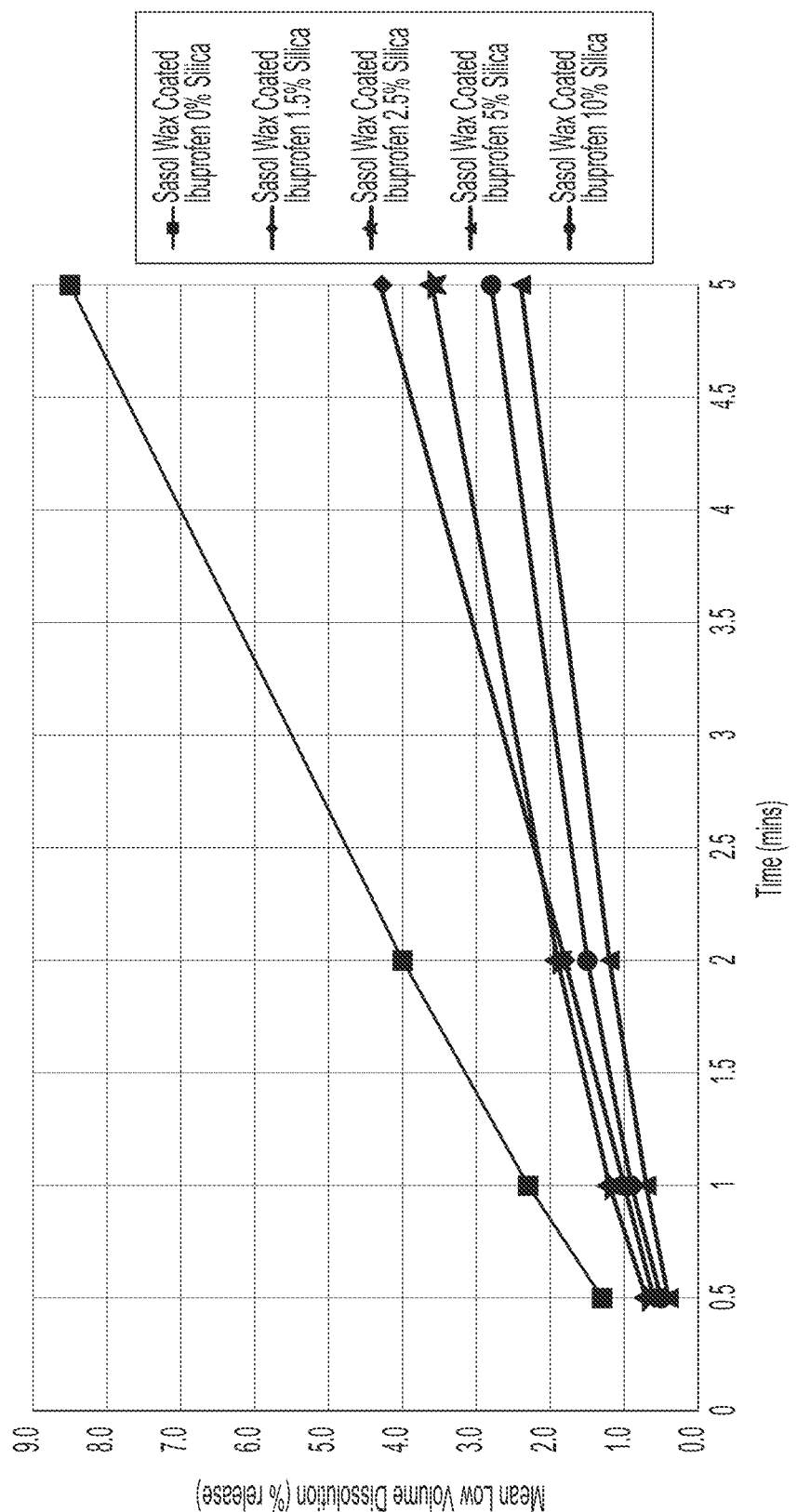
FIG. 9 shows a graph of low volume dissolution of API coated with Sasol (synthetic) wax comprising varying levels of hydrophobic fumed silica, according to some embodiments.

FIGS. 8 and 9 provide evaluations of release amount conducted on the functionally coated Ibuprofen, over a period of either 5 or 30 minutes. Generally speaking, a low volume dissolution result expressed in terms of its % release means that 'x' percent of the weight of material added has dissolved into solution.

FIG. 8 shows release data for Ibuprofen coated with carnauba wax and various amounts of hydrophobic silica. As shown in the Figure, greater concentrations of silica (up to 10.0% w/w) were more effective at providing a slower release rate in dissolution testing, and thus maintaining the coating, than the lesser concentrations of silica. Specifically, during the 5 minute testing period, the functionally-coated Ibuprofen (i.e., Ibuprofen coated with carnauba wax) comprising 10.0% w/w Aerosil exhibited a 1.5% release after 5 minutes, whereas the functionally-coated Ibuprofen comprising 0.0% w/w Aerosil exhibited a 24.9% release. Functionally-coated Ibuprofen comprising intermediate levels of Aerosil (i.e., 1.5% w/w, 2.5% w/w and 5.0% w/w) showed dissolution results after 5 minutes of 12.1% release, 7.4% release and 2.3% release, respectively.

Figure 10:
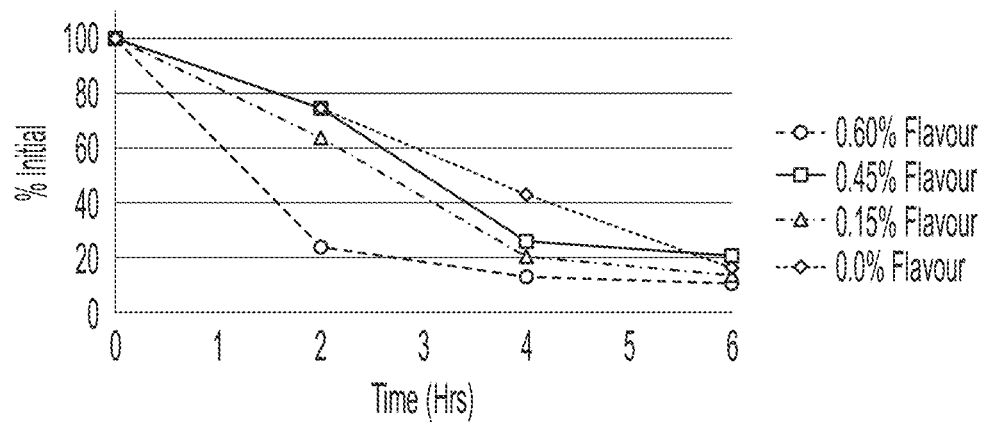
FIG. 10 shows a graph providing an evaluation of d10 particle size of hydrophobic coated API with various concentrations of liquid flavor.

FIG. 9 provides release data for Ibuprofen coated with Sasol (synthetic) wax and various levels of hydrophobic silica. FIG. 10 also shows that greater concentrations of silica (up to 10.0% w/w) were more effective at providing a slower release rate in dissolution testing, and thus maintaining the coating, than the lesser concentrations of silica. Specifically, during the 5 minute testing period, the functionally-coated Ibuprofen (i.e., Ibuprofen coated with synthetic wax) comprising 10.0% w/w Aerosil exhibited a 2.8% release after 5 minutes, whereas the functionally-coated Ibuprofen comprising 0.0% w/w Aerosil shows an 8.5% release. Functionally-coated Ibuprofen comprising intermediate levels of Aerosil (i.e., 1.5% w/w, 2.5% w/w and 5.0% w/w) gave dissolution results after 5 minutes of 4.3% release, 3.6% release and 2.4% release, respectively.

Minimizing Aeration Examples

The effectiveness of chemical compounds comprising terpene and/or terpinol at minimizing aeration can be determined in part by measuring the particle size of the hydrophobic coated Ibuprofen in pharmaceutical suspension over time. If the chemical compound is effective, the aeration of the suspension will be adequately low and the particle size of the hydrophobic coated Ibuprofen will remain constant or decrease very little over time. If ineffective, the aeration of the suspension will be higher than desired and the particle size of the hydrophobic coated Ibuprofen can decrease more substantially over time. The extent of aeration of the suspension is assessed by measurement of height of the foam in the mixing vessel. The particle size of the functionally-coated particles can be measured using laser diffraction, a particle analyzer such as a Malvern Mastersizer, or any other suitable means for analyzing fine particles.

Example 7: A series of suspension mixes were manufactured by mixing the coated Ibuprofen in the matrix solution/suspension containing various levels of limonene, orange flavor, and strawberry flavor. The height of the foam from these suspension is summarized in Table 7, 8, and 9 respectively.

TABLE 7

Height of foam from mixes containing various levels of limonene.

| Concentration of limonene (% w/w) | Foam Height (mm) |
|---|---|
| 0 | 5 |
| 0.15 | 2 |
| 0.30 | 1 |
| 0.6 | 1 |

TABLE 8

Height of foam from mixes containing various levels of orange flavor.

| Concentration of orange flavor (% w/w) | Foam Height (mm) |
|---|---|
| 0 | 5 |
| 0.15 | 1 |
| 0.30 | 0 |
| 0.6 | 0 |

TABLE 9

Height of foam from mixes containing various levels of strawberry flavor.

| Concentration of strawberry flavor (% w/w) | Foam Height (mm) |
|---|---|
| 0 | 5 |
| 0.15 | 3 |
| 0.30 | 3 |
| 0.6 | 3 |

The results in Tables 7 and 8 show that the addition of limonene and orange flavor at level 0.15% w/w and above minimize the aeration. For strawberry (Table 9), it also reduced aeration but not to the same extent.

Figure 11:
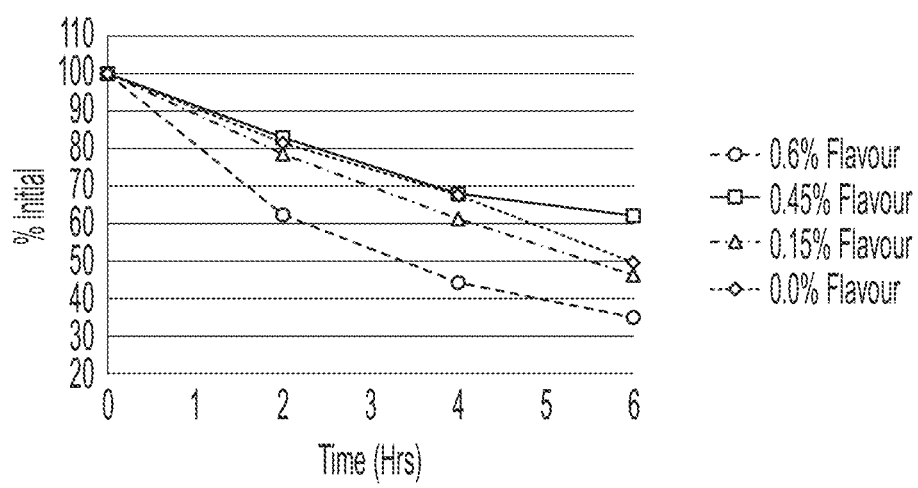
FIG. 11 shows a graph providing an evaluation of d50 particle size of hydrophobic coated API with various concentrations of liquid flavor.
Figure 12:
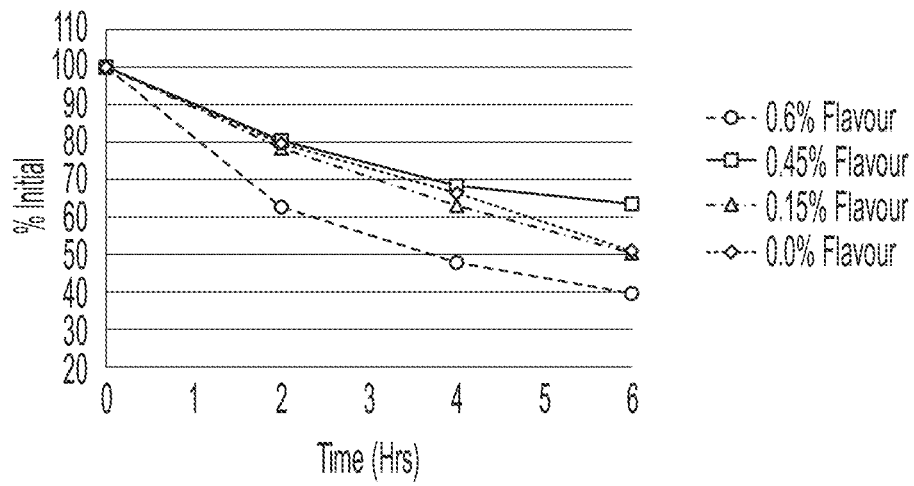
FIG. 12 shows a graph providing an evaluation of d90 particle size of hydrophobic coated API with various concentrations of liquid flavor.

Example 8: FIGS. 10, 11, and 12 show the decrease in particle size (d10, d50, and d90, respectively) of hydrophobic coated Ibuprofen in a pharmaceutical suspension comprising various concentrations of liquid orange flavor. A particle size expressed in terms of its d10 means that 10 percent of the particles in a given volume of sample lie below a given particle size. Accordingly, a d50 particle size represents 50 percent of the particles in a given volume of sample lie below a given particle size, and a d90 particle size represents 90 percent of the particles in a given volume of sample lie below a given particle size. Specifically, FIGS. 10-12 show test results for suspension formulations containing hydrophobic coated Ibuprofen and liquid orange flavor at concentrations including 0.0%, 0.15%, 0.45%, and 0.60% w/w, held over a period of up to 6 hours with low shear mixing.

At concentrations of up to 0.45% w/w of orange flavor (including 0.15% w/w), the decrease in d10, d50, and d90 particle size within the first 2 hour "processing window" is largely similar to that of a pharmaceutical suspension comprising hydrophobic coated Ibuprofen without any liquid flavor (0% liquid flavor). However, at a concentration of 0.6% w/w liquid orange flavor, the coating of the hydrophobic coated Ibuprofen is readily removed and a rapid decrease in particle size is observed. Further, at a liquid orange flavor concentration of 0.3% w/w, the aeration of the suspension was sufficiently low with only little, if any damage to the coating of the coated ibuprofen, and only minimal decrease in particle size of the hydrophobic coated Ibuprofen.

Figure 13:
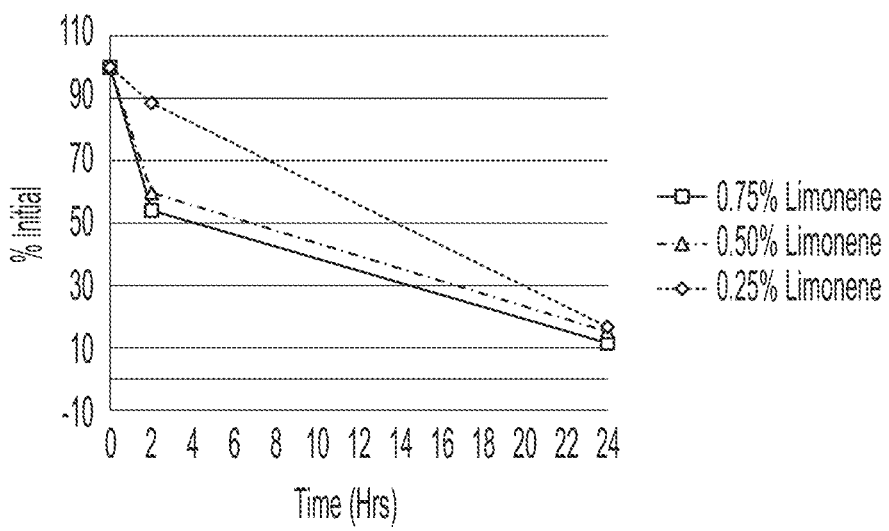
FIG. 13 shows a graph providing an evaluation of d10 particle size of hydrophobic coated API with various concentrations of pure limonene.
Figure 14:
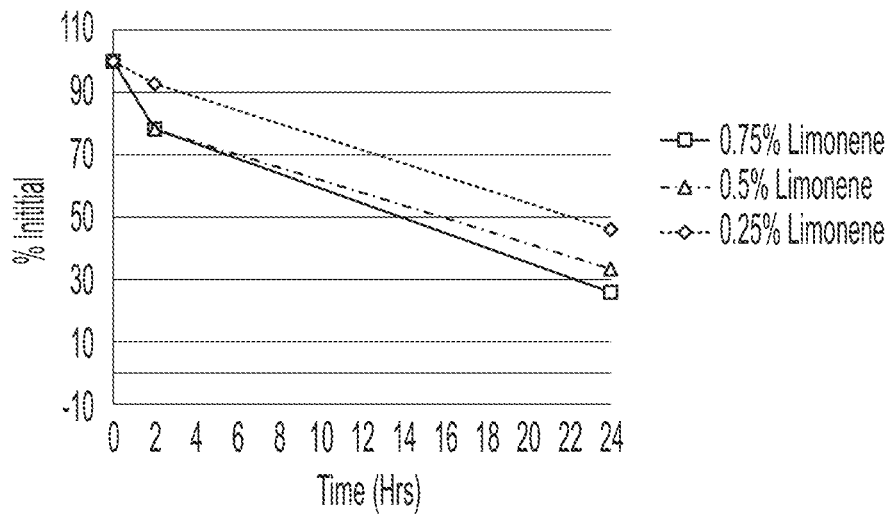
FIG. 14 shows a graph providing an evaluation of d50 particle size of hydrophobic coated API with various concentrations of pure limonene.
Figure 15:
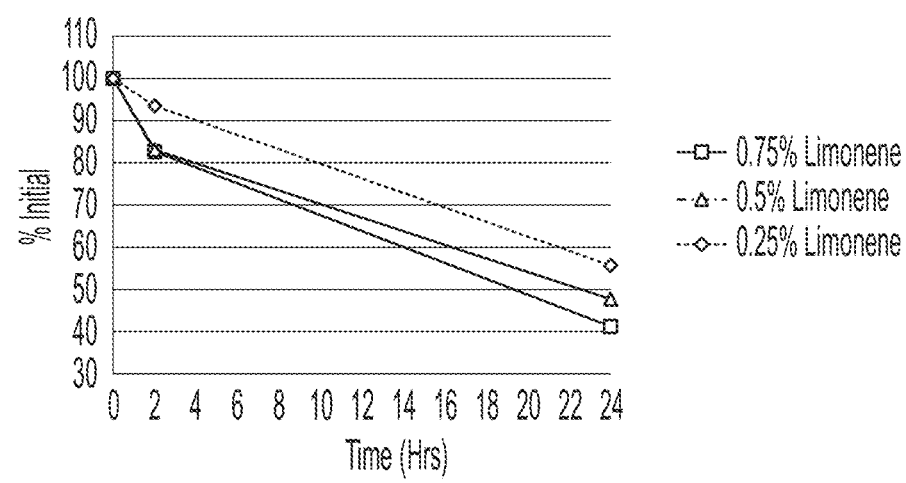
FIG. 15 shows a graph providing an evaluation of d90 particle size of hydrophobic coated API with various concentrations of pure limonene.

Example 9: FIGS. 13, 14, and 15 provide data on the decrease in d10, d50, and d90 particle size, respectively, of the hydrophobic coated Ibuprofen for the specific component limonene, which is found in some liquid flavors. These tests were conducted to explore the behaviors of the specific component of the liquid flavor, limonene, on hydrophobic coated Ibuprofen in suspension. Note that the concentrations of limonene shown in the Figures are significantly greater than the concentration of limonene that would be present if a liquid flavor was used. In FIGS. 13-15, pure limonene was used in concentrations of 0.25% w/w, 0.45% w/w, and 0.75% w/w and tested over a period of 24 hours. As shown across all three Figures, a limonene concentration of 0.25% w/w had a much less deleterious effect on the coating of the hydrophobic coated Ibuprofen particle size than limonene concentration of 0.45% w/w and 0.75% w/w. Further, the pharmaceutical suspensions tested with 0.25% w/w limonene comprised a sufficiently low amount of aeration. Accordingly, these tests confirm that limonene of the liquid orange flavor tested in FIGS. 10-12 are at least partially responsible for minimizing the aeration of the pharmaceutical suspension and subsequently eroding the coating of the hydrophobic coated Ibuprofen in relatively high quantities and/or at relatively high exposure times.

Figure 16:
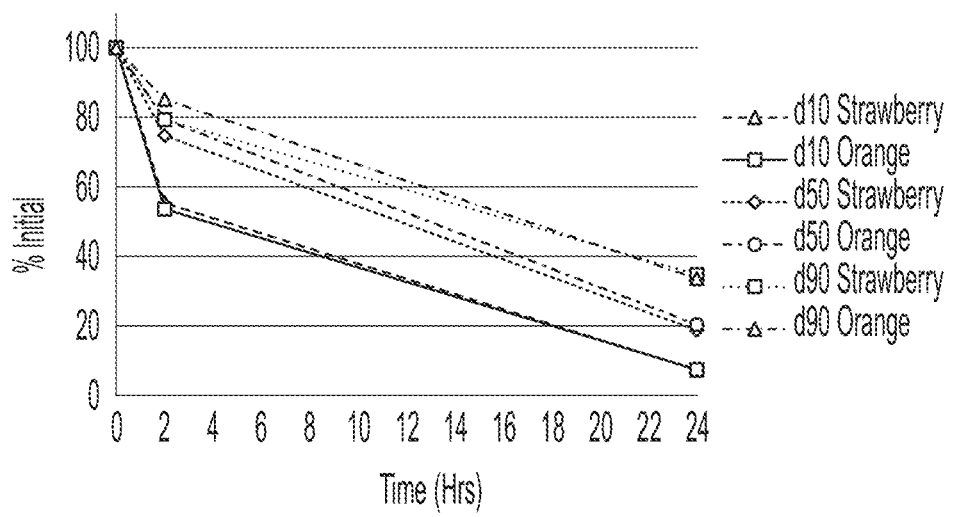
FIG. 16 shows a graph comparing the various particle size analyses of hydrophobic coated API with strawberry and orange liquid flavors.

Example 10: FIG. 16 shows testing data of two different liquid flavors—strawberry and orange. D10, d50, and d90 particle sizes of the hydrophobic coated Ibuprofen were tested for both strawberry liquid flavor and orange liquid flavor. Both strawberry and orange liquid flavors comprise limonene. As shown in the Figure, both flavors behave similarly with regards to hydrophobic coated Ibuprofen particle size. The d10 particle samples showed a greater amount of particle size decrease within the first two hours of the trial than the d50 and d90 particle size samples. The d50 and d90 particle size samples exhibited less of a particle size decrease within the same two-hour period. However, this observation is consistent with the data of d10, d50, and d90 particle sizes of the previously-discussed examples.

Additionally, it was observed in all trials that as the particle size of the hydrophobic coated API (Ibuprofen) particles decreased, a separate population of particles comprising a particle size of 5 μm to 20 μm appeared and increased with time. These particles are believed to be non-deformable coating material particles embedded within the deformed, continuous coating material prior to erosion of the coating due to shear forces. Accordingly, as the coating erodes, and the particle size of the hydrophobic coated Ibuprofen decreases, the population size of these smaller particles increases as the deformed coating material surrounding them erodes, causing these non-deformable particles to release from the hydrophobic coated Ibuprofen.

Overall, these trials show that by optimizing the amount of the terpene limonene to add to the pharmaceutical suspension comprising hydrophobic coated Ibuprofen, the amount of aeration in the suspension can be minimized to permit downstream processing while at the same time not having an adverse effect on the coating of the hydrophobic coated Ibuprofen (as determined by the particle size of the hydrophobic coated Ibuprofen.)

Coating with and without Water Soluble Excipients

Applicants also tested whether the coated API would be better with a first coating of carnauba wax alone verses coated with carnauba wax and hydroxypropyl cellulose (i.e., a soluble excipient). These tests showed that without the soluble coating excipient, better Ibuprofen particles were produced. At the time of these tests, Cellets 350 were used as coating media to aid the coating process.

Batches of coated Ibuprofen were manufactured in 3 stages on a LabRAM acoustic mixer as follows: (1) For the first stage of mixing 14 g of pre-sieved 75-250 μm Ibuprofen API, 1.82 g carnauba wax (used as the coating polymer), and 10.36 g Cellets 350 microcrystalline cellulose (used as a coating media) were added to a 125 ml plastic vessel. For batches Z3703/136/07 and 09, 0.5 g of the water soluble excipient hydroxypropyl cellulose (HPC) SSL micronized was also added. Coating was then conducted at an acceleration of 88 G for 15 minutes; (2) Upon completion of the first coating stage an additional 1.82 of carnauba wax was added to the mixing vessel, and where applicable (batches Z3703/136/07 and 09) another 0.5 g aliquot of HPC SSL micronized was added. Coating was then resumed at 88 G for a further 15 minutes (second coating stage); (3) Upon completion of the second coating stage, 1 g of silica hydrophobic (Aerosil R972) was added to the mix as a flow aid. Coating was then resumed at 88 G for a further 1 minute; and (4) After coating the intermediate product was post sieved to <250 μm and the post sieved coated API analysed under the microscope to determine the level of coating achieved. The following Table 10 provides an assessment of the coating from microscopic testing:

TABLE 10

| Batch Reference | Water Soluble Excipient (% in formulation) | API | Coating Polymer | Assessment of Coating from Microscopic Testing |
| --- | --- | --- | --- | --- |
| Z3703/136/07 | HPC SSL micronized (3.33) | Ibuprofen | Carnauba Wax | Moderate coating |
| Z3703/136/09 | | | | Moderate coating |
| Z3703/136/10 | N/A | | | Good coating |
| Z3703/136/12 | | | | Good coating |

In addition, FIGS. 19A-B, 20A-B, 21A-B, and 22A-B provide SEM images of batches Z3703/136/07, Z3703/136/09, Z3703/136/10, and Z3703/136/12, respectively. The microscopic analysis of comparable batches manufactured with and without the water soluble excipient HPC demonstrated that the presence of the water soluble material did not result in an improvement in coating performance. In contrast, batches manufactured without HPC were observed to have an improved level of coating, with increased polymer deformation onto the surface of the API observed and reduced levels of unbound coating materials. A coating process without a water soluble material was therefore concluded to be a process improvement compared to batches manufactured with a water soluble excipient.

Coating with and without Coating Media

Applicants also tested coating Ibuprofen with and without a coating media. The quality of the coat was assessed by dissolution test on the percent release of Ibuprofen from the coated particles over 5 minutes. The test showed that the use of a coating media offered no benefit with respect to the coating. In addition, it resulted in lower yield.

Batches of coated Ibuprofen were manufactured in 2 stages on a RAM2 acoustic mixer as follows:

Batches Z4592/73/04 and 09: For the first stage of coating, (which was conducted at a batch size of 201.81 g), 48% w/w pre-sieved >75 μm Ibuprofen API, 35% w/w Cellets 350 microcrystalline cellulose (used as a coating media) and 16% w/w coating polymer (carnauba wax for batch Z4592/73/04 and sasol wax for Z4592/73/09) were added to a 530 ml stainless jacketed inner vessel. Coating was then conducted at an acceleration of 85 G for 10 minutes at the specified mix temperature set-point (53° C. for Z4592/73/04 and 47° C. for Z4592/73/09), with water cooling used to provide temperature control. Upon completion of the first coating stage 1% w/w silica hydrophobic (Aerosil R972) was added to the mix as a flow aid. Coating was then resumed at an acceleration of 80 G for 30 seconds. After coating the intermediate product was post sieved to 75-250 μm and the post sieved coated API analysed by dissolution testing to determine the level of coating achieved.

Figure 23:
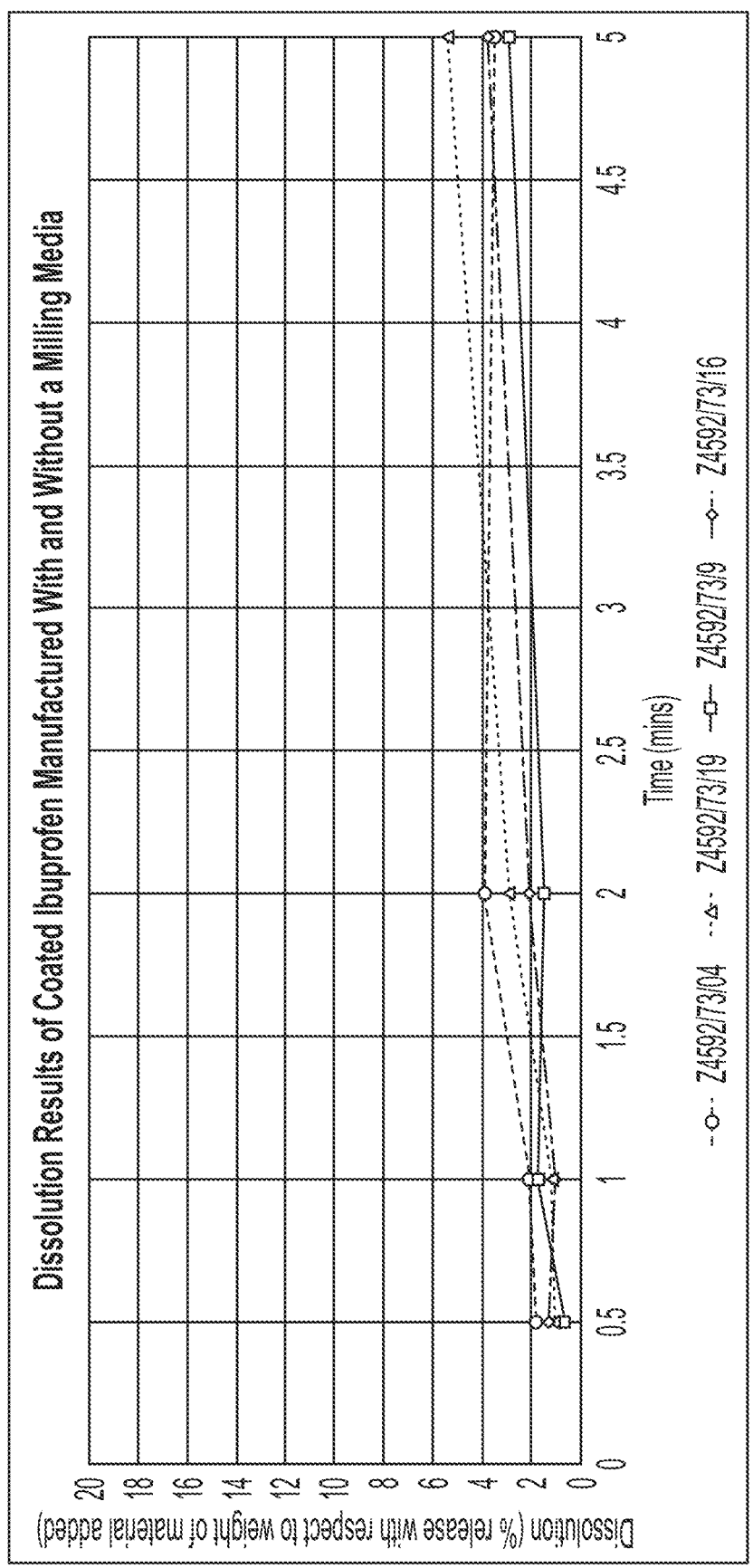
FIG. 23 is a chart with dissolution results of the coated API manufactured with and without a coating (i.e., milling) media as explained in the Examples.

Batches Z4592/73/16 and 19: For the first coating stage (which was conducted at batch sizes of 193.19 g and 140.67 g for batches Z4592/73/16 and Z4592/73/19 respectively), 77.87% w/w pre-sieved >75 μm Ibuprofen API and 21.13% w/w coating polymer (sasol wax for batch Z4592/73/16 and carnauba wax for Z4592/73/19) were added to a 530 ml stainless jacketed inner vessel. Coating was then conducted at accelerations of 97 G (Z4592/73/16) and 98 G (Z4592/73/19) for 20 minutes at the specified mix temperature set-point (47° C. for Z4592/73/16 and 56° C. for Z4592/73/19), with water cooling used to provide temperature control. Upon completion of the first coating stage 1% w/w silica hydrophobic (Aerosil R972) was added to the mix as a flow aid. Mixing was then resumed at an acceleration of 80 G for 30 seconds. After coating the intermediate product was post sieved to 75-250 μm and the post sieved coated API analysed by dissolution testing to determine the level of coating achieved. The following Table 11 provides the results of these tests. In addition, the dissolution results of the coated Ibuprofen manufactured with and without a coating (i.e., milling) media is shown in FIG. 23.

TABLE 11

| Batch Reference | Milling Media? (Y/N) | API | Coating Polymer | Dissolution (% release with respect to weight of material added) | | | | Yield Desired 75-250 μm Coated API (%) |
| --- | --- | --- | --- | --- | --- | --- | --- | --- |
| | | | | 30 secs | 1 min | 2 mins | 5 mins | |
| Z4592/73/04 | Y | Ibuprofen | Carnauba Wax | 1.8 | 2.1 | 3.9 | 3.5 | 49.1 |
| Z4592/73/19 | N | | | 1.1 | 1.2 | 2.9 | 5.4 | 84.5 |
| Z4592/73/09 | Y | | Sasol Wax | 0.7 | 1.7 | 1.5 | 2.9 | 48.2 |
| Z4592/73/16 | N | | | 1.3 | 1.1 | 2.1 | 3.8 | 89.7 |

The dissolution results for coated ibuprofen manufactured with and without a coating media, and using two different coating polymers, show a similar rate of release for all batches, with results at all time-points within the limits of analytical variation. It can therefore be concluded that a similar level of coating has been achieved for all batches, with the coating media offering no improvement to the coating process. The yield of 75-250 μm coated API obtained after post sieving the coated API demonstrates a significant increase on batches manufactured without a coating media. A coating process without a coating media was therefore concluded to be a process improvement compared to batches manufactured with a coating media.

Measuring Dissolution

Low Volume Dissolution (LVD) 5-Minute Profile

The analytical method used to determine the low volume dissolution of Active Pharmaceutical Ingredient (API) raw material and coated API material is described below. The method employs the Pion Rainbow Dynamic Dissolution Monitor (RDDM) and Mini-bath (MB8), at 75 rpm, with 0.01% w/v SDS in pH 7.2 phosphate buffer as a dissolution medium using a 5 mm pathlength. Pathlength and dissolution media will vary depending on the API properties. Analysis is by fiber optic UV detection using the Pion μDISS Profiler with a UV detection under the $2^{nd}$ derivative function and will vary depending on the chromophore of the API and its spectral response within the software. The UV detection range of 277-287 nm has been established for Ibuprofen. A five-point calibration Curve is set up on the Pion software. The amount of API reference standard weighed will be dependent on the API. The following is an example for Ibuprofen:

Calibration Point 1: Weigh accurately 15.0 mg (14.3-15.7 mg) of Ibuprofen reference standard into a 100 mL volumetric flask. Dissolve in approximately 20 mL of dissolution media and sonicate for at least 5 minutes to fully dissolve. Dilute to volume with dissolution media mixing thoroughly. This is the calibration point 1 working standard solution (concentration: approximately 0.15 mg/mL).

Calibration Point 2: Weigh accurately 20.0 mg (19.0-21.0 mg) of Ibuprofen reference standard into a 100 mL volumetric flask. Dissolve in approximately 20 mL of dissolution media and sonicate for at least 5 minutes to fully dissolve. Dilute to volume with dissolution media mixing thoroughly. This is the calibration point 2 working standard solution (concentration: approximately 0.20 mg/mL).

Calibration Point 3: Weigh accurately 30.0 mg (28.5-31.5 mg) of Ibuprofen reference standard into a 100 mL volumetric flask. Dissolve in approximately 20 mL of dissolution media and sonicate for at least 5 minutes to fully dissolve. Dilute to volume with dissolution media mixing thoroughly. This is the calibration point 3 working standard solution (concentration: approximately 0.30 mg/mL).

Calibration Point 4: Weigh accurately 40.0 mg (38.0-42.0 mg) of Ibuprofen reference standard into a 100 mL volumetric flask. Dissolve in approximately 20 mL of dissolution media and sonicate for at least 5 minutes to fully dissolve. Dilute to volume with dissolution media mixing thoroughly. This is the calibration point 4 working standard solution (concentration: approximately 0.40 mg/mL).

Calibration Point 5: Weigh accurately 60.0 mg (57.0-63.0 mg) of Ibuprofen reference standard into a 100 mL volumetric flask. Dissolve in approximately 20 mL of dissolution media and sonicate for at least 5 minutes to fully dissolve. Dilute to volume with dissolution media mixing thoroughly. This is the calibration point 5 working standard solution (concentration: approximately 0.60 mg/mL).

Samples Analysis

Ibuprofen Raw material: Six samples are analyzed. For each sample, weigh accurately 40 mg±1.0% of Ibuprofen raw material into each Pion low volume dissolution vessel. A mean sample weight of the 6 vessels is used for the instrument potency calculation.

Coated Ibuprofen material: Six samples are analyzed. For each sample, weigh accurately 50 mg*±1.0% of Ibuprofen coated material into a Pion low volume dissolution vessel. A mean sample weight of the 6 vessels is used for the instrument potency calculation. (*50 mg of coated material adjusted for the potency of the coated API as required.)

For each experiment run, a staggered dissolution media addition of 10 ml and magnetic stirrer start must be performed to keep each dissolution vessel condition consistent. The samples are automatically analyzed via fiber optic UV detection at specified timepoints and intervals which can be selected as required. The six probes will measure the absorbance of the API in the vessels and determine the % drug dissolved based on the calibration curve. 100% drug dissolved equates to a final solution concentration of ~4 mg/mL.

Low Volume Dissolution (LVD) 60-Minute Profile

The following analytical method is used to determine the low volume dissolution of API raw material and coated API material. The method employs the Pion Rainbow Dynamic Dissolution Monitor (RDDM) and Mini-bath (MB8), at 75 rpm, with 0.01% w/v SDS in pH 7.2 phosphate buffer as a dissolution medium. Analysis is by fibre optic UV detection using the Pion μDISS Profiler with a UV detection under the $2^{nd}$ derivative function using a 2 mm pathlength. Pathlength, dissolution media and wavelength range will vary depending on the API properties. The UV detection range of 277-287 nm has been established for Ibuprofen. A five-point calibration Curve is set up on the Pion software. The amount of API reference standard weighed will be dependent on the API. The following is an example for Ibuprofen:

Calibration Point 1: Weigh accurately 40.0 mg (38.0-42.0 mg) of Ibuprofen reference standard into a 100 mL volumetric flask. Dissolve in approximately 80 mL of dissolution media and sonicate until fully dissolved. Dilute to volume with dissolution media mixing thoroughly. This is the calibration point 1 working standard solution (concentration: approximately 0.4 mg/mL).

Calibration Point 2: Weigh accurately 100.0 mg (95.0-105.0 mg) of Ibuprofen reference standard into a 100 mL volumetric flask. Dissolve in approximately 80 mL of dissolution media and sonicate until fully dissolved. Dilute to volume with dissolution media mixing thoroughly. This is the calibration point 2 working standard solution (concentration: approximately 1.0 mg/mL).

Calibration Point 3: Weigh accurately 300.0 mg (285.0-315.0 mg) of Ibuprofen reference standard into a 100 mL volumetric flask. Dissolve in approximately 80 mL of dissolution media and sonicate until fully dissolved. Dilute to volume with dissolution media mixing thoroughly. This is the calibration point 3 working standard solution (concentration: approximately 3.0 mg/mL).

Calibration Point 4: Weigh accurately 400.0 mg (380.0-420.0 mg) of Ibuprofen reference standard into a 100 mL volumetric flask. Dissolve in approximately 80 mL of dissolution media and sonicate until fully dissolved. Dilute to volume with dissolution media mixing thoroughly. This is the calibration point 4 working standard solution (concentration: approximately 4.0 mg/mL).

Calibration Point 5: Weigh accurately 440.0 mg (418.0-462.0 mg) of Ibuprofen reference standard into a 100 mL volumetric flask. Dissolve in approximately 80 mL of dissolution media and sonicate until fully dissolved (this standard solution may require slight heating to dissolve all Ibuprofen). If required, allow the solution to equilibrate to room temperature, dilute to volume with dissolution media and mix thoroughly. This is the calibration point 5 working standard solution (concentration: approximately 4.4 mg/mL).

Sample Analysis

Ibuprofen raw material: Six samples are analyzed. For each sample, weigh accurately 40 mg±1.0% of Ibuprofen raw material into a Pion low volume dissolution vessel. A mean sample weight of the 6 vessels is used for the instrument potency calculation.

Ibuprofen coated material: Six samples are analyzed. For each sample, weigh accurately 50 mg*±1.0% of Ibuprofen coated material into a Pion low volume dissolution vessel. A mean sample weight of the 6 vessels is used for the instrument potency calculation. (*50 mg of coated material adjusted for the potency of the coated API as required.)

This method allows for a full profile up to complete release of material to 100% dissolved. For each experiment run, a staggered dissolution media addition of 10 ml and magnetic stirrer start must be performed to keep each dissolution vessel condition consistent. The samples are automatically analyzed via fiber optic UV detection at specified timepoints and intervals which can be selected as required. The six probes will measure the absorbance of the API in the vessels and determine the % drug dissolved based on the calibration curve. 100% drug dissolved equates to a final solution concentration of ~4 mg/mL.

Mid Volume Dissolution (MVD) 60-Minute Profile

This analytical method is used to determine the mid-volume dissolution of freeze-dried finished products. The method employs a Distek small volume conversion kit. The method employs the Pion Rainbow Dynamic Dissolution Monitor (RDDM) at 75 rpm, with pH 7.2 phosphate buffer as a dissolution medium. Analysis is by fibre optic UV detection using the Pion μDISS Profiler with a UV detection under the $2^{nd}$ derivative function using a 2 mm pathlength. Pathlength, dissolution media and wavelength range will vary depending on the API properties. The UV detection range of 275-285 nm has been established for ibuprofen. A five-point calibration Curve is set up on the Pion software. The amount of API reference standard weighed will be dependent on the API. The following is an example for Ibuprofen:

Calibration Point 1: Weigh accurately 40.0 mg (38.0-42.0 mg) of Ibuprofen reference standard into a 100 mL volumetric flask. Dissolve in approximately 80 mL of dissolution media and sonicate until fully dissolved. Dilute to volume with dissolution media mixing thoroughly. This is the calibration point 1 working standard solution (concentration: approximately 0.4 mg/mL).

Calibration Point 2: Weigh accurately 100.0 mg (95.0-105.0 mg) of Ibuprofen reference standard into a 100 mL volumetric flask. Dissolve in approximately 80 mL of dissolution media and sonicate until fully dissolved. Dilute to volume with dissolution media mixing thoroughly. This is the calibration point 2 working standard solution (concentration: approximately 1.0 mg/mL).

Calibration Point 3: Weigh accurately 300.0 mg (285.0-315.0 mg) of Ibuprofen reference standard into a 100 mL volumetric flask. Dissolve in approximately 80 mL of dissolution media and sonicate until fully dissolved. Dilute to volume with dissolution media mixing thoroughly. This is the calibration point 3 working standard solution (concentration: approximately 3.0 mg/mL).

Calibration Point 4: Weigh accurately 400.0 mg (380.0-420.0 mg) of Ibuprofen reference standard into a 100 mL volumetric flask. Dissolve in approximately 80 mL of dissolution media and sonicate until fully dissolved. Dilute to volume with dissolution media mixing thoroughly. This is the calibration point 4 working standard solution (concentration: approximately 4.0 mg/mL).

Calibration Point 5: Weigh accurately 440.0 mg (418.0-462.0 mg) of Ibuprofen reference standard into a 100 mL volumetric flask. Dissolve in approximately 80 mL of dissolution media and sonicate until fully dissolved (this standard solution may require slight heating to dissolve all Ibuprofen). If required, allow the solution to equilibrate to room temperature, dilute to volume with dissolution media and mix thoroughly. This is the calibration point 5 working standard solution (concentration: approximately 4.4 mg/mL).

Sample Analysis

As per USP <711>—A small, loose piece of non-reactive material, such as not more than a few turns on wire helix, may be attached to the freeze-dried tablets that would otherwise float. Add one freeze-dried tablet to each of the six dissolution vessels. The six probes will measure the absorbance of the API in the vessels and determine the % drug dissolved based on the calibration curve.

Dissolution Example 1: Comparison of Ibuprofen Raw Material and Coated Ibuprofen Raw Material by Low Volume 5-Minute Dissolution Test An assessment of the effectiveness of the coating process for taste masking Ibuprofen in a freeze-dried tablet is made by comparing the % release of ibuprofen in a low volume dissolution test over 5 minutes for coated ibuprofen with uncoated ibuprofen raw material.

The uncoated Ibuprofen was sieved before being coated. The API was coated using the Resonance Acoustic Mixing (RAM II scale) manufacture process and was sieved after coating. The sieved coated Ibuprofen is used for the manufacture of freeze dried tablets of dosage strengths 200 mg, 100 mg and 50 mg with taste masked properties whist remaining compliant with the dissolution requirement that complies with USP<711> and Ph. Eur.2.9.3 criteria, with not less than 85% released at 60 minutes. The composition of the freeze dried tablets tested are shown in the following Table 12.

All ibuprofen dissolution data provided was from the 200 mg dosage strength composition.

Sample analysis: Ibuprofen Raw material: 40 mg of ibuprofen raw material was accurately weighed into each sample vial, 10 ml of 0.01% w/v SDS in pH 7.2 phosphate buffer added at 30 second intervals. Experiment run with Pion µDISS Profiler. Auto calculation of % dissolved based on calibration curve. Ibuprofen Coated material: 50 mg of ibuprofen coated material was accurately weighed into each sample vial, 10 ml of 0.01% w/v SDS in pH 7.2 phosphate buffer added at 30 second intervals. Experiment run with Pion µDISS Profiler. Auto calculation of % dissolved based on calibration curve.

Figure 24:
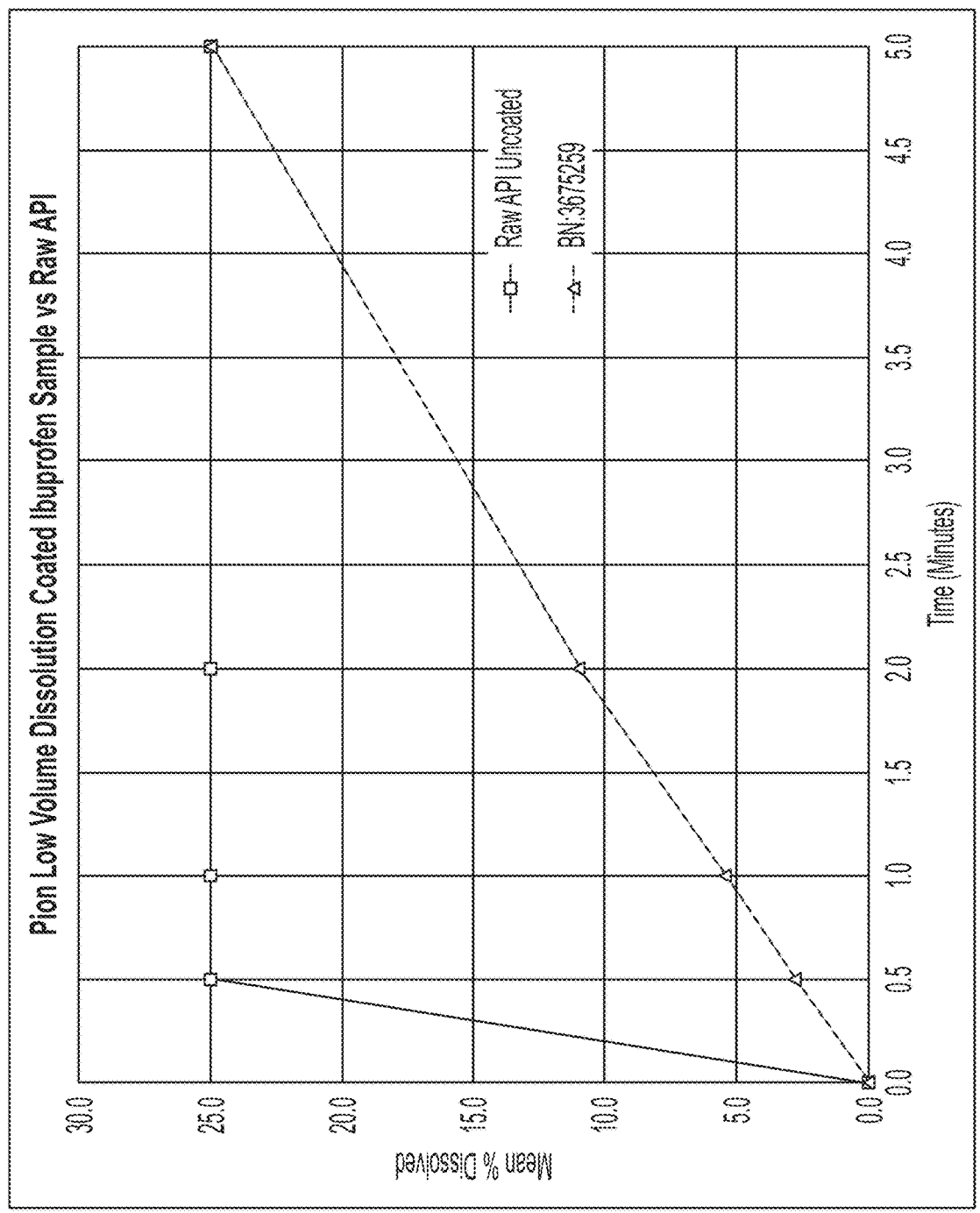
FIG. 24 is a chart comparing API raw material and coated API raw material using the low volume 5-minute dissolution test.

The % ibuprofen dissolved results for both experiments are detailed in Table 13. This method has an upper detection limit of 25% drug dissolved due to the size of the probe tips used. Results greater than 25% are reported as >25%. The ibuprofen raw material is freely able to dissolve and reached the maximum quantifiable value for the method at the 30 second timepoint, (25%). This then remains constant for the remaining timepoints. The coated ibuprofen material has a slower profile as the coating is preventing the immediate dissolution of the API. At 30 seconds only 2.8% of ibuprofen is released compared to >25% for the ibuprofen raw material. This is a significant difference. At the two-minute point the coated ibuprofen is still significantly less dissolved at 11% dissolved. By 5 minutes the coated ibuprofen has also reached the maximin quantifiable threshold of the method at 25%. This data has been represented in FIG. 24.

TABLE 13

(Comparison of Ibuprofen raw material and coated Ibuprofen raw material by low volume 5-minute Dissolution Test)

| Time (minutes) | % Ibuprofen Dissolved | |
| --- | --- | --- |
| | Raw Material | Coated batch 3675259 |
| 0.0 | 0 | 0.0 |
| 0.5 | >25 | 2.8 |
| 1 | >25 | 5.5 |

TABLE 12

| Coated Ibuprofen suspension (Dosing ratio) | | (Dosing ratio of 40:60) | Freeze Dried Tablet | Freeze Dried Tablet 200 mg dose | Freeze Dried Tablet 100 mg dose | Freeze Dried Tablet 50 mg dose |
| --- | --- | --- | --- | --- | --- | --- |
| Component | Function | % w/w | % w/w | Qty per tablet (mg) | Qty per tablet (mg) | Qty per tablet (mg) |
| Coated Ibuprofen | API | 40 | 88.71 | 264.056 | 132.028 | 66.014 |
| Ibuprofen | API | 31 | 68.75 | 204.6434 | 102.3217 | 51.1609 |
| Carnauba Wax | 1st coating | 8.4 | 18.63 | 55.4518 | 27.7259 | 13.8629 |
| Silica hydrophobic colloidal | 2nd coating/ flow aid | 0.6 | 1.33 | 3.96084 | 1.9804 | 0.9902 |
| Gelatin | Matrix Former | 2.4 | 5.32 | 15.8434 | 7.9217 | 3.9609 |
| Mannitol | Structure Former | 1.8 | 4 | 11.8825 | 5.9413 | 2.9706 |
| Xanthan gum | Viscosity modifier | 0.05 | 0.11 | 0.3169 | 0.1584 | 0.0792 |
| Sucralose | Sweetener | 0.24 | 0.53 | 1.5843 | 0.7922 | 0.3961 |
| Orange Flavor | Flavoring | 0.6 | 1.33 | 3.9608 | 1.9804 | 0.9902 |
| Purified water | Dispersing agent | 54.9 | | | | |

TABLE 13-continued (Comparison of Ibuprofen raw material and coated Ibuprofen raw material by low volume 5-minute Dissolution Test)

| | % Ibuprofen Dissolved | |
|---|---|---|
| Time (minutes) | Raw Material | Coated batch 3675259 |
| 2 | >25 | 11.0 |
| 5 | >25 | 25.0 |

The delayed release shows the effectiveness of the coating manufacture. The difference is significant and would be indicative of taste masking of the Ibuprofen API. Proposed specification is for coated material to be <25% drug release. The results of the low volume dissolution test clearly showed a delayed release of <25% in drug substance within the first 5 mins from coated ibuprofen. In contrast, the uncoated ibuprofen showed a rapid release of drug substance within 30 seconds. The significance difference in % release of the drug substance is indicative of the effectiveness of the coating process to taste mask ibuprofen.

In some embodiments, the coated API disclosed herein has a low volume 5-minute dissolution test result of less than or equal to about 35%, about 30%, about 25%, about 20%, or about 15% drug release after 5 minutes.

Dissolution Example 2: Comparison of Ibuprofen Raw Material and Coated Ibuprofen Raw Material by Low Volume 60-Minute Dissolution Test In order to make a more detailed assessment of the coating efficiency, coated Ibuprofen batch of Dissolution Example 1 has undergone additional evaluation using the low volume dissolution (LVD) over 60 minutes.

Figure 25:
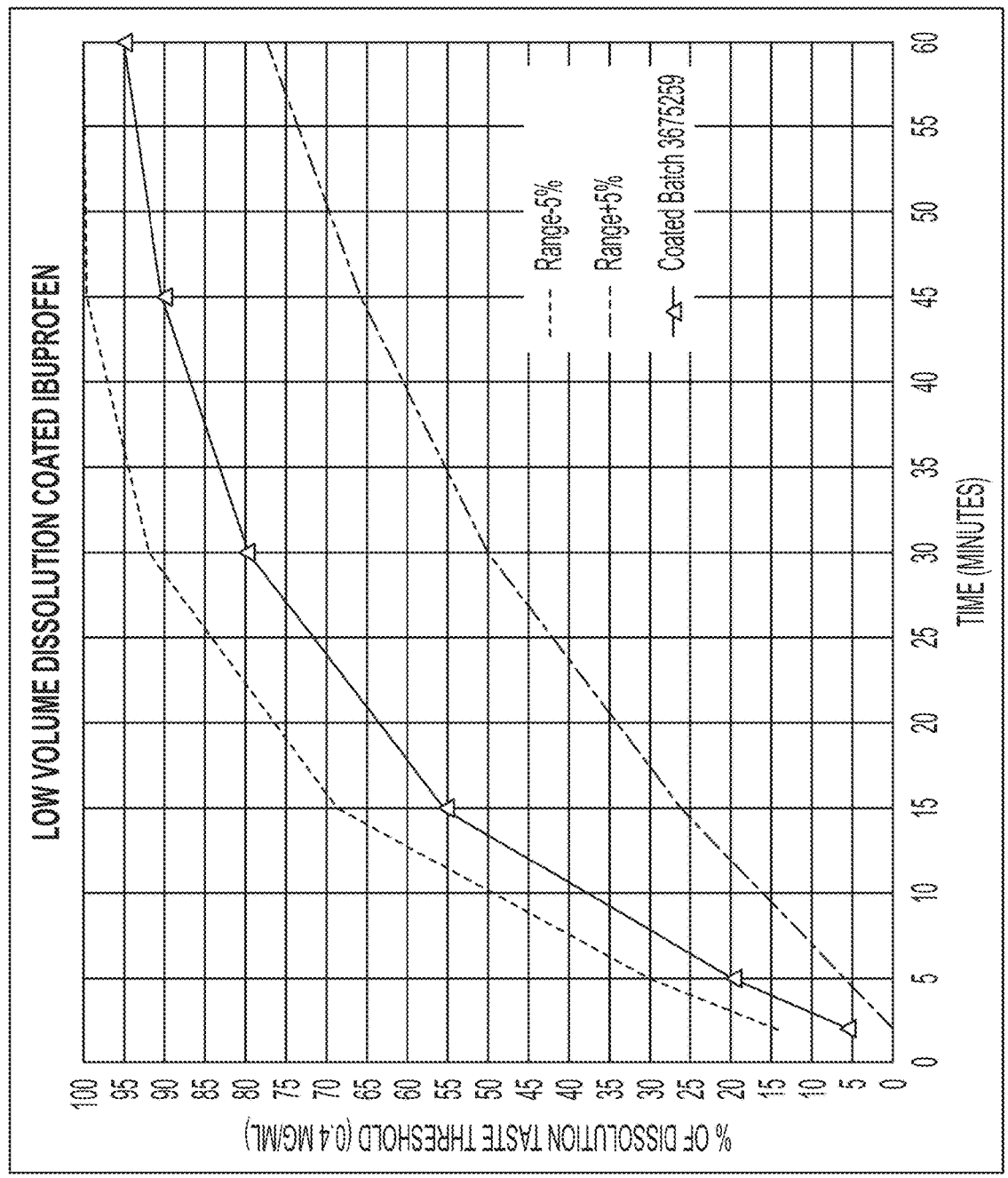
FIG. 25 is a chart illustrating a coated API Dissolution Profile over a 60 minute timeframe as disclosed herein.

Sample analysis: Coated material: 50 mg of coated ibuprofen material was accurately weighed into each sample vial, 10 ml of 0.01% w/v SDS in pH 7.2 phosphate buffer added at 30 second intervals. Experiment run with Pion µDISS Profiler. Auto calculation of % dissolved based on calibration curve. The % drug dissolved results for the experiment for the coated Ibuprofen API is detailed in Table 14. This method is no longer limited by an upper detection limit of 25% as described for the 5 min test. Instead the profile can be accurately monitored across the 60 minutes until ~100% dissolved is achieved. Whilst the software can record % drug dissolved at as many timepoints as specified for this experiment the following timepoints were considered the most appropriate to report 2, 5, 15, 30, 45 and 60 minutes. Note: Raw material Ibuprofen reaches 100% dissolved by ~2 mins. The coated Ibuprofen material has a slower profile as the coating is preventing the immediate dissolution of the API. At the two-minute timepoint the coated API is still significantly less dissolved at 6% dissolved. The profile then continues on a slow release trajectory and at 60 minutes has achieved 95% release. LVD of the coated material gave a slow release profile up to 15 minutes indicative of taste masking. This data has been represented in FIG. 25, along with the ±5% error bars and Table 14.

TABLE 14

(Coated Ibuprofen Dissolution Profile over 60 minutes timeframe)

| | % Released | | | | |
|---|---|---|---|---|---|
| Time (minutes) | Vessels Min | Vessels Max | Lower Range | Upper Range | Mean |
| 2 | 3 | 9 | 0 | 15 | 6 |
| 5 | 11 | 25 | 5 | 30 | 20 |
| 15 | 31 | 64 | 25 | 70 | 56 |
| 30 | 55 | 87 | 50 | 95 | 80 |
| 45 | 71 | 95 | 70 | 100 | 90 |
| 60 | 82 | 97 | 75 | 100 | 95 |

The data shows that the slow release profile of the coated material which is evidence of taste masking. The delayed release is a result of the efficacy of the coating manufacture. Proposed specification is for coated material to be less than or equal to 70% drug release at 15 minutes.

In some embodiments, the coated API disclosed herein has a low volume 60-minute dissolution test result of less than or equal to about 85%, about 80%, about 75%, about 70%, about 65%, or about 60%, or about 55% or about 50% or about 45% after 15 minutes. In some embodiments, the coated API disclosed herein has a low volume 60-minute dissolution test result of less than or equal to about 95%, about 90%, about 85%, about 80%, about 75%, or about 70% after 30 minutes. In some embodiments, the coated API disclosed herein has a low volume 60-minute dissolution test result of less than or equal to about 95%, about 90%, about 85%, or about 80% after 45 minutes. In some embodiments, the coated API disclosed herein has a low volume 60-minute dissolution test result of less than or equal to about 99%, about 98%, about 95%, or about 90% after 60 minutes.

Dissolution Example 3: Comparison of Ibuprofen Coated Ibuprofen Material and Finished Product by Mid Volume 60-Minute Dissolution Test Coated Ibuprofen is then taken through the dosage form manufacturing process resulting in the finished product units. An additional methodology Mid Volume Dissolution (MVD) based on the 60-minute profile for the coated API has been developed to be able to directly compare dissolution profiles of the coated API with the resulting finished product units. This allows a direct comparison between the coated properties of the API and within the finished product ODT.

Figure 26:
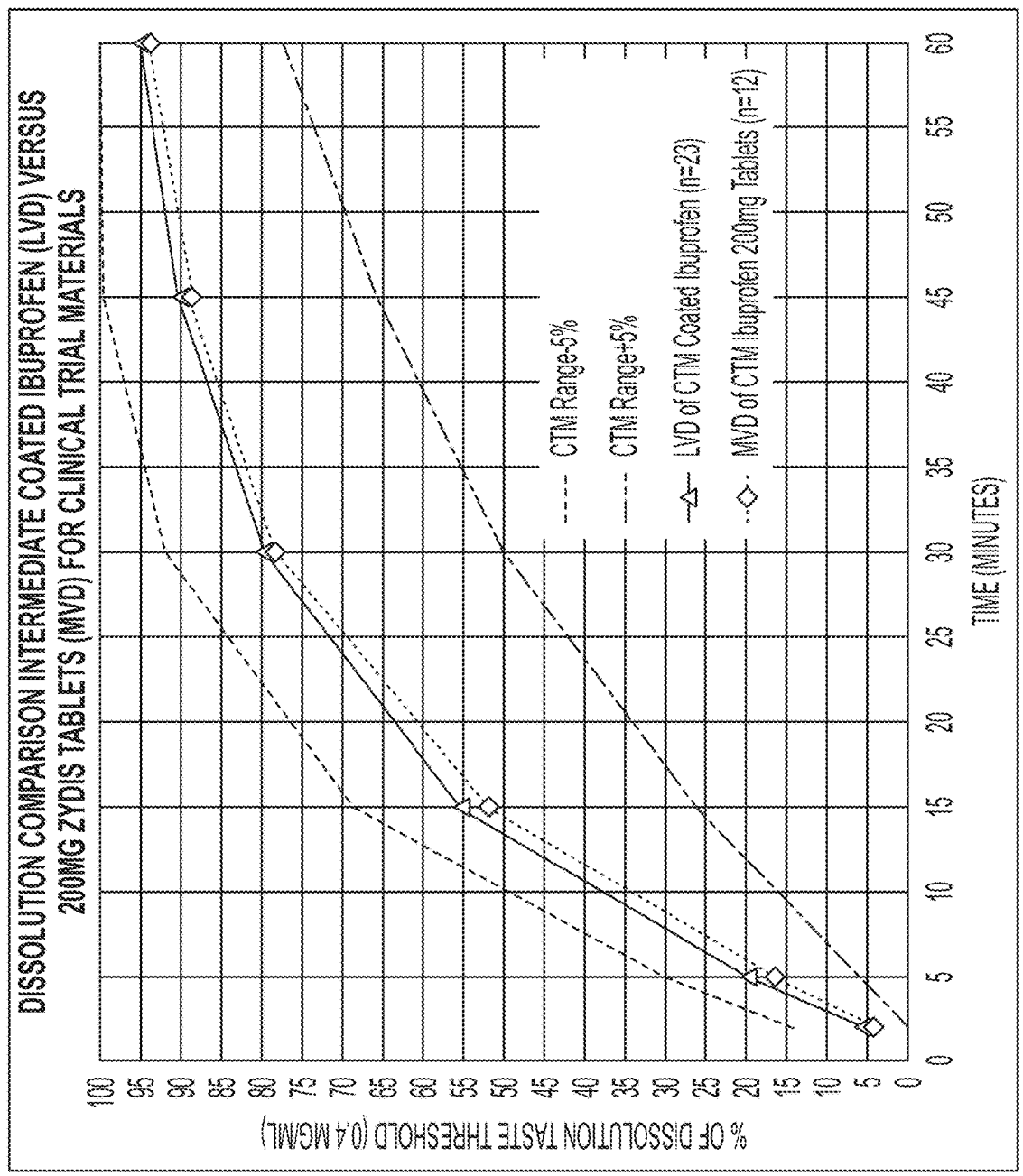
FIG. 26 is a chart illustrating a Dissolution comparison of coated API (LVD) and 200 mg finished product (MVD) as described herein.

The MVD data for Ibuprofen 200 mg finished product from Dissolution Example 1 (Table 12) and the LVD data from the respective coated Ibuprofen can now be overlaid as in FIG. 26. (Note: Uncoated material achieves a full release of ~80% within ~5 mins). As can be seen by these data, the Ibuprofen finished product has a slow release profile which is in good agreement with the preceding coated Ibuprofen. The finished product has values for % drug released within ±5% of the coated ibuprofen at each of the reported timepoints i.e. 2, 5, 15, 30, 45 and 60 minutes. The slow release of the finished product is evidence of coated Ibuprofen having maintained its integrity during the manufacturing process and producing a taste masked finished product unit. Proposed specifications: less than 70% drug released at 15 minutes for both LVD and MVD are indicative of achieving taste masking.

TABLE 15

(Dissolution comparison coated Ibuprofen (LVD) and 200 mg finished product (MVD))

| | % Ibuprofen Dissolved | | | |
|---|---|---|---|---|
| Time (minutes) | 200 mg finished product | Coated batch 3675259 | Lower Range | Upper Range |
| 2 | 4 | 6 | 0 | 15 |
| 5 | 17 | 20 | 5 | 30 |
| 15 | 52 | 56 | 25 | 70 |
| 30 | 78 | 80 | 50 | 95 |
| 45 | 89 | 90 | 70 | 100 |
| 60 | 94 | 95 | 75 | 100 |

In some embodiments, the pharmaceutical compositions disclosed herein has a mid volume 60-minute dissolution test result of less than or equal to about 85%, about 80%, about 75%, about 70%, about 65%, about 60%, or about 55%, or about 50% or about 50%, or about 45% after 15 minutes. In some embodiments, the pharmaceutical composition disclosed herein has a mid volume 60-minute dissolution test result of less than or equal to about 95%, about 90%, about 85%, about 80%, about 75%, or about 70% after 30 minutes. In some embodiments, the pharmaceutical composition disclosed herein has a mid volume 60-minute dissolution test result of less than or equal to about 95%, about 90%, about 85%, or about 80% after 45 minutes. In some embodiments, the pharmaceutical composition disclosed herein has a mid volume 60-minute dissolution test result of less than or equal to about 99%, about 98%, about 95%, or about 90% after 60 minutes.

Dissolution Example 4 (Acetaminophen (APAP) as API)

This analytical method is used to determine the low volume dissolution of Acetaminophen raw material and coated Acetaminophen material. The method employs the Pion Rainbow Dynamic Dissolution Monitor (RDDM) and Mini-bath (MB8), at 50 rpm, with 0.01% w/v SDS in pH 7.2 phosphate buffer as a dissolution medium. Analysis is by fiber optic UV detection using the Pion µDISS Profiler with a UV detection range of 320-330 nm under the $2^{nd}$ derivative function using a 2 mm pathlength.

The following is the working standard 5-point calibration curve preparation for this Example. Calibration Point 1: Weigh accurately 50.0 mg of Acetaminophen reference standard into a 100 mL volumetric flask. Dissolve in approximately 80 mL of dissolution media and sonicate until fully dissolved. Dilute to volume with dissolution media mixing thoroughly. This is the calibration point 1 working standard solution (concentration: approximately 0.5 mg/mL). Calibration Point 2: Weigh accurately 100.0 mg of Acetaminophen reference standard into a 100 mL volumetric flask. Dissolve in approximately 80 mL of dissolution media and sonicate until fully dissolved. Dilute to volume with dissolution media mixing thoroughly. This is the calibration point 2 working standard solution (concentration: approximately 1.0 mg/mL). Calibration Point 3: Weigh accurately 200.0 mg of Acetaminophen reference standard into a 100 mL volumetric flask. Dissolve in approximately 80 mL of dissolution media and sonicate until fully dissolved. Dilute to volume with dissolution media mixing thoroughly. This is the calibration point 3 working standard solution (concentration: approximately 2.0 mg/mL). Calibration Point 4: Weigh accurately 500.0 mg of Acetaminophen reference standard into a 100 mL volumetric flask. Dissolve in approximately 80 mL of dissolution media and sonicate until fully dissolved. Dilute to volume with dissolution media mixing thoroughly. This is the calibration point 4 working standard solution (concentration: approximately 5.0 mg/mL). Calibration Point 5: Weigh accurately 550.0 mg of Acetaminophen reference standard into a 100 mL volumetric flask. Dissolve in approximately 80 mL of dissolution media and sonicate until fully dissolved (this standard solution may require slight heating to dissolve all Acetaminophen). If required, allow the solution to equilibrate to room temperature, dilute to volume with dissolution media and mix thoroughly. This is the calibration point 5 working standard solution (concentration: approximately 5.5 mg/mL).

Sample Analysis

Acetaminophen raw material: Six samples are analyzed. For each sample, weigh accurately 100 mg of Acetaminophen raw material into a Pion low volume dissolution vessel. The individual software potencies for each vessel will be input into the DissoPRO software at the start of experiment.

Acetaminophen coated material: Acetominophen (APAP) was preseived through 75 um and 250 um meshes to remove the any fine and oversized particles. It was coated with carnauba wax and hydrophobic silica. The composition of the coated APAP material is as follows:

| Component | Function | % w/w |
|---|---|---|
| APAP | API | 63.5 |
| Carnuba Wax | 1st coating | 34.2 |
| Silica hydrophobic colloidal | 2nd coating/flow aid | 2.3 |

Six samples are analyzed. For each sample, weigh accurately 125 mg of coated Acetaminophen material into a Pion low volume dissolution vessel. The individual software potencies for each vessel will be input into the DissoPRO software at the start of experiment.

Figure 27:
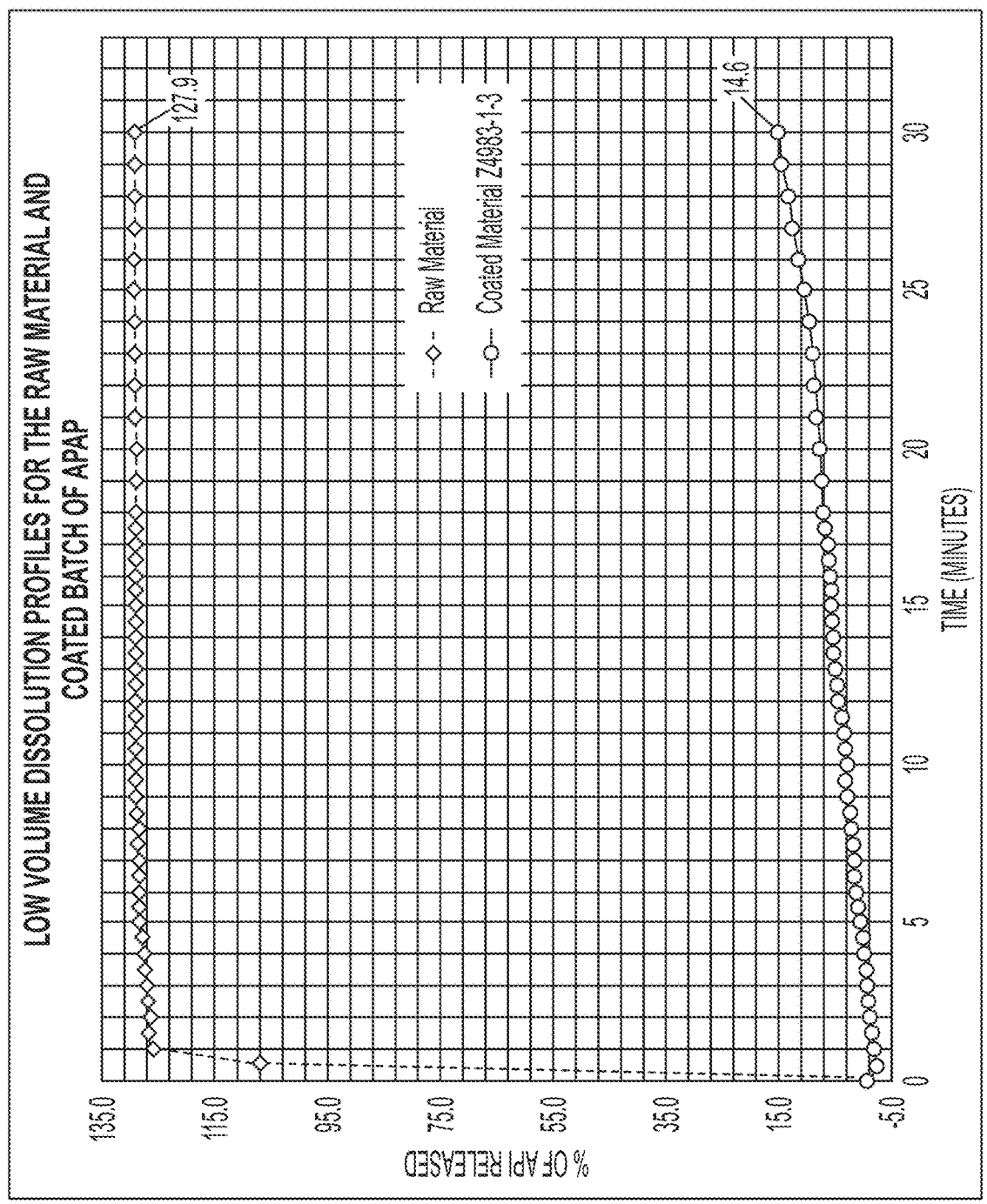
FIG. 27 is a chart illustrating APAP raw material and coated APAP using the low volume dissolution test.

The APAP Raw material and Coated APAP have been assessed over a period of 30 minutes. APAP raw material is readily dissolved and reaches an equilibrium point over 100% within the first two minutes. The Coated APAP has undergone coating at bench scale operation using the Resonance Acoustic Mixing manufacturing process. The dissolution results of the coated APAP material showed a significantly slower % drug release profile than the respective uncoated raw material. The profile remains slow with less than 15% drug dissolved for the 30-minute showing a slow release profile across the period. The slow release profile is indicative of achieving a successful coating and preventing the API from readily dissolving and therefore a taste masked API. The following Table 16 and FIG. 27 illustrate the significantly reduced dissolution profile achieved for the coating of APAP.

TABLE 16

(APAP Raw Material and Coated Dissolution Profiles)

| | % Ibuprofen Dissolved | |
|---|---|---|
| Time (minutes) | Raw Material - AN190319 | Coated batch Z4983-1-3 |
| 0.0 | 0 | 0.0 |
| 5 | 127 | 0.5 |
| 10 | 128 | 3.2 |
| 15 | 128 | 5.2 |

TABLE 16-continued (APAP Raw Material and Coated Dissolution Profiles)

| | % Ibuprofen Dissolved | |
| --- | --- | --- |
| Time (minutes) | Raw Material - AN190319 | Coated batch Z4983-1-3 |
| 20 | 128 | 7.5 |
| 25 | 128 | 10.2 |
| 30 | 128 | 14.6 |

Additional Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X". In addition, reference to phrases "less than", "greater than", "at most", "at least", "less than or equal to", "greater than or equal to", or other similar phrases followed by a string of values or parameters is meant to apply the phrase to each value or parameter in the string of values or parameters. For example, a statement that a layer has a thickness of at least about 5 cm, about 10 cm, or about 15 cm is meant to mean that the layer has a thickness of at least about 5 cm, at least about 10 cm, or at least about 15 cm.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The above description is presented to enable a person skilled in the art to make and use the disclosure, and is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein.

The invention claimed is:

1. A pharmaceutical composition comprising:
   60-85% w/w API;
   10-30% w/w a water insoluble material surrounding the API to form a first coating on the API;
   0.5-3% w/w silica surrounding the first coating of the API to form a second coating on the first coating of the API, wherein the silica produces a slower dissolution profile for the API as compared to API without silica;
   3-7% w/w matrix former; and
   2-6% w/w structure former.

2. The pharmaceutical composition of claim 1, wherein the water insoluble material comprises a wax.

3. The pharmaceutical composition of claim 2, wherein the wax comprises carnauba wax.

4. The pharmaceutical composition of claim 1, wherein the silica comprises hydrophobic silica.

5. The pharmaceutical composition of claim 1, wherein the matrix former comprises gelatin.

6. The pharmaceutical composition of claim 1, wherein the structure former comprises mannitol.

7. The pharmaceutical composition of claim 1, further comprising a viscosity modifier.

8. The pharmaceutical composition of claim 7, wherein the pharmaceutical composition comprises 0.1-1% w/w viscosity modifier.

9. The pharmaceutical composition of claim 7, wherein the viscosity modifier comprises xanthan gum.

10. The pharmaceutical composition of claim 1, further comprising a sweetener.

11. The pharmaceutical composition of claim 10, wherein the pharmaceutical composition comprises 0.1-2% w/w sweetener.

12. The pharmaceutical composition of claim 10, wherein the sweetener is sucralose.

13. The pharmaceutical composition of claim 1, further comprising a flavoring agent and/or an anti-aeration agent.

14. The pharmaceutical composition of claim 13, wherein the pharmaceutical composition comprises 0.5-3% w/w flavoring agent and/or anti-aeration agent.

15. The pharmaceutical composition of claim 13, wherein the flavoring agent and/or anti-aeration agent comprises terpene and/or terpinol.

16. The pharmaceutical composition of claim 1, wherein the pharmaceutical composition has a mid volume 60-minute dissolution test result less than or equal to 70% after 15 minutes.

17. A method of preparing coated API comprising:
   sieving raw API;
   mixing sieved raw API and a water insoluble material in a vessel;
   applying mechanical energy to the vessel and heating the vessel to a temperature greater than or equal to 50° C.; and
   adding silica to the vessel while continuing to apply the mechanical energy and maintaining the temperature of the vessel to form coated API comprising at least one coating comprising water insoluble material and silica, wherein the coated API comprises 40-85% w/w API, 10-60% w/w water insoluble material surrounding the API to form a first coating on the API, and 0.5-5% w/w silica surrounding the first coating of the API to form a second coating on the first coating of the API, wherein the silica produces a slower dissolution profile for the API as compared to API without silica.

18. The method of claim 17, wherein sieving the raw API comprises sieving the raw API to an average particle size of 75-250 microns.

19. The method of claim 17, further comprising sieving the coated API.

20. The method of claim 19, wherein sieving the coated API comprises sieving the coated API to an average particle size of 75-250 microns.

21. The method of claim 17, wherein the ratio of the at least one coating to the API of the API comprising at least one coating is 15-40:60-85.

22. The method of claim 17, wherein the coated API has a low volume 60 minute dissolution test result less than or equal to 70% after 15 minutes.

23. A method of preparing a pharmaceutical composition comprising:
    forming a pharmaceutical suspension comprising:
    30-50% w/w API comprising at least one coating, wherein the at least one coating comprises a water insoluble material and silica;
    1-5% w/w a matrix former;
    1-3% w/w a structure former; and
    a solvent;
    dosing the pharmaceutical suspension into a mold; and
    freeze drying the dosed pharmaceutical suspension in the mold to form the pharmaceutical composition, wherein the pharmaceutical composition comprises 60-85% w/w API, 10-30% w/w water insoluble material surrounding the API to form a first coating on the API, 0.5-3% w/w silica surrounding the first coating of the API to form a second coating on the first coating of the API, wherein the silica produces a slower dissolution profile for the API as compared to API without silica.

* * * * *